(12) United States Patent
Bisgard-Frantzen et al.

(10) Patent No.: US 7,374,922 B2
(45) Date of Patent: May 20, 2008

(54) STARCH DEBRANCHING ENZYMES

(75) Inventors: Henrik Bisgard-Frantzen, Bagsvaerd (DK); Allan Svendsen, Birkerod (DK)

(73) Assignee: Novozymes A/S, Bagsvaerd (DK)

(*) Notice: Subject to any disclaimer, the term of this patent is extended or adjusted under 35 U.S.C. 154(b) by 594 days.

(21) Appl. No.: 10/375,720

(22) Filed: Feb. 26, 2003

(65) Prior Publication Data

US 2003/0190738 A1 Oct. 9, 2003

Related U.S. Application Data

(63) Continuation of application No. 09/833,435, filed on Mar. 26, 2001, now abandoned, which is a continuation of application No. 09/346,237, filed on Jul. 1, 1999, now Pat. No. 6,265,197.

(60) Provisional application No. 60/094,353, filed on Jul. 28, 1998.

(30) Foreign Application Priority Data

Jul. 2, 1998 (DK) .............................. 1998 00868

(51) Int. Cl.
*C12N 9/44* (2006.01)
*C12N 15/00* (2006.01)
*C12P 21/06* (2006.01)
*C07H 21/04* (2006.01)

(52) U.S. Cl. .................. 435/210; 435/69.1; 435/320.1; 536/23.2

(58) Field of Classification Search .................. 435/4, 435/6, 69.1, 183, 200 T, 210 T, 252–3, 254.3, 435/254.76, 320–1; 536/23–74; 530/350
See application file for complete search history.

(56) References Cited

U.S. PATENT DOCUMENTS

| 4,335,208 A | 6/1982 | Norman |
| 4,560,651 A | 12/1985 | Nielsen et al. |
| 5,352,602 A | 10/1994 | Yamada et al. |
| 6,265,197 B1* | 7/2001 | Bisgrd-Frantzen et al. . 435/210 |
| 6,300,115 B1* | 10/2001 | Teague et al. ............... 435/210 |
| 6,350,599 B1* | 2/2002 | Svendsen .................... 435/183 |

FOREIGN PATENT DOCUMENTS

| WO | WO 95/23850 | 9/1995 |
| WO | WO 95/23852 | 9/1995 |
| WO | WO 95/23853 | 9/1995 |
| WO | WO 99/01545 | 1/1999 |
| WO | WO 99/35274 | 7/1999 |
| WO | WO 99/49022 | 9/1999 |

OTHER PUBLICATIONS

Katsuragi et al. (Gen Bank Acc. No. A26879, Jun. 1988.*
Yamashita et al., J. Biochem., vol. 116, pp. 1233-1240 (1994).
Cheng et al., J. Mol. Biol., vol. 288, pp. 623-634 (1999).
Abstract of article by Fierobe et al., Biochemistry, vol. 35, No. 26, pp. 8696-8704 (1996).
Abstract of Article by Nakamura et al., Protein Eng., vol. 10, No. 11, pp. 1263-1269 (1997).
Wantabe et al., Journal of Molecular Catalysis B: Enzymatic, vol. 4, pp. 167-180 (1998).
Abstract of article by Watanabe et al., Appl. Environ. Microbiol., vol. 62, pp. 2066-2073, 1996.
Abstract of JP Patent 48091272.
Wantanabe et al. , Applied and Environmental Microbiology, vol. 62, pp. 2066-2073.
Abstract of Article by Kosei (a) et al., Enzyme and Microbial Technology, vol. 19, No. 6, pp. 456-461 (1996).
Abstract of Japanese Patent JP 48091272.

* cited by examiner

*Primary Examiner*—Rebecca E. Prouty
*Assistant Examiner*—Ganapathirama Raghu
(74) *Attorney, Agent, or Firm*—Michael W. Krenicky

(57) ABSTRACT

The invention relates to a genetically engineered variant of a parent starch debranching enzyme, i.e. a pullulanase or an isamylase, the enzyme variant having an improved thermostability at a pH in the range of 4-6 compared to the parent enzyme and/or an increased activity towards amylopectin and/or glycogen compared to the parent enzyme, to methods for producing such starch debranching enzyme variants with improved thermostability and/or altered substrate specificity, and to a method for converting starch to one or more sugars using at least one such enzyme variant.

11 Claims, 10 Drawing Sheets

```
SEQ ID NO 5 = pullulanase from Klebsiella pneumoniae
SEQ ID NO 6 = pullulanase from Klebsiella aerogenes
SEQ ID NO 1 = pullulanase from Bacillus acidopullulyticus
SEQ ID NO 2 = pullulanase from Bacillus deramificans 1                                                           50
SEQ ID NO 5   ....MLRYTR NALVLGSLVL LSGCDNGSSS SSSGN..... .......PDT
SEQ ID NO 6   ....MLRYTC HALFLGSLVL LSGCDNSSSS STSGSPGSPG NPGNPGTPGT
SEQ ID NO 1   VSLIRSRYNH FVILFTVAIM FLTVCFPAYK ALADSTSTEV IVHYHRFDSN
SEQ ID NO 2   ....MAKKLI YVCLSVCLVL TWAFNVKGQS AHADGNTTTI IVHYFRPAGD 51                                                          100
SEQ ID NO 5   PDNQDVVVR. LPDVAVPGEA VTAVENQAVI HLVDIAGITS .SSAADYSSK
SEQ ID NO 6   PDPQDVVVR. LPDVAVPGEA VQASARQAVI HLVDIAGITS .STPADYATK
SEQ ID NO 1   YANWDLWMWP YQPVNGNGAA YEFSGKDD.F GVKADVQVPG DDTQVGLIVR
SEQ ID NO 2   YQPWSLWMW. ..PKDGGGAE YDFNQPADSF GAVASADIPG NPSQVGIIVR 101                                                         150
SEQ ID NO 5   NLYLWNNETC DALSAPVADW NDVSTTPSGS DKYGPYWVIP LNKESGCINV
SEQ ID NO 6   NLYLWNNETC DALSAPVADW NDVSTTPTGS DKYGPYWVIP LTKESGSINV
SEQ ID NO 1   TNDWSQKNTS DDLHIDLTKG HEIWIVQGDP NIYYNLSDAQ AAAATPKVSNA
SEQ ID NO 2   TQDWT.KDVS ADRYIDLSKG NEVWLVEGNS QIFYNEKDAE DAAKPAVSNA 151                                                         200
SEQ ID NO 5   IVRDGTDKLI DSDLRVAFGD ......FTDR TVS.VIAGNS AVYDSRADAF
SEQ ID NO 6   IVRDGTNKLI DSG.RVSFSD ......FTDR TVS.VIAGNS AVYDSRADAF
SEQ ID NO 1   YLDNEKTVLA KLTNPMTLSD GSSGFTVTDK TTGEQIPVTA ATNANSA...
SEQ ID NO 2   YLDASNQVLV KLSQPLTLGE GASGFTVHDD TANKDIPVTS VKDASLGQDV 201                                                         250
SEQ ID NO 5   RAAFGVALAE AHWVDKNTLL WPGGQDKPIV RLYYSHSSKV AAD.......
SEQ ID NO 6   RAAFGVALAD AHWVDKTTLL WPGGENKPIV RLYYSHSSKV AAD.......
SEQ ID NO 1   .......... .......... .......... .......... ..........
SEQ ID NO 2   TAVLAGTFQH IFGGSDWAPD NHSTLLKKVT NNLYQFSGDL PEGNYQYKVA 251                                                         300
SEQ ID NO 5   .....GEGKF TDRYLKLTPT TVSQQVSMRF ...PHLSSYA AFKLPDNANV
SEQ ID NO 6   .....SNGEF SDKYVKLTPT TVNQQVSMRF ...PHLASYP AFKLPDDVNV
SEQ ID NO 1   .......... .......... .......... .......... ..........
SEQ ID NO 2   LNDSWNNPSY PSDNINLTVP AGGAHVTFSY IPSTHAVYDT INNPNADLQV 301                                                         350
SEQ ID NO 5   DELLQGETVA IAAAEDGILI SATQVQTAGV LDDAYAEAA. ........EA
SEQ ID NO 6   DELLQGDDGG IAES.DGILS LSHPGADRRR AGRYLCRRA. ........EA
SEQ ID NO 1   SSSEQTDLVQ LTLASAPDVS HTIQVGAAGY EAVNLIPRNV LNLPRYYYSG
SEQ ID NO 2   ESGVKTDLVT VTLGEDPDVS HTLSIQTDGY QAKQVIPRNV LNSSQYYYSG
```

Fig. 1(a)

```
               351                                                       400
SEQ ID NO 5    LSYGAQLADG  GVTFRVWAPT  AQQVDVVVYS  ADKKVIGSHP  MTRDSASGAW
SEQ ID NO 6    LSYGAQLTDS  GVTFRVWAPT  AQQVELVIYS  ADKKVIASHP  MTRDSASGAW
SEQ ID NO 1    NDLGNVYSNK  ATAFRVWAPT  ASDVQLLLYN  SETGPVTKQL  EMQKSDNGTW
SEQ ID NO 2    DDLGNTYTQK  ATTFKVWAPT  STQVNVLLYD  SATGSVTKIV  PMTASGHGVW 401                                                       450
SEQ ID NO 5    SWQGGSDLKG  AFYRYAMTVY  HPQSRKVEQY  EVTDPYAHSL  STNSEYSQVV
SEQ ID NO 6    SWQGGSDLKG  AFYRYAMTVY  HPQSRKVEQY  EVTDPYAHSL  STNSEYSQVV
SEQ ID NO 1    KLKVPGNLKN  WYYLYQVTVN  GKTQTAV...  ...DPYVRAI  SVNATRGMIV
SEQ ID NO 2    EATVNQNLEN  WYYMYEVTGQ  GSTRTAV...  ...DPYATAI  APNGTRGMIV 451                                                       500
SEQ ID NO 5    DLNDSALKPD  GWDNLTMPHA  QKTKADLAKM  TIHESHIRDL  SAWDQTVPAE
SEQ ID NO 6    DLNDSALKPE  GWDGLTMPHA  QKTKADLAKM  TIHESHIRDL  SAWDQTVPAE
SEQ ID NO 1    DLEDT..NPP  GWKE....DH  QQTPANPVDE  VIYEVHVRDF  SI.DANSGMK
SEQ ID NO 2    DLAKT..DPA  GWNS....DK  HITPKNIEDE  VIYEMDVRDF  SI.DPNSGMK 501                                                       550
SEQ ID NO 5    LRGKYLALTA  GDSNMVQHLK  T....LSASG  VTHVELLPVF  DLATVNEFSD
SEQ ID NO 6    LRGKYLALTA  QESNMVQHLK  Q....LSASG  VTHIELLPVF  DLATVNEFSD
SEQ ID NO 1    NKGKYLAFTE  HGTKGPDNVK  TGIDSLKELG  INAVQLQPIE  EFNSIDE...
SEQ ID NO 2    NKGKYLALTE  KGTKGPDNVK  TGIDSLKQLG  ITHVQLMPVF  ASNSVDE...

551                                                       600
SEQ ID NO 5    KVADIQQPFS  RLCEVNSAVK  SSEFAGYCDS  GSTVEEVLNQ  LKQSDSQDNP
SEQ ID NO 6    KVADIQQPFS  RLCEVNSAVK  SSEFAGYCDS  GSTVEEVLTQ  LKQNDSKDNP
SEQ ID NO 1    ..........  ..........  ..........  ..........  ..........
SEQ ID NO 2    ..........  ..........  ..........  ..........  ..........

601                                                       650
SEQ ID NO 5    QVQALNTLVA  QTDSYNWGYD  PFHYTVPEGS  YATDPEGTTR  IKEFRTMIQA
SEQ ID NO 6    QVQALNTLVA  QTDSYNWGYD  PFHYTVPEGS  YATDPEGTAR  IKEFRTMIQA
SEQ ID NO 1    ........T   QPNMYNWGYD  PRNYNVPEGA  YATTPEGTAR  ITQLKQLIQS
SEQ ID NO 2    ........T   DPTQDNWGYD  PRNYDVPEGQ  YATNANGNAR  IKEFKEMVLS 651                                                       700
SEQ ID NO 5    IKQDLGMNVI  MDVVYNHTNA  AGPTDRTSVL  DKIVPWYYQR  LNETTGSVES
SEQ ID NO 6    IKQDLGMNVI  MDVVYNHTNA  AGPTDRTSVL  DKIVPWYYQR  LNETTGSVES
SEQ ID NO 1    IHKD.RIAIN  MDVVYNHTFN  VGVSD....F  DKIVPQYYR   TDSAGNYTNG
SEQ ID NO 2    LHRE.HIGVN  MDVVYNHTFA  TQISD....F  DKIVPEYYYR  TDDAGNYTNG 701                                                       750
SEQ ID NO 5    ATCCSDSAPE  HRMFAKLIAD  SLAVWTTDYK  IDGFRFDLMG  YHPKAQILSA
SEQ ID NO 6    ATCCSDSAPE  HRMFAKLIAD  SLAVWTTDYK  IDGFRFDLMG  YHPKAQILSA
SEQ ID NO 1    SGVGNEIATE  RPMVQKFVLD  SVKYWVKEYH  IDGFRFDLMA  LLGKDTMAKI
SEQ ID NO 2    SGTGNEIAAE  RPMVQKFIID  SLKYWVNEYH  IDGFRFDLMA  LLGKDTMSKA
```

Fig. 1(b)

```
                751                                                              800
SEQ ID NO 5   WERIKALNPD  IYFFGEGWDS  NQSDRF..EI  ASQINLKGTG  IGTFSDRLRD
SEQ ID NO 6   WERIKALNPD  IYFFGEGWDS  NQSDRF..EI  ASQINLKGTG  IGTFSDRLRD
SEQ ID NO 1   SKELHAINPG  IVLYGEPWTG  GTSGLSSDQL  VTKGQQKGLG  IGVFNDNIRN
SEQ ID NO 2   ASELHAINPG  IALYGEPWTG  GTSALPDDQL  LTKGAQKGMG  VAVFNDNLRN 801                                                              850
SEQ ID NO 5   SVRGGGPFDS  GDALRQNQGI  GSGAGVLPNE  LASLSDDQVR  HLADLTRLGM
SEQ ID NO 6   AVRGGGPFDS  GDALRQNQGV  GSGAGVLPNE  LTTLSDDQAR  HLADLTRLGM
SEQ ID NO 1   GL.DGNVFDK  SA.....QGF  ATGDPNQVNV  IKN.......  ..........
SEQ ID NO 2   AL.DGNVFDS  SA.....QGF  ATGATGLTDA  IKN.......  ..........

851                                                              900
SEQ ID NO 5   AGNLADFVMI  DKDGAAKKGS  EIDYNGAPGG  YAADPTEVVN  YVSKHDNQTL
SEQ ID NO 6   AGNLADFVLI  DKDGAVKRGS  EIDYNGAPGG  YAADPTEVVN  YVSKHDNQTL
SEQ ID NO 1   ..........  ..........  ..RVMGSISD  FTSAPSETIN  YVTSHDNMTL
SEQ ID NO 2   ..........  ..........  ..GVEGSIND  FTSSPGETIN  YVTSHDNYTL 901                                                              950
SEQ ID NO 5   WDMISYKASQ  EADLATRVRM  QAVSLATVML  GQGIAFDQQG  SELLRSKSFT
SEQ ID NO 6   WDMISYKAAQ  EADLDTRVRM  QAVSLATVML  GQGIAFDQQG  SELLRSKSFT
SEQ ID NO 1   WDKISASNPN  DTQ.ADRIKM  DELAQAVVFT  SQGVPFMQGG  EEMLRTKGGN
SEQ ID NO 2   WDKIALSNPN  DSE.ADRIKM  DELAQAVVMT  SQGVPFMQGG  EEMLRTKGGN 951                                                             1000
SEQ ID NO 5   RDSYDSGDWF  NRVDYSLQDN  NYNVGMPRIS  DDGSNYEVIT  RVKEMVATPG
SEQ ID NO 6   RDSYDSGDWF  NRVDYSLQDN  NYNVGMPRSS  DDGSNYDIIA  RVKDAVATPG
SEQ ID NO 1   DNSYNAGDSV  NQFDWS....  ..........  ..........  .........R
SEQ ID NO 2   DNSYNAGDAV  NEFDWS....  ..........  ..........  .........R 1001                                                             1050
SEQ ID NO 5   EAELKQMTAF  YQELTELRKS  SPLFTLGDGS  AVMKRVDFRN  TGSDQQAGLL
SEQ ID NO 6   ETELKQMTAF  YQELTALRKS  SPLFTLGDGA  TVMKRVDFRN  TGADQQTGLL
SEQ ID NO 1   KAQFENVFDY  YSWLIHLRDN  HPAFRMTTAD  QIKQNLTFLD  SPTN......
SEQ ID NO 2   KAQYPDVFNY  YSGLIHLRLD  HPAFRMTTAN  EINSHLQFLN  SPEN......

1051                                                             1100
SEQ ID NO 5   VMTVDDGMKA  GASLD...SR  LDGLVVAINA  APESRTLNEF  AGETLQLSAI
SEQ ID NO 6   VMTIDDGMQA  GRQSGQPCRR  HRGGDQRRAG  KPDAAGLRRH  IAPAERYSA.
SEQ ID NO 1   ..TVAFELKN  HANHD....K  WKNIIVMYNP  NKTAQTLT.L  PSGNWTIVGL
SEQ ID NO 2   ..TVAYELTD  HVNKD....K  WGNIIVVYNP  NKTVATIN.L  PSGKWAINAT 1101                                                             1148
SEQ ID NO 5   QQTAGENSLA  NGVQIAADGT  VTLPAWSVAV  LELPQGEAQG  AGLPVSSK
SEQ ID NO 6   ..GGGRPVAG  ERVQVAADGS  VTLPAWSVAV  LELPQASRRA  LACR....
SEQ ID NO 1   GNQVGEKSLG  H.....VNGT  VEVPALSTII  LHQGTSEDVI  DQN.....
SEQ ID NO 2   SGKVGESTLG  Q.....AEGS  VQVPGISMMI  LHQEVSPDHG  KK......
```

Fig. 1(c)

SEQ ID NO 4 = isoamylase from *Pseudomonas amyloderamosa*
SEQ ID NO 7 = isoamylase from *Pseudomonas* sp. SMP1
SEQ ID NO 8 = isoamylase from *Favobacterium odoratum*
SEQ ID NO 9 = isoamylase from *Sulfolobus acidocaldarius*
SEQ ID NO 10 = isoamylase from *Sulfolobus solfataricus*
SEQ ID NO 3 = isoamylase from *Rhodothermus marinus*
SEQ ID NO 11 = isoamylase from *Zea mays*

```
                     1                                                           50
      SEQ ID NO  4   ..........  ..........  ..........  ..........  ..........
      SEQ ID NO  7   ..........  ..........  ..........  ..........  ..........
      SEQ ID NO  8   ..........  ..........  ..........  ..........  ..........
      SEQ ID NO  9   ..........  ..........  ..........  ..........  ..........
      SEQ ID NO 10   ..........  ..........  ..........  ..........  ..........
      SEQ ID NO  3   ..........  ..........  ..........  ..........  ..........
      SEQ ID NO 11   RLVTHSTRTH  YLIGQSQTNW  APSPPLPLPM  AQKLPCVSSP  RPLLAVPAGR 51                                                         100
      SEQ ID NO  4   ..........  ..........  ..........  .....MKCPK  ILAALLGCAV
      SEQ ID NO  7   ..........  ..........  ..........  .....MKCPK  ILAALLGCAV
      SEQ ID NO  8   ..........  ..........  ....MFNKYK  QISETDMQRT  ILAALLTGAL
      SEQ ID NO  9   ..........  ..........  ..........  ..........  ..........
      SEQ ID NO 10   ..........  ..........  ..........  ..........  .......MAL
      SEQ ID NO  3   ..........  ..........  ..........  ..........  .....MSHSA
      SEQ ID NO 11   WRAGVRGRPN  VAGLGRGRLS  LHAAAARPVA  EAVQAEEDDD  DDDEEVAEER 101                                                        150
      SEQ ID NO  4   LAGVPAMPAH  AAINSMSLGA  SYDAQQANIT  FRVYSSQATR  IVLYLYSAGY
      SEQ ID NO  7   LAGVPAMPAH  AAINSMSLGA  SYDAQQANIT  FRVYSSQATR  IVLYLYSAGY
      SEQ ID NO  8   LGA....PAW  AAINPNKLGA  AYDATKANVT  FKVYSSKATR  IELYLYSTAT
      SEQ ID NO  9   ...MKDRPLK  PG.EPYPLGA  TWIEEEDGVN  FVLFSENATK  VELLTYSQTR
      SEQ ID NO 10   FFRTRDRPLR  PG.DPYPLGS  NWIEDDDGVN  FSLFSENAEK  VELLLYSLTN
      SEQ ID NO  3   QPVTSVQAVW  PG.RPYPLGA  TW..DGLGVN  FALYSQHAEA  VELVLFDHPD
      SEQ ID NO 11   FALGGACRVL  AG.MPAPLGA  TALRG..GVN  FAVYSSGASA  ASLSLFAPGD 151                                                        200
      SEQ ID NO  4   GVQESATYTL  SPAGSGVWAV  TVPVSSIKAA  GITGAVYYGY  RAWGPNWPYA
      SEQ ID NO  7   GVQESATYTL  SPAGSGVWAV  TVPVSSIKAA  GITGAVYYGY  RAWGPNWPYA
      SEQ ID NO  8   GSAEKAKYVM  TNSG.GIWSV  TIPTSTLSGQ  GLGGTLYYGY  RAWGPNWPYN
      SEQ ID NO  9   QDEPKEIIEL  R.....QRTG  DLWHVFVPGL  R.PGQL.YGY  RVYGPYKP..
      SEQ ID NO 10   QKYPKEIIEV  K.....NKTG  DIWHVFVPGL  R.PGQL.YAY  RVYGPYKP..
      SEQ ID NO  3   DPAPSRTIEV  T.....ERTG  PIWHVYLPGL  R.PGQL.YGY  RVYGPYRP..
      SEQ ID NO 11   LKADRVTEEV  PLDPLLNRTG  NVWHVFIHGD  ELHGML.CGY  RFDGVFAP..
```

Fig. 2(a)

```
              201                                                              250
SEQ ID NO 4   SNWGKGSQAG FVSDVDANGD RFNPNKLLLD PYAQEVSQDP LNPSNQNGNV
SEQ ID NO 7   SNWGKGSQAG FVSDVDANGD RFNPNKLLLD PYAQEVSQDP LNPSNQNGNV
SEQ ID NO 8   ASWTKGSSLG FISDVDAAGN RFNPNKLLSD PYALELSHDP TTATMTNGSI
SEQ ID NO 9   .......... ......EEGL RFNPNKVLID PYAKAINGLL LWDDSVFGYK
SEQ ID NO 10  .......... ......ELGL RFNPNKVLID PYAKAINGSV IWNDAVFGYK
SEQ ID NO 3   .......... ......EEGH RFNPNKVLLD PYAKAIGRPL RWHDSLFGYK
SEQ ID NO 11  .......... ......ERGQ YYDVSNVVVD PYAKAVVSR. ..........

251                                                              300
SEQ ID NO 4   FASGA...SY RTTDSGIYAP KGVVLVPSTQ STGTK....P TRAQKDDVIY
SEQ ID NO 7   FASGA...SY RTTDSGIYAP KGVVLVPSTQ STGTK....P TRAQKDDVIY
SEQ ID NO 8   YASGA...TY RNIDSGSSAP KGIVLAGDTQ ATGTK....P TRALKDDVVY
SEQ ID NO 9   IGDQNQDLSF DERKDDKFIP KGVIINPYFD WEDEHFFFRR KIPFKDSIIY
SEQ ID NO 10  IGDQNQDLTY DERDSGEYVP KSVVINPYFE WDDEDFIKGK KVPLKDTVIY
SEQ ID NO 3   IGDPAGDLSF SEEDSAPYAP LGAVVEGCFE WGDDR...PP RIPWEDTIIY
SEQ ID NO 11  .....GEYGV PAPGGSCWPQ MAGMIPLPYN KFDWQGDLPL GYHQKDLVIY 301                                                              350
SEQ ID NO 4   EVHVRGFTEQ DTSIPAQYRG TYYGAGLKA. .SYLASLGVT AVEFLPVQET
SEQ ID NO 7   EVHVRGFTEQ DTSIPAQYRG TYYGAGLKA. .SYLASLGVT AVEFLPVQET
SEQ ID NO 8   EAHVRGLTMN DTSITAAYRG TYKGAGLKA. .AALAALGVT AIEFLPVQET
SEQ ID NO 9   ETHIKGITKL RQDLPENVRG TFLGLASDTM IDYLKDLGIT TVEIMPIQQF
SEQ ID NO 10  EVHVKGFTKL RLDLPENIRG TYEGLASEQM ISYLKDLGIT TVELMPVFHF
SEQ ID NO 3   ETHVKGITKL HPEVPEPLRG TYLGLTCEPV LEHLKQLGVT TIQLLPVHAK
SEQ ID NO 11  EMHLRGFTK. HNSSKTKHPG TYIGAVSK.. LDHLKELGVN CIELMPCHEF 351                                                              400
SEQ ID NO 4   QNDANDVVPN SDANQNYWGY MTENYFSPDR RYAYN...KA AGGPTAEFQA
SEQ ID NO 7   QNDANDVVPN SDANQNYWGY MTENYFSPDR RYAYN...KA AGGPTAEFQA
SEQ ID NO 8   QNDTNDNDPS STSGDNYWGY MTLNYFAPDR RYAYD...KT PGGPTREFKE
SEQ ID NO 9   VDERFIV... DKGLKNYWGY NPINYFSPEC RYSSSG...C LGNQVIEFKK
SEQ ID NO 10  IDQRFLT... DKGLTNYWGY DPINFFSPEC RYSSTG...C LGGQVLSFKK
SEQ ID NO 3   VHDRHLV... ERGLRNYWGY NPLCYFAPEP EYATNG...P ISA.VREFKM
SEQ ID NO 11  NELEYFS... SSSKMNFWGY STINFFSPMA RYSSSGIRDS GCGAINEFKA 401                                                              450
SEQ ID NO 4   MVQAFHNAGI KVYMDVVYNH TAEGGTWTSS DPTTATIYSW RGLDNATYYE
SEQ ID NO 7   MVQAFHNAGI KVYMDVVYNH TAEGGTWTSS DPTTATIYSW RGLDNTTYYE
SEQ ID NO 8   MVKAFHDNGI KVLVDVVYNH TGEGGAWSPT DKTTYNITSF RGLDNPTYYS
SEQ ID NO 9   LVNSLHNAGL EVIIDVVYNH TAEGNHLGP. ......TLSF KGIDNSSYYM
SEQ ID NO 10  MVNELHNAGI EVIIDVVYNH TAEGNHLGP. ......TLSF RGIDNTAYYM
SEQ ID NO 3   MVRALHAAGF EVIVDVVYNH TGEGGVLGP. ......TLSF RGIDNRAYYK
SEQ ID NO 11  FVREAHKRGI EVIMDVVFNH TAEGNEKGP. ......ILSF RGIDNSTYYM
```

Fig. 2(b)

```
              451                                                              500
SEQ ID NO  4  LTSGNQ.YFY  DNTGIGANFN  TYNTVAQNLI  VDSLAYWANT  MGVDGFRFDL
SEQ ID NO  7  LTSGNQ.YFY  DNTGIGANFN  TYNTVAQNLI  VDSLAYWANT  MGVDGFRFDL
SEQ ID NO  8  LTADFQ.NSW  DNTGVGGNYN  TRNTIAQNLI  VDSLAYWRDK  LGVDGYRFDL
SEQ ID NO  9  LDPKNKRYYI  DFTGTGNTLN  LSHPRVLQLV  LDSLRYWVLE  MHVDGFRFDL
SEQ ID NO 10  LQPDNKRYYL  DFTGTGNTLN  LSHPRVIQMV  LDSLRYWVTE  MHVDGFRFDL
SEQ ID NO  3  ADPNNPRFLV  DYTGTGNTLD  VGNPYVIQLI  MDSLRYWVTE  MHVDGFRFDL
SEQ ID NO 11  LAPKGE..FY  NYSGCGNTFN  CNHPVVREFI  VDCLRYWVTE  MHVDGFRFDL 501                                                              550
SEQ ID NO  4  ASVLGNSCLN  GAYTASAPNC  PNGGYNFDAA  DSNVAINRIL  REFTVRPAAG
SEQ ID NO  7  ASVLGNSCLN  GAYTASAPNC  PNGGYNFDAA  DSNVAINRIL  REFTVRPAAG
SEQ ID NO  8  ASVLGNS...  .........C  QHGCFNFDKM  DAGNALNRIV  AELPPRPATG
SEQ ID NO  9  ASALARQ...  .LYS......  ....VNMLST  ........FF  VAIQQDPIL.
SEQ ID NO 10  AAALARE...  .LYS......  ....VNMLNT  ........FF  IALQQDPIL.
SEQ ID NO  3  AAALARE...  .LYD......  ....VDMLST  ........FF  QVIQQDPVL.
SEQ ID NO 11  ASILTRGC..  SLWDPVNVYG  SPMEGDMITT  GTPLVAPPLI  DMISNDPIL.

551                                                              600
SEQ ID NO  4  GSGLDLFAEP  WAIGGNSYQL  GGFP..QGWS  EWNGLFRDSL  RQAQNELGSM
SEQ ID NO  7  GSGLDLFAEP  WAIGGNSYQL  GGFP..QGWS  EWNGLFRDSL  RQAQNELGSM
SEQ ID NO  8  GSGVDLIAEP  WAIGGNSYQV  GGFP..SGWA  EWNGAYRDVV  RQAQNKLGSV
SEQ ID NO  9  .SQVKLIAEP  WDVGPGGYQV  GNFPY..LWA  EWNGKYRDTI  RRF...WRGD
SEQ ID NO 10  .SQVKLIAEP  WDVGQGGYQV  GNFPY..QWA  EWNGKYRDSI  RRF...WRGE
SEQ ID NO  3  .SQVKLIAEP  WDVGPGGYQV  GHFPW..QWT  EWNGRYRDAV  RRF...WRGD
SEQ ID NO 11  .GNVKLIAEA  WDAG.GLYQE  GQFPHWNVWS  EWNGKYRDTV  RQF...IKGT 601                                                              650
SEQ ID NO  4  TIYVIQDAND  FSGSSNLFQS  SGRSPWNSIN  FIDVHDGMTL  KDVYSCNGAN
SEQ ID NO  7  TIYVTQDAND  FSGSSNLFQS  SGRSPWNSIN  FIDVHDGMTL  KDVYSCNGAN
SEQ ID NO  8  AITTGQMATR  FAGSSDLYGD  DGRKPWHSVN  FITAHDGFTL  KDLYSCNSKN
SEQ ID NO  9  PVPYEELANR  LLGSPDLYAG  SNKTPFASIN  YITSHDGFTL  QDLVSYNQKH
SEQ ID NO 10  ALPYSEIANR  LLGSPDIYLG  NNKTPFASIN  YVTSHDGFTL  EDLVSYNQKH
SEQ ID NO  3  RGLNGEFATR  FAGSSDLYER  SGRRPFASIN  FVTAHDGFTL  EDLVSYTKKH
SEQ ID NO 11  DGFAGAFAEC  LCGSPQLYQA  GGRKPWHSIG  FVCAHDGFTL  ADLVTYNSKY 651                                                              700
SEQ ID NO  4  NSQAWPYGPS  DGGTSTNYSW  D...QGMSAG  TGAAVDQRRA  ARTGMAFEML
SEQ ID NO  7  NSQAWPYGPS  DGGTSTNYSW  D...QGMSAG  TGAAVDQRRA  ARTGMAFEML
SEQ ID NO  8  NNQVWPYGPS  DGGEDNNNSW  D...QG....  .GIAADQRKA  ARNGMALMML
SEQ ID NO  9  NEANK..LNN  EDGMNENYSW  NCGVEGETND  SNILYCREKQ  RRNFVITLFV
SEQ ID NO 10  NEANG..FNN  QDGMNENYSW  NCGAEGPTND  QNVVICREKQ  KRNFMITLLV
SEQ ID NO  3  NEANL..EGN  RDGMDENYST  NCGVEGPTQD  PSVLACREAL  KRSLISTLFL
SEQ ID NO 11  NLSNG..EDF  RDGENHNLSW  NCGEEGEFAS  LSVRRLRKRQ  MRNFFVCLMV
```

Fig. 2(c)

```
              701                                                        750
SEQ ID NO 4   SAGTPLMQGG DEYLRTLQCN NNAYNLDSSA NWLTYSWTTD Q.SNFYTFAQ
SEQ ID NO 7   SAGTPLMQGG DEYLRTLQCN NNAYNLDSSA NWLTYSWTTD Q.SNFYTFAQ
SEQ ID NO 8   SAGVPMIVGG DEALRSMNCN NNPYNLDSSA NWLNWSRTTD Q.NNFQSFSK
SEQ ID NO 9   SQGIPMILGG DEIGRTQKGN NNAFCQDNET SWYDWN.LDE NRVRFHDFVR
SEQ ID NO 10  SQGTPMILGG DELSRTQRGN NNAFCQDNEI TWFDWN.LDE RKSKFLEFVK
SEQ ID NO 3   SQGVPMLLGG DELSRTQHGN NNAYCQDNEI SWYNWQ.LDT RKQQFLEFVR
SEQ ID NO 11  SQGVPMFYMG DEYGHTKGGN NNTYCHDHYV NYFRWDKKEE QSSDLYRFCR 751                                                        800
SEQ ID NO 4   RLIAFRKAHP ALRPSSWYSG ........SQ LTWYQPSGAV ADSNYWNNTS
SEQ ID NO 7   RLIAFRKAHP ALRPSSWYSG ........SQ LTWYQPSGAV ADSNYWNNTS
SEQ ID NO 8   AMIAFRKAHP ALRPANFYSS VDNNGNVMEQ LRWFKPDGGV ADATYFNDAN
SEQ ID NO 9   RLTNFYKAHP IFRRARYFQG KKLHGSPLKD VTWLKPDGNE VDDSVWKSPT
SEQ ID NO 10  KMIQFYRAHP AFRRERYFQG KKLFGMPLKD VTFYTLEGRE VDEKTWSSPT
SEQ ID NO 3   QTIWFRKQHR SFRRRHFLTG LPNGGRPRR. .SLVAPEGRP MRHEDWTNPE
SEQ ID NO 11  LMTEFRKECE SLGLEDFPTS ER........ ...LKWHGHQ PGKPDWSEAS 801                                                        850
SEQ ID NO 4   NYAIAYAING PSLGDSN... .....S.IYV AYNGWSSSVT FTLPAPPSGT
SEQ ID NO 7   NYAIAYAING PSLGDSN... .....S.IYV AYNGWSSSVT FTLPAPPSGT
SEQ ID NO 8   NHAIAWRIDG SEFGDTA... .....SAIYV AHNAWSAQVN FTLPWPGAGK
SEQ ID NO 9   NHII.YILEG SAIDEINYNG ERIADDTFLI ILNGASTNLK IKVPHG....
SEQ ID NO 10  QLVI.FVLEG SVMDEINMYG ERIADDSFLI ILNANPNNVK VKFPKG....
SEQ ID NO 3   LTAFGLLLHG DAIQGTDEHG RPFRDDTFLI LFNNGSEAVP VVVPEVCSCG
SEQ ID NO 11  RFV.AFTMKD ETKGEI.... ........YV AFNTSHLPVV VGLPERSG..

851                                                        900
SEQ ID NO 4   ...QWYRVTD TCDWNDGAST FVAPGSETLI GGAGTTYGQC GQSLLLLISK
SEQ ID NO 7   ...QWYRVTD TCDWNDGAST FVAPGSETLI GGAGTTYGQC GQSLLLLISK
SEQ ID NO 8   ...SWYRVTD TCGWAEGASQ VQAPGSEALV GGENTAYGLC GRGTLLLIAK
SEQ ID NO 9   ...KWELVLH P.......YP HEPSNDKKII ENNKE..VEI DGKTALIYRR
SEQ ID NO 10  ...KWELVIS S.......YL REIKPEERII EGEKE..LEI EGRTALVYRR
SEQ ID NO 3   KPHHWE.VVP V.......FQ RNVEPPTCAP GETLS..LPP GVLTVLVAVP
SEQ ID NO 11  ..FRWEPVVD TGKEAPYDFL TDGLPDRAVT VYQFSHFLNS NLYPMLSYSS

901
SEQ ID NO 4   ..........
SEQ ID NO 7   ..........
SEQ ID NO 8   ..........
SEQ ID NO 9   IEFQ......
SEQ ID NO 10  IEL.......
SEQ ID NO 3   PFSDGNTEPA
SEQ ID NO 11  IILVLRPDV.
```

Fig. 2(d)

```
               SEQ ID NO 1 = pullulanase from Bacillus acidopullulyticus
SEQ ID NO 2 = pullulanase from Bacillus deramificans
SEQ ID NO 3 = isoamylase from Rhodothermus marinus
SEQ ID NO 4 = isoamylase from Pseudomonas amyloderamosa 1                                                                           50
Seq.No.1   VSLIRSRYNH  FVILFTVAIM  FLTVCFPAYK  ALADSTSTEV  IVHYHRFDSN
Seq.No.2   ..........  ..........  ..........  ...DGNTTTI  IVHYFRPAGD
Seq.No.3   ..........  ..........  ..........  ..........  ..........
Seq.No.4   ..........  ..........  ..........  ..........  ..........

51                                                              100
Seq.No.1   YANWDLWMWP  YQPVNGNGAA  YEFSGKDD.F  GVKADVQVPG  DDTQVGLIVR
Seq.No.2   YQPWSLWMW.  ..PKDGGGAE  YDFNQPADSF  GAVASADIPG  NPSQVGIIVR
Seq.No.3   ..........  ..........  ..........  ..........  ..........
Seq.No.4   ..........  ..........  ..........  ..........  ..........

101                                                             150
Seq.No.1   TNDWSQKNTS  DDLHIDLTKG  HEIWIVQGDP  NIYYNLSDAQ  AAATPKVSNA
Seq.No.2   TQDWT.KDVS  ADRYIDLSKG  NEVWLVEGNS  QIFYNEKDAE  DAAKPAVSNA
Seq.No.3   ..........  ..........  ..........  ..........  ..........
Seq.No.4   ..........  ..........  ..........  ..........  ..........

151                                                             200
Seq.No.1   YLDNEKTVLA  KLTNPMTLSD  GSSGFTVTDK  TTGEQIPVTA  ATNANSA...
Seq.No.2   YLDASNQVLV  KLSQPLTLGE  GASGFTVHDD  TANKDIPVTS  VKDASLGQDV
Seq.No.3   ..........  ..........  ..........  ..........  ..........
Seq.No.4   ..........  ..........  ..........  ..........  ..........

201                                                             250
Seq.No.1   ..........  ..........  ..........  ..........  ..........
Seq.No.2   TAVLAGTFQH  IFGGSDWAPD  NHSTLLKKVT  NNLYQFSGDL  PEGNYQYKVA
Seq.No.3   ..........  ..........  ..........  ..........  ..........
Seq.No.4   ..........  ..........  ..........  ..........  ..........

251                                                             300
Seq.No.1   ..........  ..........  ..........  ..........  ..........
Seq.No.2   LNDSWNNPSY  PSDNINLTVP  AGGAHVTFSY  IPSTHAVYDT  INNPNADLQV
Seq.No.3   ..........  .MSHSAQPVT  SVQAVWPGRP  YPLGATWDGL  GVNFAL..YS
Seq.No.4   MKCPKILAAL  LGCAVLAGVP  AMPAHAAINS  MSLGASYDAQ  QANITFRVYS 301                                                             350
Seq.No.1   SSSEQTDLVQ  LTLASAPDVS  HTIQVGAAGY  EAVNLIPRNV  LNLPRYYYSG
Seq.No.2   ESGVKTDLVT  VTLGEDPDVS  HTLSIQTDGY  QAKQVIPRNV  LNSSQYYYSG
Seq.No.3   QHAEAVELVL  FDHPDDPAPS  RTIEVTERTG  PIWHVY....  LP.......G
Seq.No.4   SQATRIVLYL  YSAGYGVQES  ATYTLSPAGS  GVWAVT....  VPVSSIKAAG
```

Fig. 3(a)

```
              351                                                          400
Seq.No.1   NDLGNVYSNK A.TAFRVWAP TASDVQLLLY NSETGPVTKQ LEMQKSDNGT
Seq.No.2   DDLGNTYTQK A.TTFKVWAP TSTQVNVLLY DSATGSVTKI VPMTASGHGV
Seq.No.3   LRPGQLYGYR VYGPYRP...  .......... .....EEGHR FNPNKVLLDP
Seq.No.4   ITGAVYYGYR AWGPNWPYAS NWGKGSQAGF VSDVDANGDR FNPNKLLLDP 401                                                          450
Seq.No.1   WKLKVPGNLK NWYYLYQVTV NGKTQTAVDP YVRAISVNAT RGMIVDLEDT
Seq.No.2   WEATVNQNLE NWYYMYEVTG QGSTRTAVDP YATAIAPNGT RGMIVDLAKT
Seq.No.3   YAKAIGRPLR WHDSLFGYKI GDPAGDLSFS .EEDSAPYAP LGAVVE....
Seq.No.4   YAQEVSQDPL NPSNQNGNVF ...ASGASYR .TTDSGIYAP KGVVLV....

451                        ----   Loop1                      500
Seq.No.1   NPPGWKEDHQ QTPANPVDEV IYEVHVRDFS .IDANSGMKN KGKYLAFTEH
Seq.No.2   DPAGWNSDKH ITPKNIEDEV IYEMDVRDFS .IDPNSGMKN KGKYLALTEK
Seq.No.3   .GCFEWGDDR PPRIPWEDTI IYETHVKGIT KLHPEVPEPL RGTYLGLT..
Seq.No.4   .PSTQSTGTK PTRAQKDD.V IYEVHVRGFT EQDTSIPAQY RGTYYGAG..

501                        ----   loop2                      550
Seq.No.1   GTKGPDNVKT GIDSLKELGI NAVQLQPIEE FNS.....ID ETQPNMYNWG
Seq.No.2   GTKGPDNVKT GIDSLKQLGI THVQLMPVFA SNS.....VD ETDPTQDNWG
Seq.No.3   .......CEP VLEHLKQLGV TTIQLLPVHA KVHDRHLV.. .ERGLRNYWG
Seq.No.4   .......LKA ..SYLASLGV TAVEFLPVQE TQNDANDVVP NSDANQNYWG 551                                        -------           600
Seq.No.1   YDPRNYNVPE GAYATTPEGT ARITQLKQLI QSIHKDRIAI NMDVVYNHTF
Seq.No.2   YDPRNYDVPE GQYATNANGN ARIKEFKEMV LSLHREHIGV NMDVVYNHTF
Seq.No.3   YNPLCYFAPE PEYATN.GPI SAVREFKMMV RALHAAGFEV IVDVVYNHTG
Seq.No.4   YMTENYFSPD RRYAYNKAAG GPTAEFQAMV QAFHNAGIKV YMDVVYNHTA 601    loop3                                                 650
Seq.No.1   NVGVS..... ......DFDK IVPQYYYRTD SAGN..YTNG SGVGNEIATE
Seq.No.2   ATQIS..... ......DFDK IVPEYYYRTD DAGN..YTNG SGTGNEIAAE
Seq.No.3   EGGVL..... ..GPTLSFRG IDNRAYYKAD PNNPRFLVDY TGTGNTLDVG
Seq.No.4   EGGTWTSSDP TTATIYSWRG LDNATYYELT SGN.QYFYDN TGIGANFNTY 651                        -----  loop4                      700
Seq.No.1   RPMVQKFVLD SVKYWVKEYH IDGFRFDLMA LLGKDTMAKI ..........
Seq.No.2   RPMVQKFIID SLKYWVNEYH IDGFRFDLMA LLGKDTMSKA ..........
Seq.No.3   NPYVIQLIMD SLRYWVTEMH VDGFRFDLAA ALA....... .........R
Seq.No.4   NTVAQNLIVD SLAYWANTMG VDGFRFDLAS VLGNSCLNGA YTASAPNCPN 701                        ----   loop5                      750
Seq.No.1   .......... ..........  .SKELHAINP GIVLYGEPWT GGTSGLSSDQ
Seq.No.2   .......... ..........  .ASELHAINP GIALYGEPWT GGTSALPDDQ
Seq.No.3   ELYDVDMLST FFQV......  ..IQQDPVLS QVKLIAEPWD VGPGGYQVGH
Seq.No.4   GGYNFDAADS NVAINRILRE  FTVRPAAGGS GLDLFAEPWA IGGNSYQLGG
```

Fig. 3(b)

```
          751            ---     loop6                                800
Seq.No.1  LVTKGQQKGL GIGVFNDNIR NGLDGNVFDK SAQGFATGDP NQVNVIKNRV
Seq.No.2  LLTKGAQKGM GVAVFNDNLR NALDGNVFDS SAQGFATGAT GLTDAIKNGV
Seq.No.3  F.......PW QWTEWNGRYR DAV..RRFWR GDRGLN.G.. ....EFATRF
Seq.No.4  F.......PQ GWSEWNGLFR DS.....LRQ AQNELG.SMT IYVIQDANDF 801--     loop7                                             850
Seq.No.1  MGSISDFTSA ...PSETINY VTSHDNMTLW DKISASNPND TQ........
Seq.No.2  EGSINDFTSS ...PGETINY VTSHDNYTLW DKIALSNPND SE........
Seq.No.3  AGSSDLYERS GRRPFASINF VTAHDGFTLE DLVSYTKKHN EANL..EGNR
Seq.No.4  SGSSNLFQSS GRSPWNSINF IDVHDGMTLK DVYSCNGANN SQAWPYGPSD 851                                                ---- 900
Seq.No.1  .......... .......... ...ADRIKMD ELAQAVVFTS QGVPFMQGGE
Seq.No.2  .......... .......... ...ADRIKMD ELAQAVVMTS QGVPFMQGGE
Seq.No.3  DGMDENYSTN CGVEGPTQDP SVLACREALK RSLISTLFLS QGVPMLLGGD
Seq.No.4  GGTSTNYSWD QGMSAGTGAA ..VDQRRAAR TGMAFEM.LS AGTPLMQGGD 901    loop8                                               950
Seq.No.1  EMLRTKGGND NSYNAGDSVN QFDWSRKAQF ENVFDYYSWL IHLRDNHPAF
Seq.No.2  EMLRTKGGND NSYNAGDAVN EFDWSRKAQY PDVFNYYSGL IHLRLDHPAF
Seq.No.3  ELSRTQHGNN NAYCQDNEIS WYNWQLDTRK QQFLEFVRQT IWFRKQHRSF
Seq.No.4  EYLRTLQCNN NAYNLDSSAN WLTYSWTTDQ SNFYTFAQRL IAFRKAHPAL 951                                                    1000
Seq.No.1  R......... .........M TTADQIKQNL TFLDSPTNTV AFELKNHANH
Seq.No.2  R......... .........M TTANEINSHL QFLNSPENTV AYELTDHVNK
Seq.No.3  RRRHFLTGLP NGGRPRRSLV APEGRPMRHE DWTNPELTAF GLLLHGDAIQ
Seq.No.4  RPSSWYSG.. ....SQLTWY QPSGAVADSN YWNNTSNYAI AYAINGPSLG 1001                                                   1050
Seq.No.1  D........K WKNIIVMYNP NKTAQTLTLP SG.......N WTIVGLGNQV
Seq.No.2  D........K WGNIIVVYNP NKTVATINLP SG.......K WAINATSGKV
Seq.No.3  GTDEHGRPFR DDTFLILFNN GSEAVPVVVP EVCSCGKPHH WEVVPVFQRN
Seq.No.4  DS........ .NSIYVAYNG WSSSVTFTLP APPSGT..QW YRVTDTCDWN 1051                                                   1096
Seq.No.1  GEKS...... ....LGHVNG TVEVPALSTI ILHQGTSEDV IDQN..
Seq.No.2  GEST...... ....LGQAEG SVQVPGISMM ILHQEVSPDH GKK...
Seq.No.3  VEPPT..... .....CAPGE TLSLPPGVLT VLVAVPPFSD GNTEPA
Seq.No.4  DGASTFVAPG SETLIGGAGT TYGQCGQSLL LLISK..... ......
```

STARCH DEBRANCHING ENZYMES

CROSS-REFERENCE TO RELATED APPLICATIONS

This application is a continuation of U.S. application Ser. No. 09/833,435, filed on Mar. 26, 2001 (abandoned), which is a continuation of U.S. application Ser. No. 09/346,237, filed Jul. 1, 1999 (now U.S. Pat. No. 6,265,197), which claims priority under 35 U.S.C. 119 of Danish application PA 1998 00868, filed Jul. 2, 1998, and the benefit of U.S. provisional application No. 60/094,353, filed on Jul. 28, 1998, the contents of which are fully incorporated herein by reference.

FIELD OF THE INVENTION

The present invention relates to novel starch debranching enzymes, in particular pullulanases and isoamylases, designed for use in a starch conversion process comprising a liquefaction step and a saccharification step, as well as to the production of such enzymes and the use of such enzymes in a starch conversion process.

BACKGROUND OF THE INVENTION

Starches such as corn, potato, wheat, manioc and rice starch are used as the starting material in commercial large scale production of sugars, such as high fructose syrup, high maltose syrup, maltodextrins, amylose, G4-G6 oligosaccharides and other carbohydrate products such as fat replacers.

Degradation of Starch

Starch usually consists of about 80% amylopectin and 20% amylose. Amylopectin is a branched polysaccharide in which linear chains α-1,4 D-glucose residues are joined by α-1,6 glucosidic linkages. Amylopectin is partially degraded by α-amylase, which hydrolyzes the 1,4-α-glucosidic linkages to produce branched and linear oligosaccharides. Prolonged degradation of amylopectin by α-amylase results in the formation of so-called α-limit dextrins which are not susceptible to further hydrolysis by the α-amylase. Branched oligosaccharides can be hydrolyzed into linear oligosaccharides by a debranching enzyme. The remaining branched oligosaccharides can be depolymerized to D-glucose by glucoamylase, which hydrolyzes linear oligosaccharides into D-glucose.

Amylose is a linear polysaccharide built up of D-glucopyranose units linked together by α-1,4 glucosidic linkages. Amylose is degraded into shorter linear oligosaccharides by α-amylase, the linear oligosaccharides being depolymerized into D-glucose by glucoamylase.

In the case of converting starch into a sugar, the starch is depolymerized. The depolymerization process consists of a pretreatment step and two or three consecutive process steps, namely a liquefaction process, a saccharification process and, depending on the desired end product, optionally an isomerization process.

Pre-Treatment of Native Starch

Native starch consists of microscopic granules which are insoluble in water at room temperature. When an aqueous starch slurry is heated, the granules swell and eventually burst, dispersing the starch molecules into the solution. During this "gelatinization" process there is a dramatic increase in viscosity. As the solids level is 30-40% in a typical industrial process, the starch has to be thinned or "liquefied" so that it can be handled. This reduction in viscosity is today mostly obtained by enzymatic degradation.

Liquefaction

During the liquefaction step, the long-chained starch is degraded into smaller branched and linear units (maltodextrins) by an α-amylase (e.g. Termamyl™, available from Novo Nordisk A/S, Denmark). The liquefaction process is typically carried out at about 105-110° C. for about 5 to 10 minutes followed by about 1-2 hours at about 95° C. The pH generally lies between about 5.5 and 6.2. In order to ensure an optimal enzyme stability under these conditions, calcium is added, e.g. 1 mM of calcium (40 ppm free calcium ions). After this treatment the liquefied starch will have a "dextrose equivalent" (DE) of 10-15.

Saccharification

After the liquefaction process the maltodextrins are converted into dextrose by addition of a glucoamylase (e.g. AMG™, available from Novo Nordisk A/S) and a debranching enzyme, such as an isoamylase (see e.g. U.S. Pat. No. 4,335,208) or a pullulanase (e.g. Promozyme™, available from Novo Nordisk A/S) (see U.S. Pat. No. 4,560,651). Before this step the pH is reduced to a value below 4.5, e.g. about 3.8, maintaining the high temperature (above 95° C.) for a period of e.g. about 30 min. to inactivate the liquefying α-amylase to reduce the formation of short oligosaccharides called "panose precursors" which cannot be hydrolyzed properly by the debranching enzyme.

The temperature is then lowered to 60° C., glucoamylase and debranching enzyme are added, and the saccharification process proceeds for about 24-72 hours.

Normally, when denaturing the α-amylase after the liquefaction step, a small amount of the product comprises panose precursurs which cannot be degraded by pullulanases or AMG. If active amylase from the liquefaction step is present during saccharification (i.e. no denaturing), this level can be as high as 1-2% or even higher, which is highly undesirable as it lowers the saccharification yield significantly. For this reason, it is also preferred that the α-amylase is one which is capable of degrading the starch molecules into long, branched oligosaccharides (such as, e.g., the Fungamyl™-like α-amylases) rather than shorter branched oligosaccharides.

Isomerization

When the desired final sugar product is e.g. high fructose syrup, the dextrose syrup may be converted into fructose by enzymatic isomerization. After the saccharification process the pH is increased to a value in the range of 6-8, preferably about pH 7.5, and the calcium is removed by ion exchange. The dextrose syrup is then converted into high fructose syrup using, e.g., an immobilized glucose isomerase (such as Sweetzyme™, available from Novo Nordisk A/S).

Debranching Enzymes

Debranching enzymes which can attack amylopectin are divided into two classes: isoamylases (E.C. 3.2.1.68) and pullulanases (E.C. 3.2.1.41), respectively. Isoamylase hydrolyses α-1,6-D-glucosidic branch linkages in amylopectin and β-limit dextrins and can be distinguished from pullulanases by the inability of isoamylase to attack pullulan, and by their limited action on α-limit dextrins.

When an acidic stabilised "Termamyl™-like" α-amylase is used for the purpose of maintaining the amylase activity during the entire saccharification process (no inactivation), the degradation specificity should be taken into consideration. It is desirable in this regard to maintain the α-amylase activity throughout the saccharification process, since this allows a reduction in the amyloglucidase addition, which is economically beneficial and reduces the AMG™ condensation product isomaltose, thereby increasing the DE (dextrose equivalent) yield.

It will be apparent from the above discussion that the known starch conversion processes are performed in a series of steps, due to the different requirements of the various enzymes in terms of e.g. temperature and pH. It would therefore be desirable to be able to engineer one or more of these enzymes so that the overall process could be performed in a more economical and efficient manner. One possibility in this regard is to engineer the otherwise thermolabile debranching enzymes so as to render them more stable at higher temperatures. The present invention relates to such thermostable debranching enzymes, the use of which provides a number of important advantages which will be discussed in detail below. It also relates to starch debranching enzymes with an altered substrate specificity.

SUMMARY OF THE INVENTION

An object of the present invention is thus to provide thermostable debranching enzymes, for example pullulanases and isoamylases, which are suitable for use at high temperatures in a starch conversion process, in particular using genetic engineering techniques in order to identify and synthesize suitable enzyme variants. Another object of the invention is to provide novel starch debranching enzymes with an altered substrate specificity.

In its broadest aspect, the present invention can thus be characterized as relating to novel starch debranching enzymes with improved properties in terms of e.g. thermostability or substrate specificity, as well as methods for producing such enzymes and the use of such enzymes in a starch conversion process.

In one particular aspect, the invention relates to a genetically engineered variant of a parent starch debranching enzyme, the enzyme variant having an improved thermostability at a pH in the range of 4-6 compared to the parent enzyme.

Another aspect of the invention relates to a genetically engineered variant of a parent starch debranching enzyme, the enzyme variant having an increased activity towards amylopectin and/or glycogen compared to the parent enzyme.

A further aspect of the invention relates to a method for producing a starch debranching enzyme variant with increased thermostability, the method comprising the steps of:

identifying one or more amino acid residues and/or amino acid regions associated with thermostability in a first parent starch debranching enzyme, identifying one or more homologous amino acid residues and/or amino acid regions in a second parent starch debranching enzyme by means of alignment of the amino acid sequences of the first and second parent starch debranching enzymes, and mutating one or more of the homologous amino acid residues and/or amino acid regions in the second parent starch debranching enzyme to produce an enzyme variant with increased thermostability.

A still further aspect of the invention relates to a method for producing a starch debranching enzyme variant with altered substrate specificity, the method comprising the steps of:

identifying one or more amino acid residues in at least one amino acid loop associated with specificity towards a desired substrate in a first parent starch debranching enzyme, identifying one or more homologous amino acid residues in at least one corresponding loop in a second parent starch debranching enzyme by means of alignment of the amino acid sequences of the first and second parent starch debranching enzymes, and mutating one or more of the homologous amino acid residues in at least one loop in the second parent starch debranching enzyme to produce an enzyme variant with altered substrate specificity.

The term "loop" means, at least in the context of the present invention, the sequence part following the beta-strand/sheet part of the sequence in question. Said "beta strands/sheets" may be identified by multiple sequence alignment of sequences of the present invention and sequences with a known three dimensional structure. Such alignments can be made using standard alignment programs, available from e.g. the UWGCG package (Program Manual for the Wisconsin Package, Version 8, August 1994, Genetics Computer Group, 575 Science Drive, Madison, Wis., USA 53711).

Known three-dimensional enzyme structures are available from Brookhaven Databank. Examples of such are the three-dimensional structure of the *Aspergillus oryzae* TAKA α-amylase (Swift et al., 1991), the *Aspergillus niger* acid amylase (Brady et al, 1991), the structure of pig pancreatic α-amylase (Qian et al., 1993), and the barley α-amylase (Kadziola et al. 1994, Journal of Molecular Biology 239: 104-121; A. Kadziola, Thesis, Dept of Chemistry, U. of Copenhagen, Denmark).

The invention relates in addition to a method for converting starch to one or more sugars, the method comprising debranching the starch using at least one enzyme variant as described herein.

BRIEF DESCRIPTION of DRAWINGS

FIG. 1 shows the amino acid sequence of four different pullulanases (SEQ ID NO 5, 6, 1 and 2) as well as an alignment of these sequences.

FIG. 2 shows the amino acid sequence of seven different isoamylases (SEQ ID NO 4, 7, 8, 9, 10, 3 and 11) as well as an alignment of these sequences.

FIG. 3 shows a "key alignment" of selected pullulanases and isoamylases (those of SEQ ID NO 1,2,3 and 4).

DETAILED DESCRIPTION OF THE INVENTION

In the present context, the term "thermostable" refers in general to the fact that the debranching enzyme variants according to the invention have an improved thermostability compared to the relevant parent enzyme. The degree of improvement in thermostability can vary according to factors such as the thermostability of the parent enzyme and the intended use of the enzyme variant, i.e. whether it is primarily intended to be used in for liquefaction or for saccharification or both. It will be apparent from the discussion below that for saccharification, the enzyme variant should maintain a substantial degree of enzyme activity during the saccharification step at a temperature of at least about 63° C., preferably at least about 70° C., while an enzyme variant designed for use in the liquefaction step should be able to maintain a substantial degree of enzyme activity at a temperature of at least about 95° C.

The improved thermostability of enzyme variants according to the invention can in particular be defined according to one or more of the following criteria:

In one embodiment, the enzyme variant of the invention has an improved thermostability as defined by differential scanning calorimetry (DSC) using the method described below.

In another embodiment, the enzyme variant of the invention has an improved thermostability as defined by an increased half-time ($T_{1/2}$) of at least about 5%, preferably at least about 10%, more preferably at least about 15%, more preferably at least about 25%, most preferably at least about 50%, such as at least 100%, in the "$T_{1/2}$ assay for liquefaction" described herein, using a pH of 5.0 and a temperature of 95° C. Enzyme variants according to this definition are suitable for use in the liquefaction step of the starch conversion process.

Alternatively or additionally, an enzyme variant suitable for use in liquefaction can be defined as having an improved thermostability as defined by an increased residual enzyme activity of at least about 5%, preferably at least about 10%, more preferably at least about 15%, more preferably at least about 25%, most preferably at least about 50%, in the "assay for residual activity after liquefaction" described herein, using a pH of 5.0 and a temperature of 95° C.

In a further embodiment, the enzyme variant of the invention has an improved thermostability as defined by an increased half-time ($T_{1/2}$) of at least about 5%, preferably at least about 10%, more preferably at least about 15%, more preferably at least about 25%, most preferably at least about 50%, such as at least 100%, in the "$T_{1/2}$ assay for saccharification" described herein, using a pH of 4.5 and a temperature of 70° C. Such variants are suitable for use in the saccharification step of the starch conversion process.

Alternatively or additionally, an enzyme variant suitable for saccharification can be defined as having an improved thermostability as defined by an increased residual enzyme activity of at least about 5%, preferably at least about 10%, more preferably at least about 15%, more preferably at least about 25%, most preferably at least about 50%, in the "assay for residual activity after saccharification" described herein, using a pH of 4.5 and a temperature of 63° C. Preferably, this improved thermostability is also observed when assayed at a temperature of 70° C.

The term "substantially active" as used herein for a given enzyme variant and a given set of conditions of temperature, pH and time means that the relative enzymatic activity of the enzyme variant is at least about 25%, preferably at least about 50%, in particular at least about 60%, especially at least about 70%, such as at least about 90% or 95%, e.g. at least about 99% compared to the relative activity of the parent enzyme under the given set of conditions mentioned in connection with improved thermostability right above.

An enzyme variant "derived from" a given enzyme (a "parent enzyme") means that the amino acid sequence of the parent enzyme has been modified, i.e. by substitution, deletion, insertion and/or loop transfer as described below, to result in the enzyme variant. In the case of a parent enzyme produced by an organism such as a microorganism, where an enzyme variant according to the invention is derived from the parent enzyme, the enzyme variant may be produced by appropriate transformation of the same or a similar microorganism or other organism used to produce the parent enzyme.

One advantage of the thermostable debranching enzymes of the invention is that they make it possible to perform liquefaction and debranching simultaneously before the saccharification step. This has not previously been possible, since the known pullulanases and isoamylases with acceptable specific activity are thermolabile and are inactivated at temperatures above 60° C. (Some thermostable pullulanases from *Pyrococcus* are known, but these have an extremely low specific activity at higher temperatures and are thus unsuitable for purposes of the present invention). By debranching, using the thermostable debranching enzymes of the invention, during liquefaction together with the action of an α-amylase, the formation of panose precursors is reduced, thereby reducing the panose content in the final product and increasing the overall saccharification yield. It is also possible in this manner to extend the liquefaction process time without risking formation of large amount of panose precursors. By prolonging the liquefaction step, the DE yield is increased from 10-15 to e.g. 15-20, reducing the need for glucoamylase. This reduced glucoamylase requirement is in turn advantageous as the formation of undesired isomaltose is reduced, thereby resulting in an increased glucose yield. In addition, the reduced glucoamylase addition enables the saccharification step to be carried out at a higher substrate concentration (higher DS, dry substances, concentration) than the normal approx. 30-35% used according to the prior art. This allows reduced evaporation costs downstream, e.g. in a high fructose corn syrup process, and the saccharification reaction time can also be reduced, thereby increasing production capacity. A further advantage is that α-amylase used in the liquefaction process does not need to be inactivated/denatured in this case.

Furthermore, it is also possible to use the thermostable debranching enzymes according to the invention during saccharification, which is advantageous for several reasons. In the conventional starch saccharification process, the process temperature is not more than 60° C. due to the fact that neither the saccharification enzyme pullulanase nor AMG™ are sufficiently thermostable to allow the use of a higher temperature. This is a disadvantage, however, as it would be very desirable to run the process at a temperature of above about 60° C., in particular above 63° C., e.g. about 70° C., to reduce microbial growth during the relatively long saccharification step. Furthermore, a higher process temperature normally gives a higher activity per mg of enzyme (higher specific activity), thereby making it possible to reduce the weight amount of enzyme used and/or obtain a higher total enzymatic activity. A higher temperature can also result in a higher dry matter content after saccharification, which would be beneficial in terms of reducing evaporation costs.

Although a thermostable isoamylase might be regarded as being more beneficial than a thermostable pullulanase when used in the liquefaction process, since isoamylases are characterised by their specificity towards amylopectin and activity on higher molecular weight dextrins, a preferred alternative is to alter the specificity of a pullulanase so as to be more "isoamylase-like" in the sense of having improved activity towards longer, branched-chain dextrins. Among the various pullulanases there are substantial differences in this respect, even among the pullanases of the same *Bacillus* origin.

Methods for Determining Stability and Activity

Thermostability

Thermostability of pullulanases and isoamylases can be detected by measuring the residual activity by incubating the enzyme under accelerated stress conditions, which comprise: pH 4.5 in a 50 mM sodium acetate buffer without a stabilizing dextrin matrix (such as the approximately 35% dry matter which is normally present during saccharification). The stability can be determined at isotherms of e.g. 63° C., 70° C., 80° C., 90° C. and 95° C., measuring the residual activity of samples taken from a water bath at regular intervals (e.g. every 5 or 10 min.) during a time period of 1 hour. For determining stability for the purpose of liquefaction, a pH of 5.0, a temperature of 95° C. and a total assay time of 30 minutes are used ("assay for residual activity after liquefaction"). For determining stability for the purpose of saccharification, a pH of 4.5, a temperature of 63° C. or 70° C. and a total assay time of 30 minutes are used ("assay for residual activity after saccharification").

Alternatively, the thermostability may be expressed as a "half-time" ($T_{1/2}$), which is defined as the time, under a given set of conditions, at which the activity of the enzyme being assayed is reduced to 50% of the initial activity at the beginning of the assay. In this case, the "$T_{1/2}$ assay for liquefaction" uses a pH of 5.0 and a temperature of 95° C., while the "$T_{1/2}$ assay for saccharification" uses a pH of 4.5 and a temperature of 70° C. The assay is otherwise performed as described above for the respective assays for residual activity.

Activity: Somogyi-Nelson Method for Determination of Reducing Sugars

The activity of both pullulanases and isoamylases can be measured using the Somogyi-Nelson method for the determination of reducing sugars (J. Biol. Chem. 153, 375 (1944)). This method is based on the principle that sugar reduces cupric ions to cuprous oxide, which reacts with an arsenate molybdate reagent to produce a blue colour that is measured spectrophotometrically. The solution to be measured must contain 50-600 mg of glucose per litre. The procedure for the Somogyi-Nelson method is as follows:

Sample value: Pipet 1 ml of sugar solution into a test tube. Add 1 ml of copper reagent. Stopper the test tube with a glass bead. Place the test tube in a boiling water bath for 20 minutes. Cool the test tube. Add 1 ml of Nelson's colour reagent. Shake the test tube without inverting it. Add 10 ml of deionized water.

Invert the test tube and shake vigorously. Measure the absorbance at 520 nm, inverting the test tube once immediately prior to transfer of the liquid to the cuvette.

Blank value: Same procedure as for the sample value, but with water instead of sugar solution.

Standard value: Same procedure as for the sample value.

Calculations:

In the region 0-2 the absorbance is proportional to the amount of sugar.

$$\text{mg sugar/l} = \frac{100 \text{ (sample} - \text{blank)}}{\text{(standard} - \text{blank)}}$$

$$\% \text{ glucose} = \frac{\text{(sample} - \text{blank)}}{100 \times \text{(standard} - \text{blank)}}$$

Reagents:

1. Somogyi's Copper Reagent 35.1 g $Na_2HPO_4.2H_2O$ and 40.0 g potassium sodium tartrate ($KNaC_4H_4O_2.4H_2O$) are dissolved in 700 ml of deionized water. 100 ml of 1N sodium hydroxide and 80 ml of 10% cupric sulphate ($CuSO_4.5H_2O$) are added. 180 g of anhydrous sodium sulphate are dissolved in the mixture, and the volume is brought to 1 litre with deionized water.

2. Nelson's Colour Reagent 50 g of ammonium molybdate are dissolved in 900 ml of deionized water. Then 42 ml of concentrated sulphuric acid are added, followed by 6 g of disodium hydrogen arsenate heptahydrate dissolved in 50 ml of deionized water, and the volume is brought to 1 litre with deionized water. The solution is allowed to stand for 24-48 hours at 37° C. before use and is stored in the dark in a brown glass bottle with a glass stopper.

3. Standard 100 mg of glucose (anhydrous) are dissolved in 1 litre of deionized water.

Substrate Specificity

Methods for the determination and characterisation of the profile of action and specificity of pullulanases and isoamylases for various substrates (e.g. amylopectin, glycogen and pullulan) are described by Kainuma et al. in *Carbohydrate Research*, 61 (1978) 345-357. Using these methods, the relative activity of an isoamylase or a pullulanase can be determined, and the relative activity of an enzyme variant according to the invention compared to the relative activity of the parent enzyme can be assessed, for example to determine whether a pullulanase variant has the desired increased specificity toward high molecular weight saccharides such as amylopectin compared to the parent enzyme.

Starch Conversion

As indicated above, in one embodiment of the invention, the starch conversion process comprises debranching using a thermostable debranching enzyme of the invention during the liquefaction step together with an α-amylase. The liquefaction step is typically carried out at a pH between 4.5 and 6.5, e.g. from 5.0 to 6.2, at a temperature in the range of 95-110° C. for a period of 1 to 3 hours, preferably about 1.5-2 hours. It is preferred, however, that the pH is as low as possible, e.g. from 4.5 to 5.0, as long as the enzyme(s) used for the liquefaction have a sufficient stability at the pH in question. If the α-amylase is calcium dependent, calcium may be added in an amount of from 30 to 50 ppm, such as around 40 ppm (or 0.75 to 1.25 mM, such as around 1 mM) in the liquefaction step to stabilise the enzyme. As explained above, the the α-amylase need not be inactivated after the liquefaction step to reduced the panose formation in this case.

Examples of specific α-amylases which can be used in the liquefaction step include *Bacillus licheniformis* α-amylases, such as the commercially available products Termamyl®, Spezyme® AA, Spezyme® Delta AA, Maxamyl® and Kleistase®, and the α-amylase mutants described in WO 96/23874 (Novo Nordisk) and PCT/DK97/00197 (Novo Nordisk).

Isoamylases which can be used as a parent enzyme according to the invention include, but are not limited to, the thermostable isoamylase derived from the thermophilic acrhaebacterium *Sulfolobus acidocaldarius* (Maruta, K et al., (1996), Biochimica et *Biophysica Acta* 1291, p. 177-181), isoamylase from *Rhodothermus marinus* (e.g. the isoamylase of SEQ ID NO 3) and isoamylase from *Pseudomonas*, e.g. *Pseudomonas amyloderamosa* (e.g. *Pseudomonas amyloderamosa* isoamylase disclosed in EMBL database accession number J03871 or GeneBank accession number N90389).

Examples of pullulanases which can be used as a parent enzyme include, but are not limited to, a thermostable pullulanase from e.g. *Pyrococcus* or a protein engineered pullulanase from e.g. a *Bacillus* strain such as *Bacillus acidopullulyticus* (e.g. Promozyme™ or SEQ ID NO 1) or

*Bacillus deramificans* (e.g. SEQ ID NO 2; or the *Bacillus deramificans* pullulanase with GeneBank accession number Q68699).

While prior art methods for saccharification employ a temperature of not more than about 60° C., the present invention provides thermostable debranching enzymes that can remain active at higher temperatures, i.e. at least about 63° C. and preferably at least about 70° C. so as to eliminate possibilities for microbial growth. Examples of suitable glycoamylases for saccharification include *Aspergillus niger* glucoamylases, such as AMG™. The saccharification process typically proceeds for about 24-72 hours at a pH of about 4.0-4.5, preferably about 4.0.

When the desired final sugar product is e.g. a high fructose syrup of approx. 50% fructose syrup, the formed D-glucose is isomerized by an isomerase at a pH around 6-8, preferably about 7.5. An example of a suitable isomerase is an glucose isomerase such as the glucose isomerase derived from *Streptomyces murinus*. The isomerase may be an immobilized glucose isomerase, such as Sweetzyme®.

Calcium is normally removed if added before the liquefaction step.

Engineering of Pullulanases and Isoamylases

The pullulanases and isoamylases are members of the family 13 amylases (Henrissat, B. et al., *Biochem J*. 293: 781-788, 1993). This suggests that they have the same overall structure in the central part of the molecule consisting of an A, B and C domain. The B domains vary quite dramatically in size and structure, whereas the other two domains are believed to generally possess a high degree of homology. The A domain is composed of an alpha-8/beta-8 structure (a beta-barrel) and 8 loops between the beta-strands and the alpha-helices (a helix can in certain cases be absent, however). The sequences coming from the beta-strand part of the beta-barrel point towards the substrate binding region. These regions are of particular interest for the specificity of the enzyme (Svensson, B. et al., *Biochemical Society Transactions*, Vol. 20; McGregor, *J. Prot. Chem.* 7:399, 1988). However, by using information about specific sequences and as well as general strategies for analyzing pullulanase and isoamylase sequences, the present invention provides the necessary tools to be able to engineer these enzymes to produce variants with improved thermostability and/or specificity.

Sequence Listings

The following sequence listings are referred to herein:

SEQ ID NO 1: pullulanase from *Bacillus acidopullulyticus*

SEQ ID NO 2: pullulanase from *Bacillus deramificans*

SEQ ID NO 3+SEQ ID NO 12: isoamylase from *Rhodothermus marinus*

SEQ ID NO 4: isoamylase from *Pseudomonas amyloderamosa* JD270 (Chen, J H et al. (1990) Biochemica et Biophysica Acta 1087, pp 307-315) (Brookhaven database: 1BF2)

SEQ ID NO 5: pullulanase from *Klebsiella pneumoniae* (Kornacker et al., Mol. Microbiol. 4:73-85(1990))

SEQ ID NO 6: pullulanase from *Klebsiella aerogenes* (Katsuragi et al., J. Bacteriol. 169:2301-2306 (1987))

SEQ ID NO 7: isoamylase from *Pseudomonas* sp. SMP1 (Tognoni, A. et al., U.S. Pat. No. 5,457,037)

SEQ ID NO 8: isoamylase from *Favobacterium odoratum* (JP 9623981, Susumu Hizukuri et al.)

SEQ ID NO 9: isoamylase from *Sulfolobus acidocaldarius*, ATCC 33909 (Biochimica et Biophysica Acta 1291 (1996) 177-181, Kazuhiko Maruta et al.)

SEQ ID NO 10: isoamylase from *Sulfolobus solfataricus* (GeneBank Accession no. Y08256).

SEQ ID NO 11: isoamylase from maize, *Zea mays* (ACCESSION U18908)

SEQ ID NO 13: *Bacillus acidopullulyticus* pulB gene (SEQ ID NO: 13).

Structure of Pullulanases

The appended FIG. 1 shows the amino acid sequence of four different pullulanases as well as an alignment of these sequences. On the basis of information provided by this alignment, it is possible to perform homology substitutions in order to obtain desired characteristics of improved thermostability and/or altered substrate specificity.

The four sequences are SEQ ID NO 5, 6, 1 and 2.

Structure of Isoamylases

The appended FIG. 2 shows the amino acid sequence of seven different isoamylases as well as an alignment of these sequences. On the basis of information provided by this alignment, it is possible to perform homology substitutions in order to obtain desired characteristics of improved thermostability and/or altered substrate specificity.

The seven sequences are SEQ ID NO 4, 7, 8, 9, 10, 3 and 11.

The X-ray structure of the *Pseudomonas amyloderamosa* isoamylase has recently been published in the Brookhaven database under number 1BF2. The structure confirms the overall view of the sequence alignment method, but also shows certain differences to the suggested alignment. The corrected loop numbers deduced from the 3D structure of *Pseudomonas amyloderamosa* isoamylase (1BF2) are shown below:

| Alignment of pullulanases and isoamylases | | |
|---|---|---|
| Loop | Suggested | Deduced from structure |
| 1. | 210-230 | 211-231 |
| 2. | 250-292 | 251-295 |
| 3. | 319-376 | 319-330 |
| 4. | 401-436 | 401-436 |
| 5. | 461-479 | 461-468 |
| 6. | 482-485 | 482-503 |
| 7. | 530-539 | 533-580 |
| 8. | 605-636 | 606-636 |

The appended FIG. 3 shows a "key alignment" of selected pullulanases and isoamylases (those of SEQ ID NO 1, 2, 3 and 4), in other words a best-fit alignment of homologous amino acid residues in the respective sequences. The dashes ("- - - -") indicate presumed beta-strand positions. Each set of dashes is followed by a loop number, indicating the position in the sequence of the loops. Information on the location of the individual loops is found in Table 1 below.

By comparing the most homologous sequence from the "key alignment" of two or more relevant starch debranching enzymes with a new starch debranching enzyme sequence, and aligning these two sequences, residues from the new sequence homologous to residues in the sequence from the key alignment can be determined. The homology may be found e.g. by using the GAP program from the UWGCG package (Program Manual for the Wisconsin Package, Version 8, August 1994, Genetics Computer Group, 575 Science Drive, Madison, Wis., USA 53711). The new sequence can then be placed in the key alignment by using a text editing program or other suitable computer program.

Table 1 below provides information on the location of selected regions of interest in the various loops of the selected pullulanases and isoamylases, these loop regions being of general interest with regard to modification to produce enzyme variants according to the invention. Loop 3 below constitutes domain B (MacGregor, 1988), while the other loops belong to domain A.

TABLE 1

|  |  | Loop 1 | Loop 2 | Loop 3 | Loop 4 | Loop 5 | Loop 6 | Loop 7 | Loop 8 |
|---|---|---|---|---|---|---|---|---|---|
| Pullulanases |  |  |  |  |  |  |  |  |  |
| Seq. Id. No. 1 | a. | 369–397 | 419–458 | 484–525 | 553–568 | 582–608 | 613–616 | 661–670 | 708–739 |
|  | b. | 372–385 | 422–448 | 488–520 | 558–568 | 587–606 |  | 663–670 | 710–724 |
|  | c. | 375–385 | 422–438 | 488–499 |  | 591–606 |  |  | 710–715 |
| Seq. Id. No. 2 | a. | 465–493 | 515–554 | 580–621 | 649–664 | 680–711 | 714–717 | 757–765 | 804–834 |
| Isoamylases |  |  |  |  |  |  |  |  |  |
| Seq. Id. No. 4 | a. | 210–230 | 250–292 | 319–376 | 401–437 | 461–479 | 482–485 | 530–539 | 605–636 |
| Seq. Id. No. 3 | a. | 176–195 | 218–257 | 283–334 | 359–381 | 395–413 | 416–419 | 461–470 | 537–568 |
|  | b. | 179–193 | 221–250 | 288–326 | 364–381 | 399–411 |  | 463–470 | 539–553 |
|  | c. | 182–193 | 221–239 | 288–303 |  | 403–411 |  |  | 539–545 |

Where more than one region is listed for a given enzyme and loop in Table 1, the region listed first (i.e. a.) is in each case the expected length of the loop in question. The next region (i.e. b.) is the preferred region for modification, and the last region (i.e. c.) is most preferred.

By performing modifications, i.e. substitutions, deletions, insertions and/or loop transfer, in one or more these loops, engineered proteins having the desired properties in terms of improved thermostability and/or altered substrate specificity may be produced. An enzyme variant according to the invention may comprise any appropriate combination of one or more substitutions, deletions, insertions and/or loop transfers to obtain the desired characteristics of improved thermostability and/or altered activity.

The loop region of SEQ ID NO: 1, i.e. 369-397 (region denoted a), may according to the invention suitably be replaced with the corresponding spatially placed region of SEQ ID NO.4, i.e. 176-195 (i.e. denoted a.). Further, region 371-385 of loop 1 (SEQ ID NO: 1) (i.e. denoted b.) may correspondingly be replaced with region 179-193 of loop 1 (SEQ ID NO. 4) (i.e. denoted b.).

In the present context, a simplified nomenclature is used to indicate amino acid substitutions in a given position. For example "G81P" refers to the substitution of a glycine residue in position 81 with a proline residue, and "F489G,A" refers to the substitution of a phenylalanine residue in position 489 with either glycine or alanine.

Engineering for Improved Thermostability

When engineering for improved thermostability, either or both of the first and second parent enzymes may be an isoamylase or a pullulanase. For obtaining improved thermostability of isoamylases and pullulanases, we can focus especially on the B domain, which has been shown to be important for stability, using sequence homology information as further described below.

Thermostability—Sequence Homology

Several different approaches may be used for the purpose of obtaining increased thermostability, including proline substitutions, Gly to Ala substitutions and Asn and Gln substitutions. Further details and examples of these approaches are provided below.

Proline Substitutions:

Proline substitutions, i.e. replacing one or more non-proline amino acid residues with a proline residue, are suggested as an approach for obtaining thermostability on the basis of sequence alignment of isomylases and pullulanases. Examples of possible proline substitutions are provided in the following.

Isoamylases:
In *P. amyloderamosa* isomylase (SEQ ID NO 4):
Positions for proline substitution include G81P, G99P, T18P, T199P, Q202P, T221, Q226P, A238P, T278P, R286P, A294P, G467P, G64P, V67P, E69P, A549P, G713P, T719P and D736P, and preferably S356P, T376P, T278P, N348P and S454P.

In *R. marinus* isoamylase (SEQ ID NO 3):
Positions for proline substitution include G154P, $N_{305}P$ and N669P, and preferably R588P and K480P.

Pullulanases:
In *B. acidopullulyticus* pullulanase (SEQ ID NO 1):
Preferred positions include A210P, V215P, L249P, K383P, S509P, T811P and G823P. in *B. deramificans* pullulanase (SEQ ID NO 2):
Preferred positions include G306P, V311P, L345P, D605P, T907P and A919P.

Gly to Ala substitutions: for example:
In *P. amyloderamosa* isoamylase (SEQ ID NO 4): G181A
Asn (N) and Gln (O) substitutions:
The new residues are chosen from all 20 possible amino acid residues, but preferably residues in a homologous position as seen from sequence alignment, Leu, Ile, Phe, Ala, Thr, Ser and Tyr being preferred. Of special interest are the following:

SEQ ID NO 1:
Loop1: N379, N384
Loop2: N426, Q432, N434, N437, N444, N446
Loop3: N486, N490, Q502, N512, N515, N521
Loop4:
Loop5: Q596
Loop6: N616, N621, Q628
Loop7: N679, N681, Q684
Loop8: N720, N722, N731, Q732

SEQ ID NO 2:
Loop1: N475, N480
Loop2: N522, N533, N590
Loop3: N582, $N_{6048}$, N611, N617
Loop4:
Loop5: Q691, Q698
Loop6: N712, N717
Loop7: N764, N775
Loop8: N815, N817, N820

SEQ ID NO 3:
Loop1:
Loop2: N227, N232
Loop3: N286, N$_{305}$, N314, N315, N327, N333
Loop4:
Loop5: Q405
Loop6:
Loop7: N482, N485, N489, N496, N500, Q513
Loop8: N54, N548, N549, Q553, N555, N560, Q562

SEQ ID NO 4:
Loop1: Q218, Q225
Loop2: Q254, Q257, N258, N261, N266, N270, Q271, N272, N280
Loop3: N322, N348, N358, Q359, N364, N370, N372, N375
Loop4: N$_{408}$, N412, N421, N424, N428
Loop5: N468, Q471, Q477
Loop6:
Loop7: N547, N550, N551, Q553, N567, Q572
Loop8: Q615, N617, N618, N619, N622

Modifications in loops 2 and 3 are of particular interest with regard to improving thermostability. Loop 2 is of interest due to its interactions with another domain in the N-terminal part of the sequence. Loop 3 is of interest due to possible association with a calcium binding site located between domain A and domain B.

Engineering for Altered Substrate Specificity

When engineering for altered substrate specificity, either or both of the first and second parent enzymes may be an isoamylase or a pullulanase, although it is of particular interest for purposes of the present invention to obtain improved specificity of pullulanases towards higher molecular weight branched starchy material such as glycogen and amylopectin, in other words a transfer of "isoamylase-like" specificity to a pullulanase, e.g. by means of modifications in the loops 1-8, preferably loops 1, 2, 4 and 5.

For the transfer of isoamylase-like activity to pullulanase, a loop transfer from an isoamylase to a pullulanase is of particular interest, for example by inserting loop 5 from an isoamylase into the site for loop 5 of a pullulanase, or by inserting loop 1 from an isoamylase into the site for loop 1 of a pullulanase with the numbering indicated in Table 1.

Activity, Sequence Homology and Overall Beta-Strand, Alpha-Helix and Loop Placement in Sequence Knowledge Activity, either specific activity or specificity, can be transferred to pullulanases, using sequence information from e.g. P. amyloderamosa isoamylase (SEQ ID NO: 4) (high isoamylase activity). Also activity, either specific activity or specificity, can be transferred to isoamylases, using sequence information from e.g. B. acidopullulyticus pullulanase (SEQ ID NO: 1). The loops are analysed for specific residues present especially in the beginning of the loop sequence, from the end of the beta-strand in isoamylases (or suggested beta-strand in pullulanases).

The suggested changes exemplified below apply to all pullulanases in the homologous positions corresponding to those of the two pullulanases discussed:

Providing pullulanase with isoamylase-like activity: This may be provided by substitutions in loop regions following the beta-strands in B. acidopullulyticus (SEQ ID NO 1) and B. deramificans (SEQ ID NO 2) pullulanase:

| After strand: | Beta-1 | Beta-2 | Beta-3 | Beta-4 | Beta-5 | Beta-6 | Beta-7 | Beta-8 |
|---|---|---|---|---|---|---|---|---|
| B. acido. Seq. ID. No. 1 | D137G | N437Y | F489G,A | M555A | G581A T585A,D | I614Y,F | N668G W672EKQA | E711D |
| B. derami. Seq. ID. No. 2 | D149G | N533Y | F585G,A | M651A | G677A T681A,D | L710Y,F | N764G W768EKQA | E807D |

For transfer of the high activity of P. amyloderamosa isoamylase towards higher molecular weight branched starchy material to R. marinus isoamylase or other isoamylases, or to pullulanases, a sequence alignment is performed as described above. By assessing sequence homology and taking into consideration the "structure" of the enzymes as described above, strategies for mutation can be deduced.

The transfer of higher activity from P. amyloderamosa is preferably performed without losing the thermostability of R. marinus isoamylase in any substantial degree. Although it may generally be difficult to alter substrate activity without altering thermostability, it is contemplated that the present invention will allow the obtainment of a higher activity while at the same time substantially maintaining the high thermostability in R. marinus isoamylase as well as in the more thermostable pullulanases. This is made possible by aligning isoamylases and pullulanases to be mutated with the "key alignment" and selecting parent enzymes to be mutated as well as specific amino acid residues and regions to be mutated using information obtained from such alignments of amino acid sequences.

The list below provides examples of possible mutations, based on these principles, that may be performed to obtain higher activity of R. marinus (SEQ ID NO 3) towards the higher molecular weight starchy materials.

Mutations for Higher Activity of SEQ ID NO 3:
Loop1: K183E, L184Q, H185D, P186T, E187S, V188I, E190A, P191Q
Preferred; L184Q, P186T, E187S, P191Q
Loop2: H222Q, A223E, K224T, V225Q, H226N, R228A, H229N, L230D, insert VPN between 231 and 232, E232S, R233D, G234A, L235N, R236Q, N242M, P243T, L244E, C245N, A248S, E250D, P251R
Preferred; K224T, V225Q, R228A, P251R
Loop3: G289A, V293T, L294W, insertion of TSSDPTT between 294 and 295, G295A, P296T, T297I, L298Y, F300W, I303L, R306A, A307T, K310E, A311L, D312T, P313S, N314G, delete P316, R317Q, F318Y, L319F, V320Y, Y322N, T325I, N327A, T328N, L329F, D330N, V331T, G332Y, P334T
Preferred; P296T, R306A, P313S, delete P316, V331T, P334T
Loop4: A404S, A405V, A407G
Loop5: D397A, V398I, P400G, G401N, G402S, V405L, H407G, W410Q, Q411G
Loop6: R418L, Y419F, A422S, V423L, R425Q, F426A, W427Q Loop7: F469M, E472K, L474V, V475Y
Loop8: L542Y, S543L, Q5446L, H447Q Site-Directed Mutagenesis Once an isoamylase or pullulanase encoding DNA sequence has been isolated, and desirable sites for mutation identified, mutations may be introduced using synthetic oligonucleotides. These oligonucleotides contain nucleotide sequences flanking the desired mutation sites. In a specific method, a single-stranded gap of DNA, the enzyme-encoding sequence, is created in a vector carrying the enzyme gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al., (1984), Biotechnology 2, p. 646-639. U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method for introducing mutations into enzyme-encoding DNA sequences is described in Nelson and Long, (1989), Analytical Biochemistry 180, p. 147-151. It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Random Mutagenesis

Random mutagenesis is suitably performed either as localised or region-specific random mutagenesis in at least three parts of the gene translating to the amino acid sequence shown in question, or within the whole gene.

The random mutagenesis of a DNA sequence encoding a parent enzyme may be conveniently performed by use of any method known in the art.

In relation to the above, a further aspect of the present invention relates to a method for generating a variant of a parent enzyme, wherein the variant exhibits improved thermal stability relative to the parent, the method comprising:

(a) subjecting a DNA sequence encoding the parent enzyme to random mutagenesis,
(b) expressing the mutated DNA sequence obtained in step (a) in a host cell, and
(c) screening for host cells expressing an enzyme variant which has an altered property (e.g. thermal stability) relative to the parent enzyme.

Step (a) of the above method of the invention is preferably performed using doped primers.

For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents. The mutagenizing agent may, e.g., be one which induces transitions, transversions, inversions, scrambling, deletions, and/or insertions.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues. When such agents are used, the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties.

When the mutagenesis is performed by the use of an oligonucleotide, the oligonucleotide may be doped or spiked with the three non-parent nucleotides during the synthesis of the oligonucleotide at the positions which are to be changed. The doping or spiking may be done so that codons for unwanted amino acids are avoided. The doped or spiked oligonucleotide can be incorporated into the DNA encoding the glucoamylase enzyme by any published technique, using e.g. PCR, LCR or any DNA polymerase and ligase as deemed appropriate.

Preferably, the doping is carried out using "constant random doping", in which the percentage of wild-type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints. The doping scheme may be made by using the DOPE program which, inter alia, ensures that introduction of stop codons is avoided (Jensen, L J, Andersen, K V, Svendsen, A, and Kretzschmar, T (1998) Nucleic Acids Research 26:697-702).

When PCR-generated mutagenesis is used, either a chemically treated or non-treated gene encoding a parent glucoamylase is subjected to PCR under conditions that increase the mis-incorporation of nucleotides (Deshler 1992; Leung et al., Technique, Vol. 1, 1989, pp. 11-15).

A mutator strain of E. coli (Fowler et al., Molec. Gen. Genet., 133, 1974, pp. 179-191), S. cereviseae or any other microbial organism may be used for the random mutagenesis of the DNA encoding the enzyme by, e.g., transforming a plasmid containing the parent enzyme into the mutator strain, growing the mutator strain with the plasmid and isolating the mutated plasmid from the mutator strain. The mutated plasmid may be subsequently transformed into the expression organism.

The DNA sequence to be mutagenized may be conveniently present in a genomic or cDNA library prepared from an organism expressing the parent enzyme. Alternatively, the DNA sequence may be present on a suitable vector such as a plasmid or a bacteriophage, which as such may be incubated with or other-wise exposed to the mutagenising agent. The DNA to be mutagenized may also be present in a host cell either by being integrated in the genome of said cell or by being present on a vector harboured in the cell. Finally, the DNA to be mutagenized may be in isolated form. It will be understood that the DNA sequence to be subjected to random mutagenesis is preferably a cDNA or a genomic DNA sequence.

In some cases it may be convenient to amplify the mutated DNA sequence prior to performing the expression step b) or the screening step c). Such amplification may be performed in accordance with methods known in the art, the presently preferred method being PCR-generated amplification using oligonucleotide primers prepared on the basis of the DNA or amino acid sequence of the parent enzyme.

Subsequent to the incubation with or exposure to the mutagenising agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent enzyme during the mutagenesis treatment. Examples of suitable host cells are the following: gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis, Streptomyces lividans* or *Streptomyces murinus*; and gram-negative bacteria such as *E. coli*.

The mutated DNA sequence may further comprise a DNA sequence encoding functions permitting expression of the mutated DNA sequence.

Localized Random Mutagenesis

The random mutagenesis may be advantageously localized to a part of the parent enzyme in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localized, or region-specific, random mutagenesis is conveniently performed by use of PCR generated mutagenesis techniques as described above or any other suitable technique known in the art. Alternatively, the DNA sequence encoding the part of the DNA sequence to be modified may be isolated, e.g., by insertion into a suitable vector, and said part may be subsequently subjected to mutagenesis by use of any of the mutagenesis methods discussed above.

Homology to Other Parent Enzyme

In an embodiment, the present invention also relates to variants of isolated parent polypeptides having an amino acid sequence which has a degree of identity to any of SEQ ID NO: 1, SEQ ID NO: 2, SEQ ID NO: 3 and SEQ ID NO: 4 of at least about 60%, preferably at least about 70%, preferably at least about 80%, preferably at least about 90%, preferably at least about 93%, more preferably at least about 95%, even more preferably at least about 97%, and most preferably at least about 99%, and which have pullulanase or isoamylase activity (hereinafter "homologous polypeptides"). In a preferred embodiment, the homologous parent polypeptides have an amino acid sequence which differs by five amino acids, preferably by four amino acids, more preferably by three amino acids, even more preferably by two amino acids, and most preferably by one amino acid from any of SEQ ID NO: 1, SEQ ID NO: 2, SEQ ID NO: 3 and SEQ ID NO: 4.

The amino acid sequence homology may be determined as the degree of identity between the two sequences indicating a derivation of the first sequence from the second. "Homology" (identity) may be determined by use of any conventional algorithm, preferably by use of the gap program from the GCG package version 8 (August 1994) using default values for gap penalties, i.e., a gap creation penalty of 3.0 and gap extension penalty of 0.1 (Genetic Computer Group (1991) Programme Manual for the GCG Package, version 8, 575 Science Drive, Madison, Wis., USA 53711).

Preferably, the parent polypeptides comprise the amino acid sequences of any of SEQ ID NO: 1, SEQ ID NO: 2, SEQ ID NO: 3 and SEQ ID NO: 4; or allelic variants thereof; or a fragment thereof that has pullulanase or isoamylase activity.

Fragments of SEQ ID NO: 1, SEQ ID NO: 2, SEQ ID NO: 3 and SEQ ID NO: 4 are polypeptides having one or more amino acids deleted from the amino and/or carboxyl terminus of these amino acid sequences.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

In another embodiment, the isolated parent polypeptides having pullulanase or isoamylase activity are encoded by nucleic acid sequences which hybridize under very low stringency conditions, more preferably low stringency conditions more preferably medium stringency conditions, more preferably medium-high stringency conditions, even more preferably high stringency conditions, and most preferably very high stringency conditions with a nucleic acid probe which hybridizes under the same conditions with (i) the nucleic acid sequence of SEQ ID NO: 12 or SEQ ID NO: 13; (ii) a subsequence of (i); or (iii) a complementary strand of (i) or (ii) (J. Sambrook, E. F. Fritsch, and T. Maniatus, 1989, *Molecular Cloning, A Laboratory Manual*, 2d edition, Cold Spring Harbor, N.Y.). The subsequence of SEQ ID NO: 12 or SEQ ID NO: 13 may be at least 100 nucleotides or preferably at least 200 nucleotides. Moreover, the subsequence may encode a polypeptide fragment which has pullulanase or isoamylase activity, respectively. The parent polypeptides may also be allelic variants or fragments of the polypeptides that have pullulanase or isoamylase activity.

The nucleic acid sequence of SEQ ID NO: 12 or SEQ ID NO: 13 or a subsequence thereof, as well as the amino acid sequence of SEQ ID NO: 1, SEQ ID NO: 2, SEQ ID NO: 3 and SEQ ID NO: 4 or a fragment thereof, may be used to design a nucleic acid probe to identify and clone DNA encoding polypeptides having pullulanase or isoamylase activity, from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

Thus, a genomic DNA or cDNA library prepared from such other organisms may be screened for DNA which hybridizes with the probes described above and which encodes a polypeptide having pullulanase or isoamylase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 12 or SEQ ID NO: 13 or subsequences thereof, the carrier material is used in a Southern blot. For purposes of the present invention, hybridization indicates that the nucleic acid sequence hybridizes to a nucleic acid probe corresponding to the nucleic acid sequence shown in SEQ ID NO: 12 or SEQ ID NO: 13, its complementary strand, or a subsequence thereof, under very low to very high stringency conditions. Molecules to which the nucleic acid probe hybridizes under these conditions are detected using X-ray film.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at 5° C. to 10° C. below the calculated $T_m$ using the calculation according to Bolton and McCarthy (1962, *Proceedings of the National Academy of Sciences* USA 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

The present invention also relates to isolated nucleic acid sequences produced by (a) hybridizing a DNA under very low, low, medium, medium-high, high, or very high stringency conditions with the sequence of SEQ ID NO: 12 or SEQ ID NO: 13, or its complementary strand, or a subsequence thereof; and (b) isolating the nucleic acid sequence. The subsequence is preferably a sequence of at least 100 nucleotides such as a sequence which encodes a polypeptide fragment which has pullulanase or isoamylase activity.

Contemplated parent polypeptides have at least 20%, preferably at least 40%, more preferably at least 60%, even more preferably at least 80%, even more preferably at least 90%, and most preferably at least 100% of the pullulanase or isoamylase activity of the mature polypeptide of SEQ ID NO: 1, SEQ ID NO: 2, SEQ ID NO: 3 and SEQ ID NO: 4.

The invention will be further illustrated by the following non-limiting examples.

EXAMPLES

Example 1

Donor Organisms:

*Bacillus acidopullulyticus* comprises the pullulanase enzyme encoding DNA sequence of the pulB gene (SEQ ID NO: 13) (Kelly, A. P., Diderichsen, B., Jorgensen, S. And McConnett, D. J.(1994) Molecular genetic analysis of the pullulanase B gene of *Bacillus acidopullulyticus*. FEMS Microbiology letters 115, 97-106).

Other Strains:

*E. coli* strain: Cells of *E. coli* SJ2 (Diderichsen, B., Wedsted, U., Hedegaard, L., Jensen, B. R., Sjøholm, C. (1990) Cloning of aldB, which encodes alpha-acetolactate decarboxylase, an exoenzyme from *Bacillus brevis*. J. Bacteriol., 172, 4315-4321), were prepared for and transformed by electroporation using a Gene PulserTM electroporator from BIO-RAD as described by the supplier.

*B. subtilis* PL1801. This strain is the *B. subtilis* DN1885 with disrupted apr and npr genes (Diderichsen, B., Wedsted, U., Hedegaard, L., Jensen, B. R., Sjøholm, C. (1990) Cloning of aldB, which encodes alpha-acetolactate decarboxylase, an exoenzyme from *Bacillus brevis*. J. Bacteriol., 172, 4315-4321). Competent cells were prepared and transformed as described by Yasbin, R. E., Wilson, G. A. and Young, F. E. (1975) Transformation and transfection in lysogenic strains of *Bacillus subtilis*: evidence for selective induction of prophage in competent cells. J. Bacteriol, 121:296-304.

Plasmids.

pMOL944. This plasmid is a pUB110 derivative essentially containing elements making the plasmid popagatable in *Bacillus subtilis*, kanamycin resistance gene and having a strong promoter and signal peptide cloned from the amyL gene of *B. licheniformis* ATCC14580. The signal peptide contains a SacII site making it convenient to clone the DNA encoding the mature part of a protein in-fusion with the signal peptide. This results in the expression of a Pre-protein which is directed towards the exterior of the cell.

The plasmid was constructed by means of ordinary genetic engineering and is briefly described in the following. Construction of pMOL944:

The pUB110 plasmid (McKenzie, T. et al., 1986, Plasmid 15:93-103) was digested with the unique restriction enzyme NciI. A PCR fragment amplified from the amyL promoter encoded on the plasmid pDN1981 (P. L. Jørgensen et al., 1990, Gene, 96, p37-41.) was digested with NciI and inserted in the NciI digested pUB110 to give the plasmid pSJ2624.

```
#LWN5494   5'-GTCGCCGGGGCGGCCGCTATCAATTGGTAACTGTATCTCAGC-3'
           (SEQ ID NO:15)

#LWN5495   5'-GTCGCCCGGGAGCTCTGATCAGGTACCAAGCTTGTCGACCTGCAGAATGAGGCAGCAAGAAGAT-3'
           (SEQ ID NO:16)
```

The primer #LWN5494 inserts a NotI site in the plasmid.

The plasmid pSJ2624 was then digested with SacI and NotI and a new PCR fragment amplified on amyL promoter encoded on the pDN1981 was digested with SacI and NotI and this DNA fragment was inserted in the SacI-NotI digested pSJ2624 to give the plasmid pSJ2670.

```
#LWN5938
5'-GTCGGCGGCCGCTGATCACGTACCAAGCTTGTCGACCTGCAGAATGA
GGCAGCAAGAAGAT -3'(SEQ ID NO:17)

#LWN5939
5'-GTCGGAGCTCTATCAATTGGTAACTGTATCTCAGC-3'
(SEQ ID NO:18)

#LWN7864 5'-AACAGCTGATCACGACTGATCTTTTAGCTTGGCAC-3'
         (SEQ ID NO:19)

#LWN7901 5'-AACTGCAGCCGCGGCACATCAAATGGGACAAATGGG-3'
         (SEQ ID NO:20)
```

The primer #LWN7901 inserts a SacII site in the plasmid.

Subcloning and expression of pullulanase pulB in *B. subtilis*. The pulB encoding DNA sequence of the invention was PCR amplified using the PCR primer set consisting of these two oligo nucleotides:

```
pulB.upper.SacII
5'-CAT TCT GCA GCC GCG GCA GAT TCT ACC TCG ACA GAA
                              GTC-3'(SEQ ID NO:14)
pulB.lower.NotI
5'-GTT GAG AAA A GC GGC CGC TTC TTT AAC ACA TGC
                              TAC GG-3'(SEQ ID NO:14)
```

Restriction sites SacII and NotII are underlined.

The pulB upper SacII primer is situated just after the signal sequence of the pulB gene and will after cloning in the pMOL944 vector generate a signal fusion to the amyL signal sequence.

The pulB lower primer is situated just after the mRNA terminator of the pulB gene.

Genomic DNA Preparation:

Strain *Bacillus pullulyticus* (ID noxxxx) was propagated in liquid TY medium. After 16 hours incubation at 30° C. and 300 rpm, the cells were harvested, and genomic DNA isolated by the method described by Pitcher et al. (Pitcher, D. G., Saunders, N. A., Owen, R. J. (1989). Rapid extraction of bacterial genomic DNA with guanidium thiocyanate. Lett. Appl. Microbiol., 8, 151-156).

Chromosomal DNA isolated from *B. pullulyticus* as described above was used as template in a PCR reaction using Amplitaq DNA Polymerase (Perkin Elmer) according to manufacturers instructions. The PCR reaction was set up in PCR buffer (10 mM Tris-HCl, pH 8.3, 50 mM KCl, 1.5 mM MgCl2, 0.01% (w/v) gelatin) containing 200 μM of each dNTP, 2.5 units of AmpliTaq polymerase (Perkin-Elmer, Cetus, USA) and 100 pmol of each primer The PCR reactions was performed using a DNA thermal cycler (Landgraf, Germany). One incubation at 94° C. for 1 min followed by thirty cycles of PCR performed using a cycle profile of denaturation at 96° C. for 10 sec, annealing at 60° C. for 30 sec, and extension at 72° C. for 150 sec. Five-μl aliquots of the amplification product was analysed by electrophoresis in 0.7% agarose gels (NuSieve, FMC). The appearance of a DNA fragment size 2.5 kb indicated proper amplification of the gene segment.

Subcloning of PCR Fragment.

Fortyfive-μl aliquots of the PCR products generated as described above were purified using QIAquick PCR purification kit (Qiagen, USA) according to the manufacturer's instructions. The purified DNA was eluted in 50 μl of 10 mM Tris-HCl, pH 8.5. 5 μg of pMOL944 and twentyfive-μl of the purified PCR fragment was digested with SacII and NotI, electrophoresed in 0.8% low gelling temperature agarose (SeaPlaque GTG, FMC) gels, the relevant fragments were excised from the gels, and purified using QIAquick Gel extraction Kit (Qiagen, USA) according to the manufacturer's instructions. The isolated PCR DNA fragment was then ligated to the SacII-NotI digested and purified pMOL944. The ligation was performed overnight at 16° C. using 0.5 μg of each DNA fragment, 1 U of T4 DNA ligase and T4 ligase buffer (Boehringer Mannheim, Germany).

The ligation mixture was used to transform competent *B. subtilis* PL2306. The transformed cells were plated onto LBPG-10 μg/ml of Kanamycin –0.1% AZCL-Pullulan-agar plates. After 18 hours incubation at 37° C. cells positively expressing the cloned Pullulanase were seen as colonies surrounded by blue halos. One such positive clone was restreaked several times on agar plates as used above, this clone was called PULxxx. The clone PULxxx was grown overnight in TY-10 μg/ml Kanamycin at 37° C., and next day 1 ml of cells were used to isolate plasmid from the cells using the Qiaprep Spin Plasmid Miniprep Kit #27106 according to the manufacturers recommendations for *B. subtilis* plasmid preparations.

Expression of Pullulanase.

PULxxx was grown in 25×200 ml BPX media with 10 μg/ml of Kanamycin in 500 ml two baffled shakeflasks for 5 days at 30° C. at 300 rpm.

```
pulB seq:
AAAAAATGCTTAATAGAAGGAGTGTAATCTGTGTCCCTAATACGTTCTAGGTATAATCATTTTG    (SEQ ID NO: 13)

TCATTCTTTTTACTGTCGCCATAATGTTTCTAACAGTTTGTTTCCCCGCTTATAAAGCTTTAGC

AGATTCTACCTCGACAGAAGTCATTGTGCATTATCATCGTTTTGATTCTAACTATGCAAATTGG

GATCTATGGATGTGGCCATATCAACCAGTTAATGGTAATGGAGCAGCATACGAGTTTTCTGGAA

AGGATGATTTTGGCGTTAAAGCAGATGTTCAAGTGCCTGGGGATGATACACAGGTAGGTCTGAT

TGTCCGTACAAATGATTGGAGCCAAAAAAATACATCAGACGATCTCCATATTGATCTGACAAAG

GGGCATGAAATATGGATTGTTCAGGGGGATCCCAATATTTATTACAATCTGAGTGATGCGCAGG
```

-continued

```
CTGCAGCGACTCCAAAGGTTTCGAATGCGTATTTGGATAATGAAAAAACAGTATTGGCAAAGCT
AACTAATCCAATGACATTATCAGATGGATCAAGCGGCTTTACGGTTACAGATAAAACAACAGGG
GAACAAATTCCAGTTACCGCTGCAACAAATGCGAACTCAGCCTCCTCGTCTGAGCAGACAGACT
TGGTTCAATTGACGTTAGCCAGTGCACCGGATGTTTCCCATACAATACAAGTAGGAGCAGCCGG
TTATGAAGCAGTCAATCTCATACCACGAAATGTATTAAATTTGCCTCGTTATTATTACAGCGGA
AATGATTTAGGTAACGTTTATTCAAATAAGGCAACGGCCTTCCGTGTATGGGCTCCAACTGCTT
CGGATGTCCAATTACTTTTATACAATAGTGAAACAGGACCTGTAACCAAACAGCTTGAAATGCA
AAAGAGTGATAACGGTACATGGAAACTGAAGGTCCCTGGTAATCTGAAAAATTGGTATTATCTC
TATCAGGTAACGGTGAATGGGAAGACACAAACAGCCGTTGACCCTTATGTGCGTGCTATTTCAG
TCAATGCAACACGTGGTATGATAGTCGATTTAGAAGATACGAATCCTCCTGGATGGAAAGAAGA
TCATCAACAGACACCTGCGAACCCAGTGGATGAAGTAATCTACGAAGTGCATGTGCGTGATTTT
TCGATTGATGCTAATTCAGGCATGAAAAATAAAGGGAAATATCTTGCCTTTACAGAACATGGCA
CAAAAGGCCCTGATAACGTGAAAACGGGTATTGATAGTTTGAAGGAATTAGGAATCAATGCTGT
TCAATTACAGCCGATTGAAGAATTTAACAGCATTGATGAAACCCAACCAAATATGTATAACTGG
GGCTATGACCCAAGAAACTACAACGTCCCTGAAGGAGCGTATGCAACTACACCAGAAGGAACGG
CTCGCATTACCCAGTTAAAGCAACTGATTCAAAGCATTCATAAAGATCGGATTGCTATCAATAT
GGATGTGGTCTATAACCATACCTTTAACGTAGGAGTGTCTGATTTTGATAAGATTGTTCCGCAA
TACTATTATCGGACAGACAGCGCAGGTAATTATACGAACGGCTCAGGTGTAGGTAATGAAATTG
CGACCGAGCGTCCGATGGTCCAAAAGTTCGTTCTGGATTCTGTTAAATATTGGGTAAAGGAATA
CCATATCGACGGCTTC
CGTTTCGATCTTATGGCTCTTTTAGGAAAAGACACCATGGCCAAAATATCAAAGAGCTTCATG
CTATTAATCCTGGCATTGTCCTGTATGGAGAACCATGGACTGGCGGTACCTCTGGATTATCAAG
CGACCAACTCGTTACGAAAGGTCAGCAAAAGGGCTTGGGAATTGGCGTATTCAACGATAATATT
CGGAACGGACTCGATGGTAACGTTTTTGATAAATCGGCACAAGGATTTGCAACAGGAGATCCAA
ACCAAGTTAATGTCATTAAAAATAGAGTTATGGGAAGTATTTCAGATTTCACTTCGGCACCTAG
CGAAACCATTAACTATGTAACAAGCCATGATAATATGACATTGTGGGATAAAATTAGCGCAAGT
AATCCGAACGATACACAAGCAGATCGAATTAAGATGGATGAATTGGCTCAAGCTGTGGTATTTA
CTTCACAAGGGGTACCATTTATGCAAGGTGGAGAAGAAATGCTGCGGACAAAAGGCGGTAATGA
TAATAGTTACAATGCCGGGGATAGCGTGAATCAGTTCGATTGGTCAAGAAAAGCACAATTTGAA
AATGTATTCGACTACTATTCTTGGTTGATTCATCTACGTGATAATCACCCAGCATTCCGTATGA
CGACAGCGGATCAAATCAAACAAAATCTCACTTTCTTGGATAGCCCAACGAACACTGTAGCATT
TGAATTAAAAAATCATGCCAATCATGATAAATGGAAAAACATTATAGTTATGTATAATCCAAAT
AAAACTGCACAAACTCTCACTCTACCAAGTGGAAATTGGACAATTGTAGGATTAGGCAATCAAG
TAGGTGAGAAATCACTAGGCCATGTAAATGGCACGGTTGAGGTGCCAGCTCTTAGTACGATCAT
TCTTCATCAGGGTACATCTGAAGATGTCATTGATCAAAATTAATATTGATTAAGAAATGATTTG
TAAAACATTTAAGTCCATTTACACGGGATACTGTGTAAATGGATTTTAGTTTTATCCGTAGCAT
GTGTTAAAGAAGTAAATAGTAAATGGCAATTT
```

Target for the Two Amplifying Primers is Indicated

Media:

TY (as described in Ausubel, F. M. et al. (eds.) "Current protocols in Molecular Biology". John Wiley and Sons, 1995). LB agar (as described in Ausubel, F. M. et al. (eds.) "Current protocols in Molecular Biology". John Wiley and Sons, 1995).

LBPG is LB agar supplemented with 0.5% Glucose and 0.05 M potassium phosphate, pH 7.0

AZCL-Pullulan is added to LBPG-agar to 0.5% AZCL-pullulan is from Megazyme, Australia.

BPX media is described in EP 0 506 780 (WO 91/09129).

Example 2

Purification of *Bacillus acidopullulyticus* Pullulanase (Promozyme™)

*Bacillus acidopullulyticus* pullulanase was purified from a fermentation of *B. acidopullulyticus* (described in EP 63,909), the pullulanase being secreted to the medium.

A filter aid was added to the culture broth, which was filtered through a filtration cloth. This solution was further filtered through a Seitz depth filter plate, resulting in a clear solution. The filtrate was concentrated by ultrafiltration on 10 kDa cut-off polyethersulfone membranes followed by dialfiltration with distilled water to reduce the conductivity. The pH of the concentrated enzyme was adjusted to pH 4.5. The conductivity of the concentrated enzyme was 0.7 mS/cm.

The concentrated pullulanase was applied to an S-Sepharose FF column equilibrated in 20 mM $CH_3COOH$/NaOH, pH 4.5, and the enzyme was eluted with a linear NaCl gradient (0→0.5M). The pullulanase activity eluted as a single peak. The pooled fractions with pullulanase activity were transferred to 20 mM $KH_2PO_4$/NaOH, pH 7.0 on a Sephadex G25 column. The enzyme was further purified by application to a Q-Sepharose FF column equilibrated in 20 mM $KH_2PO_4$/NaOH, pH 7.0. After washing the column, the pullulanase was eluted with a linear NaCl gradient (0→0.5M). Fractions with pullulanase activity were pooled and the buffer was exchanged for 20 mM $CH_3COOH$/NaOH, pH 4.5, on a Sephadex G25 column. The pullulanase was then applied to a SOURCE 30S column equilibrated in 20 mM $CH_3COOH$/NaOH, pH 4.5. After washing the column, the pullulanase activity was eluted with an increasing linear NaCl gradient (0→0.2M). Fractions with pullulanase activity were pooled and concentrated on an ultrafiltration cell with a 10 kDa cut-off regenerated cellulose membrane. The concentrated enzyme was applied to a Superdex200 size exclusion column equilibrated in 20 mM $CH_3COOH$/NaOH, 200 mM NaCl, pH 4.5. Fractions eluted from the Superdex200 column were analyzed by SDS-PAGE and pure pullulanase fractions were pooled.

The pullulanase migrates on SDS-PAGE as a band with $M_r$=100 kDa.

Other pullulanases and isoamylases may be purified essentially in the same manner.

Sepharose, Sephadex, SOURCE and Superdex are trademarks owned by Amersham Pharmacia Biotech.

Example 3

Thermostability of Pullulanases and Isoamylases

The thermostability of pullulanases and isoamylses may be tested by means of DSC (Differential Scanning Calorimetry). The thermal denaturation temperature, Td, is taken as the top of the denaturation peak in thermograms (Cp vs. T) obtained after heating enzyme solutions at a constant, programmed heating rate.

Experimental:

A suitable DSC apparatus, e.g. a DSC II apparatus from Hart Scientific (Utah, USA) may used for the experiments. 50 mM buffered solutions are used as solvent for the enzyme (approx. 2 mg/ml) at either pH 10 (50 mM glycine buffer), pH 7 (50 mM HEPES buffer+10 mM EDTA) or pH 4 (50 mM citrate buffer). The enzyme may be purified as described above. 750 µl enzyme solution is transferred into standard 1 ml sealable hastelloy ampoules (Hart Scientific). Ampoules are loaded into the calorimeter and cooled to 5° C. for 15 min. Thermal equilibration is carried out prior to the DSC scan. The DSC scan is performed at from 5° C. to 95° C. at a scan rate of approx. 90 K/hr. Denaturation temperatures are determined with an accuracy of approx. +/−2° C. The results are expressed as top to denaturation peak as a function of pH.

Example 4

Activity

Debranching Activity Assay:

The results below show that the specific activity (activity/mg pure enzyme) is highly dependent on the enzyme class. Isoamylases are extremely active towards high molecular weight branched starchy material such as glycogen and amylopectin, whereas pullulanases are very low in activity towards these substrates. The activity unit reflects the number of reducing ends which are formed during a 10 min. incubation period. The opposite picture is observed with pullulanases, i.e. low activity towards high molecular weight branched starchy material such as glycogen and amylopectin but high activity towards e.g. pullulan.

A high activity towards amylopectin and glycogen is particularly preferable when an enzymatic debranching is to take place together with the action of an α-amylase in the liquefaction process. On the other hand, a high activity towards small oligosaccharides such as pullulan is preferable when an enzymatic debranching is to take place during the saccharification step, i.e. after the liquefaction process when the high molecular weight components have been broken down to smaller oligosaccharides. If a pullulanase could be altered to have a high activity (specificity) towards high molecular weight compounds such as amylopectin, this would be highly preferable when the pullulanase is added during the liquefaction process.

Substrates used: rabbit liver glycogen and pullulan. Previous tests had showed that a high concentration of substrate was needed in order for the substrate not to be the limiting factor when a linear assay is developed. A "high" substrate concentration is, in this context, 10% w/v. The Somogyi-Nelson assay measures the amount of reducing ends formed by enzymatic degradation of the substrate. With normal assay times of up to 3 hours, the formation of reducing ends is fairly limited, even though the enzyme concentration is high (10% w/v). This means that the assay measures a relatively small difference in reducing ends on a very high background which is much higher than the measurable difference in absorbance during the enzyme treatment. For this reason, the reducing ends in glycogen and pullulan were oxidised with $NaBH_4$ as follows in order to reduce the substrate background level:

1000 mg of glycogen was dissolved in 40 ml of water to which 0.2% NaOH had been added. 800 mg NaBH₄ was added carefully under stirring. The solution was stirred for 48 h at 25° C., after which the reaction was stopped by adding Amberlite IR-118H, a cation exchanger which removes the boron ions and stop the reaction. The solution was filtered to remove the matrix and was evaporated to give 10 ml. The solution was dialyased extensively against deionized water in order to remove residual boron ions. This method was found to reduce the background value by at least a factor of 10.

The assay was conducted according to the method of Somogyi-Nelson, using 50 mM sodium acetate, pH values of 4.5, 5.0 and 5.5 and a temperature of 50° C. (isoamylase) or 60° C. (pullulanases), with a reaction time of 10 min. Glucose was used as a standard, a standard curve being made from solutions containing of 0-200 mg glucose/liter.

TABLE 3

| Glycogen from Rabbit liver | Temp. | pH | PUN/mg |
|---|---|---|---|
| Pullulanase from B. acidopullulyticus (SEQ ID NO 1) | 60° C. | 4.5 | 50 |
| | 60° C. | 5.0 | 49 |
| | 60° C. | 5.5 | 51 |
| Pullulanase from B. deramificans (SEQ ID NO 2) | 60° C. | 4.5 | 37 |
| | 60° C. | 5.0 | 31 |
| | 60° C. | 5.5 | 30 |
| Isoamylase from Pseudomonas (SEQ ID NO 4) | 50° C. | 4.5 | 2829 |
| | 50° C. | 5.0 | 2858 |
| | 50° C. | 5.5 | 2709 |
| Pullulan | | | |
| Pullulanase from B. acidopullulyticus (SEQ ID NO 1) | 60° C. | 4.5 | 402 |
| | 60° C. | 5.0 | 414 |
| | 60° C. | 5.5 | 393 |
| Pullulanase from B. deramificans (SEQ ID NO 2) | 60° C. | 4.5 | 288 |
| | 60° C. | 5.0 | 276 |
| | 60° C. | 5.5 | 255 |
| Isoamylase from Pseudomonas (SEQ ID NO 4) | 50° C. | 4.5 | 14 |
| | 50° C. | 5.0 | 14 |
| | 50° C. | 5.5 | 6 |

SEQ ID NO 12:

```
(2) INFORMATION FOR SEQ ID NO: 12:
    (i)  SEQUENCE CHARACTERISTICS:
         (A) LENGTH: 2181 base pairs
         (B) TYPE: nucleic acid
         (C) STRANDEDNESS: single
         (D) TOPOLOGY: linear
    (ii) MOLECULE TYPE: DNA (genomic)
    (vi) ORIGINAL SOURCE:
         (B) STRAIN: Rhodothermus marinus DSM 4252
    (ix) FEATURE:
         (A) NAME/KEY: CDS
         (B) LOCATION:1..2181
    (xi) SEQUENCE DESCRIPTION: SEQ ID NO: 12:

ATG TCA CAT AGC GCG CAA CCG GTT ACG TCG GTA CAG GCC GTC TGG CCC    48
Met Ser His Ser Ala Gln Pro Val Thr Ser Val Gln Ala Val Trp Pro
 1               5                  10                  15

GGC CGG CCT TAT CCG CTG GGT GCC ACC TGG GAC GGG CTG GGC GTC AAC    96
Gly Arg Pro Tyr Pro Leu Gly Ala Thr Trp Asp Gly Leu Gly Val Asn
                20                  25                  30

TTT GCC CTC TAC AGC CAG CAC GCC GAG GCG GTC GAA CTG GTG CTG TTC   144
Phe Ala Leu Tyr Ser Gln His Ala Glu Ala Val Glu Leu Val Leu Phe
            35                  40                  45

GAC CAC CCG GAC GAT CCC GCG CCT TCG CGC ACG ATC GAA GTG ACC GAA   192
Asp His Pro Asp Asp Pro Ala Pro Ser Arg Thr Ile Glu Val Thr Glu
        50                  55                  60

CGG ACA GGC CCG ATC TGG CAT GTG TAC CTG CCC GGC CTG CGT CCC GGC   240
Arg Thr Gly Pro Ile Trp His Val Tyr Leu Pro Gly Leu Arg Pro Gly
 65                  70                  75                  80

CAG CTC TAC GGC TAT CGC GTC TAC GGA CCC TAC CGG CCG GAG GAA GGC   288
Gln Leu Tyr Gly Tyr Arg Val Tyr Gly Pro Tyr Arg Pro Glu Glu Gly
                85                  90                  95
```

TABLE 3-continued

```
CAC CGC TTC AAT CCG AAC AAG GTG CTG CTC GAC CCC TAC GCG AAG GCC    336
His Arg Phe Asn Pro Asn Lys Val Leu Leu Asp Pro Tyr Ala Lys Ala
            100                 105                 110

ATC GGC CGG CCC CTT CGC TGG CAC GAC AGC CTC TTC GGT TAC AAA ATC    384
Ile Gly Arg Pro Leu Arg Trp His Asp Ser Leu Phe Gly Tyr Lys Ile
            115                 120                 125

GGC GAT CCG GCC GGG GAT CTG TCG TTC TCC GAA GAA GAC AGC GCT CCG    432
Gly Asp Pro Ala Gly Asp Leu Ser Phe Ser Glu Glu Asp Ser Ala Pro
130                 135                 140

TAC GCG CCG CTG GGA GCC GTC GTG GAG GGC TGT TTC GAG TGG GGC GAC    480
Tyr Ala Pro Leu Gly Ala Val Val Glu Gly Cys Phe Glu Trp Gly Asp
145                 150                 155                 160

GAC CGC CCG CCG CGC ATT CCC TGG GAA GAC ACG ATC ATC TAC GAA ACG    528
Asp Arg Pro Pro Arg Ile Pro Trp Glu Asp Thr Ile Ile Tyr Glu Thr
                165                 170                 175

CAC GTC AAG GGC ATC ACG AAG CTG CAT CCG GAA GTG CCG GAG CCG CTG    576
His Val Lys Gly Ile Thr Lys Leu His Pro Glu Val Pro Glu Pro Leu
            180                 185                 190

CGG GGG ACG TAT CTG GGG CTG ACC TGC GAG CCG GTG CTG GAG CAC CTG    624
Arg Gly Thr Tyr Leu Gly Leu Thr Cys Glu Pro Val Leu Glu His Leu
            195                 200                 205

AAG CAG CTG GGC GTC ACC ACG ATC CAG CTC CTT CCG GTG CAC GCA AAA    672
Lys Gln Leu Gly Val Thr Thr Ile Gln Leu Leu Pro Val His Ala Lys
            210                 215                 220

GTG CAC GAT CGG CAC CTG GTC GAG CGC GGC CTG CGC AAC TAC TGG GGC    720
Val His Asp Arg His Leu Val Glu Arg Gly Leu Arg Asn Tyr Trp Gly
225                 230                 235                 240

TAC AAT CCG CTC TGC TAC TTT GCG CCG GAG CCC GAG TAC GCC ACG AAC    768
Tyr Asn Pro Leu Cys Tyr Phe Ala Pro Glu Pro Glu Tyr Ala Thr Asn
                245                 250                 255

GGG CCG ATC TCG GCC GTG CGC GAG TTC AAG ATG ATG GTG CGG GCG CTG    816
Gly Pro Ile Ser Ala Val Arg Glu Phe Lys Met Met Val Arg Ala Leu
            260                 265                 270

CAT GCT GCC GGC TTC GAG GTG ATC GTC GAC GTG GTC TAC AAC CAC ACG    864
His Ala Ala Gly Phe Glu Val Ile Val Asp Val Val Tyr Asn His Thr
            275                 280                 285

GGC GAA GGC GGC GTG CTG GGC CCC ACG CTG TCG TTC CGG CCC ATC GAC    912
Gly Glu Gly Gly Val Leu Gly Pro Thr Leu Ser Phe Arg Pro Ile Asp
            290                 295                 300

AAC CGC GCC TAC TAC AAG GCC GAT CCG AAC AAC CCG CGC TTT CTG GTC    960
Asn Arg Ala Tyr Tyr Lys Ala Asp Pro Asn Asn Pro Arg Phe Leu Val
305                 310                 315                 320

GAT TAC ACG GGC ACC GGC AAC ACG CTG GAC GTG GGC AAC CCC TAC GTC   1008
Asp Tyr Thr Gly Thr Gly Asn Thr Leu Asp Val Gly Asn Pro Tyr Val
                325                 330                 335

ATC CAG CTC ATC ATG GAC AGC CTG CGC TAC TGG GTC ACT GAA ATG CAC   1056
Ile Gln Leu Ile Met Asp Ser Leu Arg Tyr Trp Val Thr Glu Met His
            340                 345                 350

GTC GAC GGC TTT CGG TTC GAC CTG GCC GCC GCG CTG GCC CGC GAG CTG   1104
Val Asp Gly Phe Arg Phe Asp Leu Ala Ala Ala Leu Ala Arg Glu Leu
            355                 360                 365

TAC GAC GTG GAC ATG CTC TCG ACC TTT TTT CAG GTC ATT CAG CAG GAC   1152
Tyr Asp Val Asp Met Leu Ser Thr Phe Phe Gln Val Ile Gln Gln Asp
            370                 375                 380

CCG GTG CTC AGC CAG GTC AAG CTC ATC GCC GAA CCC TGG GAC GTC CGG   1200
Pro Val Leu Ser Gln Val Lys Leu Ile Ala Glu Pro Trp Asp Val Gly
385                 390                 395                 400

CCG GGG GGG TAT CAG GTG GGA CAT TTT CCC TGG CAG TGG ACC GAG TGG   1248
Pro Gly Gly Tyr Gln Val Gly His Phe Pro Trp Gln Trp Thr Glu Trp
                405                 410                 415
```

TABLE 3-continued

```
AAC GGC CGC TAT CGT GAC GCC GTG CGC CGC TTC TGG CGG GGC GAT CGG   1296
Asn Gly Arg Tyr Arg Asp Ala Val Arg Arg Phe Trp Arg Gly Asp Arg
            420                 425                 430

GGC CTC AAC GGT GAG TTT GCC ACG CGC TTT GCC GGC TCC AGC GAT CTG   1344
Gly Leu Asn Gly Glu Phe Ala Thr Arg Phe Ala Gly Ser Ser Asp Leu
            435                 440                 445

TAC GAA CGT AGC GGT CGT CGT CCG TTC GCT TCG ATC AAC TTC GTC ACG   1392
Tyr Glu Arg Ser Gly Arg Arg Pro Phe Ala Ser Ile Asn Phe Val Thr
    450                 455                 460

GCG CAC GAC GGC TTC ACG CTG GAA GAC CTG GTC AGC TAC ACG AAA AAG   1440
Ala His Asp Gly Phe Thr Leu Glu Asp Leu Val Ser Tyr Thr Lys Lys
465                 470                 475                 480

CAC AAC GAA GCG AAT CTG GAA GGC AAC CGG GAC GGC ATG GAC GAA AAC   1488
His Asn Glu Ala Asn Leu Glu Gly Asn Arg Asp Gly Met Asp Glu Asn
                    485                 490                 495

TAC AGC ACG AAC TGC GGG GTG GAG GGA CCC ACG CAG GAT CCG TCC GTG   1536
Tyr Ser Thr Asn Cys Gly Val Glu Gly Pro Thr Gln Asp Pro Ser Val
                500                 505                 510

CTG GCC TGC CGG GAA GCG CTC AAG CGC AGC CTG ATC AGC ACG CTC TTT   1584
Leu Ala Cys Arg Glu Ala Len Lys Arg Ser Leu Ile Ser Thr Leu Phe
            515                 520                 525

CTC TCG CAG GGC GTG CCC ATG CTG CTG GGC GGC GAC GAG CTG TCG CGC   1632
Len Ser Gln Gly Val Pro Met Leu Leu Gly Gly Asp Glu Leu Ser Arg
        530                 535                 540

ACG CAG CAC GGC AAC AAC AAC GCC TAT TGC CAG GAC AAC GAG ATC AGC   1680
Thr Gln His Gly Asn Asn Asn Ala Tyr Cys Gln Asp Asn Glu Ile Ser
545                 550                 555                 560

TGG TAC AAC TGG CAG CTC GAC ACG CGC AAG CAG CAG TTT CTG GAG TTC   1728
Trp Tyr Asn Trp Gln Leu Asp Thr Arg Lys Gln Gln Phe Leu Glu Phe
                    565                 570                 575

GTG CGC CAG ACG ATC TGG TTT CGC AAG CAG CAT CGG AGC TTC CGG CGC   1776
Val Arg Gln Thr Ile Trp Phe Arg Lys Gln His Arg Ser Phe Arg Arg
                580                 585                 590

CGC CAT TTT CTG ACC GGA TTG CCC AAC GGC GGA AGG CCC CGA CGC AGT   1824
Arg His Phe Leu Thr Gly Leu Pro Asn Gly Gly Arg Pro Arg Arg Ser
            595                 600                 605

CTG GTG GCA CCT GAG GGT CGG CCC ATG CGC CAC GAG GAC TGG ACC AAC   1872
Leu Val Ala Pro Glu Gly Arg Pro Met Arg His Glu Asp Trp Thr Asn
        610                 615                 620

CCG GAG CTG ACG GCC TTC GGA CTG CTG CTG CAC GGC GAC GCC ATT CAG   1920
Pro Glu Leu Thr Ala Phe Gly Leu Leu Leu His Gly Asp Ala Ile Gln
625                 630                 635                 640

GGG ACC GAC GAG CAC GGA CGA CCG TTT CGC GAC GAC ACG TTT CTG ATT   1968
Gly Thr Asp Glu His Gly Arg Pro Phe Arg Asp Asp Thr Phe Leu Ile
                    645                 650                 655

CTG TTC AAC AAC GGC AGC GAA GCC GTG CCG GTC GTG GTG CCG GAG GTA   2016
Leu Phe Asn Asn Gly Ser Glu Ala Val Pro Val Val Val Pro Glu Val
                660                 665                 670

TGC TCC TGT GGC AAG CCG CAC CAC TGG GAG GTG GTC CCG GTG TTT CAA   2064
Cys Ser Cys Gly Lys Pro His His Trp Glu Val Val Pro Val Phe Gln
            675                 680                 685

CGC AAT GTG GAG CCC CCC ACG TGC GCG CCC GGC GAG ACG CTG TCG CTC   2112
Arg Asn Val Glu Pro Pro Thr Cys Ala Pro Gly Glu Thr Leu Ser Leu
        690                 695                 700

CCG CCC GGC GTG CTG ACG GTG CTG GTG GCC GTA CCG CCG TTC TCG GAT   2160
Pro Pro Gly Val Leu Thr Val Len Val Ala Val Pro Pro Phe Ser Asp
705                 710                 715                 720
```

TABLE 3-continued

```
GGA AAC ACG GAG CCG GCC TGA  2181
Gly Asn Thr Glu Pro Ala  *
                725
```

SEQUENCE LISTING

<160> NUMBER OF SEQ ID NOS: 14

<210> SEQ ID NO 1
<211> LENGTH: 862
<212> TYPE: PRT
<213> ORGANISM: bacillus acid opullulyticus

<400> SEQUENCE: 1

```
Val Ser Leu Ile Arg Ser Arg Tyr Asn His Phe Val Ile Leu Phe Thr
 1               5                  10                  15

Val Ala Ile Met Phe Leu Thr Val Cys Phe Pro Ala Tyr Lys Ala Leu
            20                  25                  30

Ala Asp Ser Thr Ser Thr Glu Val Ile Val His Tyr His Arg Phe Asp
        35                  40                  45

Ser Asn Tyr Ala Asn Trp Asp Leu Trp Met Trp Pro Tyr Gln Pro Val
    50                  55                  60

Asn Gly Asn Gly Ala Ala Tyr Glu Phe Ser Gly Lys Asp Asp Phe Gly
65                  70                  75                  80

Val Lys Ala Asp Val Gln Val Pro Gly Asp Asp Thr Gln Val Gly Leu
                85                  90                  95

Ile Val Arg Thr Asn Asp Trp Ser Gln Lys Asn Thr Ser Asp Asp Leu
            100                 105                 110

His Ile Asp Leu Thr Lys Gly His Glu Ile Trp Ile Val Gln Gly Asp
        115                 120                 125

Pro Asn Ile Tyr Tyr Asn Leu Ser Asp Ala Gln Ala Ala Ala Thr Pro
    130                 135                 140

Lys Val Ser Asn Ala Tyr Leu Asp Asn Glu Lys Thr Val Leu Ala Lys
145                 150                 155                 160

Leu Thr Asn Pro Met Thr Leu Ser Asp Gly Ser Ser Gly Phe Thr Val
                165                 170                 175

Thr Asp Lys Thr Thr Gly Glu Gln Ile Pro Val Thr Ala Ala Thr Asn
            180                 185                 190

Ala Asn Ser Ala Ser Ser Ser Glu Gln Thr Asp Leu Val Gln Leu Thr
        195                 200                 205

Leu Ala Ser Ala Pro Asp Val Ser His Thr Ile Gln Val Gly Ala Ala
    210                 215                 220

Gly Tyr Glu Ala Val Asn Leu Ile Pro Arg Asn Val Leu Asn Leu Pro
225                 230                 235                 240

Arg Tyr Tyr Tyr Ser Gly Asn Asp Leu Gly Asn Val Tyr Ser Asn Lys
                245                 250                 255

Ala Thr Ala Phe Arg Val Trp Ala Pro Thr Ala Ser Asp Val Gln Leu
            260                 265                 270

Leu Leu Tyr Asn Ser Glu Thr Gly Pro Val Thr Lys Gln Leu Glu Met
        275                 280                 285

Gln Lys Ser Asp Asn Gly Thr Trp Lys Leu Lys Val Pro Gly Asn Leu
    290                 295                 300
```

-continued

```
Lys Asn Trp Tyr Tyr Leu Tyr Gln Val Thr Val Asn Gly Lys Thr Gln
305                 310                 315                 320

Thr Ala Val Asp Pro Tyr Val Arg Ala Ile Ser Val Asn Ala Thr Arg
            325                 330                 335

Gly Met Ile Val Asp Leu Glu Asp Thr Asn Pro Pro Gly Trp Lys Glu
                340                 345                 350

Asp His Gln Gln Thr Pro Ala Asn Pro Val Asp Glu Val Ile Tyr Glu
            355                 360                 365

Val His Val Arg Asp Phe Ser Ile Asp Ala Asn Ser Gly Met Lys Asn
        370                 375                 380

Lys Gly Lys Tyr Leu Ala Phe Thr Glu His Gly Thr Lys Gly Pro Asp
385                 390                 395                 400

Asn Val Lys Thr Gly Ile Asp Ser Leu Lys Glu Leu Gly Ile Asn Ala
                405                 410                 415

Val Gln Leu Gln Pro Ile Glu Glu Phe Asn Ser Ile Asp Glu Thr Gln
            420                 425                 430

Pro Asn Met Tyr Asn Trp Gly Tyr Asp Pro Arg Asn Tyr Asn Val Pro
        435                 440                 445

Glu Gly Ala Tyr Ala Thr Thr Pro Glu Gly Thr Ala Arg Ile Thr Gln
    450                 455                 460

Leu Lys Gln Leu Ile Gln Ser Ile His Lys Asp Arg Ile Ala Ile Asn
465                 470                 475                 480

Met Asp Val Val Tyr Asn His Thr Phe Asn Val Gly Val Ser Asp Phe
                485                 490                 495

Asp Lys Ile Val Pro Gln Tyr Tyr Arg Thr Asp Ser Ala Gly Asn
            500                 505                 510

Tyr Thr Asn Gly Ser Gly Val Gly Asn Glu Ile Ala Thr Glu Arg Pro
        515                 520                 525

Met Val Gln Lys Phe Val Leu Asp Ser Val Lys Tyr Trp Val Lys Glu
    530                 535                 540

Tyr His Ile Asp Gly Phe Arg Phe Asp Leu Met Ala Leu Leu Gly Lys
545                 550                 555                 560

Asp Thr Met Ala Lys Ile Ser Lys Glu Leu His Ala Ile Asn Pro Gly
                565                 570                 575

Ile Val Leu Tyr Gly Glu Pro Trp Thr Gly Gly Thr Ser Gly Leu Ser
            580                 585                 590

Ser Asp Gln Leu Val Thr Lys Gly Gln Gln Lys Gly Leu Gly Ile Gly
        595                 600                 605

Val Phe Asn Asp Asn Ile Arg Asn Gly Leu Asp Gly Asn Val Phe Asp
    610                 615                 620

Lys Ser Ala Gln Gly Phe Ala Thr Gly Asp Pro Asn Gln Val Asn Val
625                 630                 635                 640

Ile Lys Asn Arg Val Met Gly Ser Ile Ser Asp Phe Thr Ser Ala Pro
                645                 650                 655

Ser Glu Thr Ile Asn Tyr Val Thr Ser His Asp Asn Met Thr Leu Trp
            660                 665                 670

Asp Lys Ile Ser Ala Ser Asn Pro Asn Asp Thr Gln Ala Asp Arg Ile
        675                 680                 685

Lys Met Asp Glu Leu Ala Gln Ala Val Val Phe Thr Ser Gln Gly Val
    690                 695                 700

Pro Phe Met Gln Gly Gly Glu Glu Met Leu Arg Thr Lys Gly Gly Asn
705                 710                 715                 720

Asp Asn Ser Tyr Asn Ala Gly Asp Ser Val Asn Gln Phe Asp Trp Ser
```

```
                            725                 730                 735
Arg Lys Ala Gln Phe Glu Asn Val Phe Asp Tyr Tyr Ser Trp Leu Ile
            740                 745                 750

His Leu Arg Asp Asn His Pro Ala Phe Arg Met Thr Thr Ala Asp Gln
            755                 760                 765

Ile Lys Gln Asn Leu Thr Phe Leu Asp Ser Pro Thr Asn Thr Val Ala
            770                 775                 780

Phe Glu Leu Lys Asn His Ala Asn His Asp Lys Trp Lys Asn Ile Ile
785                 790                 795                 800

Val Met Tyr Asn Pro Asn Lys Thr Ala Gln Thr Leu Thr Leu Pro Ser
                805                 810                 815

Gly Asn Trp Thr Ile Val Gly Leu Gly Asn Gln Val Gly Glu Lys Ser
                820                 825                 830

Leu Gly His Val Asn Gly Thr Val Glu Val Pro Ala Leu Ser Thr Ile
            835                 840                 845

Ile Leu His Gln Gly Thr Ser Glu Asp Val Ile Asp Gln Asn
            850                 855                 860

<210> SEQ ID NO 2
<211> LENGTH: 915
<212> TYPE: PRT
<213> ORGANISM: Bacillus deramificans
<220> FEATURE:
<221> NAME/KEY: PEPTIDE
<222> LOCATION: (1)..(915)
<223> OTHER INFORMATION: Pullulanase

<400> SEQUENCE: 2

Asp Gly Asn Thr Thr Thr Ile Ile Val His Tyr Phe Arg Pro Ala Gly
1               5                   10                  15

Asp Tyr Gln Pro Trp Ser Leu Trp Met Trp Pro Lys Asp Gly Gly Gly
                20                  25                  30

Ala Glu Tyr Asp Phe Asn Gln Pro Ala Asp Ser Phe Gly Ala Val Ala
            35                  40                  45

Ser Ala Asp Ile Pro Gly Asn Pro Ser Gln Val Gly Ile Ile Val Arg
        50                  55                  60

Thr Gln Asp Trp Thr Lys Asp Val Ser Ala Asp Arg Tyr Ile Asp Leu
65                  70                  75                  80

Ser Lys Gly Asn Glu Val Trp Leu Val Glu Gly Asn Ser Gln Ile Phe
                85                  90                  95

Tyr Asn Glu Lys Asp Ala Glu Asp Ala Lys Pro Ala Val Ser Asn Ala
            100                 105                 110

Tyr Leu Asp Ala Ser Asn Gln Val Leu Val Lys Leu Ser Gln Pro Leu
        115                 120                 125

Thr Leu Gly Glu Gly Ala Ser Gly Phe Thr Val His Asp Asp Thr Ala
130                 135                 140

Asn Lys Asp Ile Pro Val Thr Ser Val Lys Asp Ala Ser Leu Gly Gln
                150                 155                 160

(Note: residues 145 Ala... through line appear as "Ala Asn Lys Asp Ile Pro Val Thr Ser Val Lys Asp Ala Ser Leu Gly" at position 145-160)

Asp Val Thr Ala Val Leu Ala Gly Thr Phe Gln His Ile Phe Gly Gly
            165                 170                 175

Ser Asp Trp Ala Pro Asp Asn His Ser Thr Leu Leu Lys Lys Val Thr
        180                 185                 190

Asn Asn Leu Tyr Gln Phe Ser Gly Asp Leu Pro Glu Gly Asn Tyr Gln
195                 200                 205

Tyr Lys Val Ala Met Ser His Ser Ala Gln Pro Val Thr Ser Val Gly
            210                 215                 220
```

```
Gln Ala Val Trp Pro Gly Arg Pro Tyr Pro Leu Gly Ala Thr Trp Asp
225                 230                 235                 240

Gly Leu Gly Val Asn Phe Ala Leu Tyr Ser Glu Ser Gly Val Lys Thr
            245                 250                 255

Asp Leu Val Thr Val Thr Leu Gly Glu Asp Pro Asp Val Ser His Thr
            260                 265                 270

Leu Ser Ile Gln Thr Asp Gly Tyr Gln Ala Lys Gln Val Ile Pro Arg
            275                 280                 285

Asn Val Leu Asn Ser Ser Gln Tyr Tyr Ser Gly Asp Asp Leu Gly
            290                 295                 300

Asn Thr Tyr Thr Gln Lys Ala Thr Thr Phe Lys Val Trp Ala Pro Thr
305                 310                 315                 320

Ser Thr Gln Val Asn Val Leu Leu Tyr Asp Ser Ala Thr Gly Ser Val
            325                 330                 335

Thr Lys Ile Val Pro Met Thr Ala Ser Gly His Gly Val Trp Glu Ala
            340                 345                 350

Thr Val Asn Gln Asn Leu Glu Asn Trp Tyr Tyr Met Tyr Glu Val Thr
            355                 360                 365

Gly Gln Gly Ser Thr Arg Thr Ala Val Asp Pro Tyr Ala Thr Ala Ile
            370                 375                 380

Ala Pro Asn Gly Thr Arg Gly Met Ile Val Asp Leu Ala Lys Thr Asp
385                 390                 395                 400

Pro Ala Gly Trp Asn Ser Asp Lys His Ile Thr Pro Lys Asn Ile Glu
            405                 410                 415

Asp Glu Val Ile Tyr Glu Met Asp Val Arg Asp Phe Ser Ile Asp Pro
            420                 425                 430

Asn Ser Gly Met Lys Asn Lys Gly Lys Tyr Leu Ala Leu Thr Glu Lys
            435                 440                 445

Gly Thr Lys Gly Pro Asp Asn Val Lys Thr Gly Ile Asp Ser Leu Lys
450                 455                 460

Gln Leu Gly Ile Thr His Val Gln Leu Met Pro Val Phe Ala Ser Asn
465                 470                 475                 480

Ser Val Asp Glu Thr Asp Pro Thr Gln Asp Asn Trp Gly Tyr Asp Pro
            485                 490                 495

Arg Asn Tyr Asp Val Pro Glu Gly Gln Tyr Ala Thr Asn Ala Asn Gly
            500                 505                 510

Asn Ala Arg Ile Lys Glu Phe Lys Glu Met Val Leu Ser Leu His Arg
            515                 520                 525

Glu His Ile Gly Val Asn Met Asp Val Val Tyr Asn His Thr Phe Ala
            530                 535                 540

Thr Gln Ile Ser Asp Phe Asp Lys Ile Val Pro Glu Tyr Tyr Tyr Arg
545                 550                 555                 560

Thr Asp Asp Ala Gly Asn Tyr Thr Asn Gly Ser Gly Thr Gly Asn Glu
            565                 570                 575

Ile Ala Ala Glu Arg Pro Met Val Gln Lys Phe Ile Ile Asp Ser Leu
            580                 585                 590

Lys Tyr Trp Val Asn Glu Tyr His Ile Asp Gly Phe Arg Phe Asp Leu
            595                 600                 605

Met Ala Leu Leu Gly Lys Asp Thr Met Ser Lys Ala Ala Ser Glu Leu
            610                 615                 620

His Ala Ile Asn Pro Gly Ile Ala Leu Tyr Gly Glu Pro Trp Thr Gly
625                 630                 635                 640
```

```
Gly Thr Ser Ala Leu Pro Asp Gln Leu Leu Thr Lys Gly Ala Gln
                645                 650                 655

Lys Gly Met Gly Val Ala Val Phe Asn Asp Asn Leu Arg Asn Ala Leu
            660                 665                 670

Asp Gly Asn Val Phe Asp Ser Ser Ala Gln Gly Phe Ala Thr Gly Ala
        675                 680                 685

Thr Gly Leu Thr Asp Ala Ile Lys Asn Gly Val Glu Gly Ser Ile Asn
    690                 695                 700

Asp Phe Thr Ser Ser Pro Gly Glu Thr Ile Asn Tyr Val Thr Ser His
705                 710                 715                 720

Asp Asn Tyr Thr Leu Trp Asp Lys Ile Ala Leu Ser Asn Pro Asn Asp
                725                 730                 735

Ser Glu Ala Asp Arg Ile Lys Met Asp Glu Leu Ala Gln Ala Val Val
            740                 745                 750

Met Thr Ser Gln Gly Val Pro Phe Met Gln Gly Gly Glu Glu Met Leu
        755                 760                 765

Arg Thr Lys Gly Gly Asn Asp Asn Ser Tyr Asn Ala Gly Asp Ala Val
    770                 775                 780

Asn Glu Phe Asp Trp Ser Arg Lys Ala Gln Tyr Pro Asp Val Phe Asn
785                 790                 795                 800

Tyr Tyr Ser Gly Leu Ile His Leu Arg Leu Asp His Pro Ala Phe Arg
                805                 810                 815

Met Thr Thr Ala Asn Glu Ile Asn Ser His Leu Gln Phe Leu Asn Ser
            820                 825                 830

Pro Glu Asn Thr Val Ala Tyr Glu Leu Thr Asp His Val Asn Lys Asp
        835                 840                 845

Lys Trp Gly Asn Ile Ile Val Val Tyr Asn Pro Asn Lys Thr Val Ala
    850                 855                 860

Thr Ile Asn Leu Pro Ser Gly Lys Trp Ala Ile Asn Ala Thr Ser Gly
865                 870                 875                 880

Lys Val Gly Glu Ser Thr Leu Gly Gln Ala Glu Gly Ser Val Gln Val
                885                 890                 895

Pro Gly Ile Ser Met Met Ile Leu His Gln Glu Val Ser Pro Asp His
            900                 905                 910

Gly Lys Lys
        915

<210> SEQ ID NO 3
<211> LENGTH: 726
<212> TYPE: PRT
<213> ORGANISM: Rhodotermus marinus
<220> FEATURE:
<221> NAME/KEY: PEPTIDE
<222> LOCATION: (1)..(726)
<223> OTHER INFORMATION: Isoamylase

<400> SEQUENCE: 3

Met Ser His Ser Ala Gln Pro Val Thr Ser Val Gln Ala Val Trp Pro
1               5                   10                  15

Gly Arg Pro Tyr Pro Leu Gly Ala Thr Trp Asp Gly Leu Gly Val Asn
            20                  25                  30

Phe Ala Leu Tyr Ser Gln His Ala Glu Ala Val Glu Leu Val Leu Phe
        35                  40                  45

Asp His Pro Asp Asp Pro Ala Pro Ser Arg Thr Ile Glu Val Thr Glu
    50                  55                  60

Arg Thr Gly Pro Ile Trp His Val Tyr Leu Pro Gly Leu Arg Pro Gly
```

-continued

```
            65                  70                  75                  80
Gln Leu Tyr Gly Tyr Arg Val Tyr Gly Pro Tyr Arg Pro Glu Glu Gly
                    85                  90                  95
His Arg Phe Asn Pro Asn Lys Val Leu Leu Asp Pro Tyr Ala Lys Ala
                100                 105                 110
Ile Gly Arg Pro Leu Arg Trp His Asp Ser Leu Phe Gly Tyr Lys Ile
            115                 120                 125
Gly Asp Pro Ala Gly Asp Leu Ser Phe Ser Glu Glu Asp Ser Ala Pro
        130                 135                 140
Tyr Ala Pro Leu Gly Ala Val Val Glu Gly Cys Phe Glu Trp Gly Asp
145                 150                 155                 160
Asp Arg Pro Pro Arg Ile Pro Trp Glu Asp Thr Ile Ile Tyr Glu Thr
                165                 170                 175
His Val Lys Gly Ile Thr Lys Leu His Pro Glu Val Pro Glu Pro Leu
                180                 185                 190
Arg Gly Thr Tyr Leu Gly Leu Thr Cys Glu Pro Val Leu Glu His Leu
            195                 200                 205
Lys Gln Leu Gly Val Thr Thr Ile Gln Leu Leu Pro Val His Ala Lys
        210                 215                 220
Val His Asp Arg His Leu Val Glu Arg Gly Leu Arg Asn Tyr Trp Gly
225                 230                 235                 240
Tyr Asn Pro Leu Cys Tyr Phe Ala Pro Glu Pro Glu Tyr Ala Thr Asn
                245                 250                 255
Gly Pro Ile Ser Ala Val Arg Glu Phe Lys Met Met Val Arg Ala Leu
                260                 265                 270
His Ala Ala Gly Phe Glu Val Ile Val Asp Val Val Tyr Asn His Thr
            275                 280                 285
Gly Glu Gly Gly Val Leu Gly Pro Thr Leu Ser Phe Arg Gly Ile Asp
        290                 295                 300
Asn Arg Ala Tyr Tyr Lys Ala Asp Pro Asn Asn Pro Arg Phe Leu Val
305                 310                 315                 320
Asp Tyr Thr Gly Thr Gly Asn Thr Leu Asp Val Gly Asn Pro Tyr Val
                325                 330                 335
Ile Gln Leu Ile Met Asp Ser Leu Arg Tyr Trp Val Thr Glu Met His
                340                 345                 350
Val Asp Gly Phe Arg Phe Asp Leu Ala Ala Ala Leu Ala Arg Glu Leu
            355                 360                 365
Tyr Asp Val Asp Met Leu Ser Thr Phe Gln Val Ile Gln Gln Asp
        370                 375                 380
Pro Val Leu Ser Gln Val Lys Leu Ile Ala Glu Pro Trp Asp Val Gly
385                 390                 395                 400
Pro Gly Gly Tyr Gln Val Gly His Phe Pro Trp Gln Trp Thr Glu Trp
                405                 410                 415
Asn Gly Arg Tyr Arg Asp Ala Val Arg Arg Phe Trp Arg Gly Asp Arg
                420                 425                 430
Gly Leu Asn Gly Glu Phe Ala Thr Arg Phe Ala Gly Ser Ser Asp Leu
            435                 440                 445
Tyr Glu Arg Ser Gly Arg Arg Pro Phe Ala Ser Ile Asn Phe Val Thr
        450                 455                 460
Ala His Asp Gly Phe Thr Leu Glu Asp Leu Val Ser Tyr Thr Lys Lys
465                 470                 475                 480
His Asn Glu Ala Asn Leu Glu Gly Asn Arg Asp Gly Met Asp Glu Asn
                485                 490                 495
```

-continued

```
Tyr Ser Thr Asn Cys Gly Val Glu Gly Pro Thr Gln Asp Pro Ser Val
            500                 505                 510

Leu Ala Cys Arg Glu Ala Leu Lys Arg Ser Leu Ile Ser Thr Leu Phe
            515                 520                 525

Leu Ser Gln Gly Val Pro Met Leu Leu Gly Gly Asp Glu Leu Ser Arg
            530                 535                 540

Thr Gln His Gly Asn Asn Asn Ala Tyr Cys Gln Asp Asn Glu Ile Ser
545                 550                 555                 560

Trp Tyr Asn Trp Gln Leu Asp Thr Arg Lys Gln Gln Phe Leu Glu Phe
                565                 570                 575

Val Arg Gln Thr Ile Trp Phe Arg Lys Gln His Arg Ser Phe Arg Arg
            580                 585                 590

Arg His Phe Leu Thr Gly Leu Pro Asn Gly Gly Arg Pro Arg Arg Ser
            595                 600                 605

Leu Val Ala Pro Glu Gly Arg Pro Met Arg His Glu Asp Trp Thr Asn
            610                 615                 620

Pro Glu Leu Thr Ala Phe Gly Leu Leu Leu His Gly Asp Ala Ile Gln
625                 630                 635                 640

Gly Thr Asp Glu His Gly Arg Pro Phe Arg Asp Asp Thr Phe Leu Ile
                645                 650                 655

Leu Phe Asn Asn Gly Ser Glu Ala Val Pro Val Val Pro Glu Val
            660                 665                 670

Cys Ser Cys Gly Lys Pro His His Trp Glu Val Val Pro Val Phe Gln
            675                 680                 685

Arg Asn Val Glu Pro Pro Thr Cys Ala Pro Gly Glu Thr Leu Ser Leu
            690                 695                 700

Pro Pro Gly Val Leu Thr Val Leu Val Ala Val Pro Pro Phe Ser Asp
705                 710                 715                 720

Gly Asn Thr Glu Pro Ala
                725

<210> SEQ ID NO 4
<211> LENGTH: 776
<212> TYPE: PRT
<213> ORGANISM: Pseudomonas amyloderamosa
<220> FEATURE:
<221> NAME/KEY: PEPTIDE
<222> LOCATION: (1)..(776)
<223> OTHER INFORMATION: Isoamylase

<400> SEQUENCE: 4

Met Lys Cys Pro Lys Ile Leu Ala Ala Leu Leu Gly Cys Ala Val Leu
1               5                   10                  15

Ala Gly Val Pro Ala Met Pro Ala His Ala Ala Ile Asn Ser Met Ser
            20                  25                  30

Leu Gly Ala Ser Tyr Asp Ala Gln Gln Ala Asn Ile Thr Phe Arg Val
        35                  40                  45

Tyr Ser Ser Gln Ala Thr Arg Ile Val Leu Tyr Leu Tyr Ser Ala Gly
    50                  55                  60

Tyr Gly Val Gln Glu Ser Ala Thr Tyr Thr Leu Ser Pro Ala Gly Ser
65                  70                  75                  80

Gly Val Trp Ala Val Thr Val Pro Val Ser Ser Ile Lys Ala Ala Gly
                85                  90                  95

Ile Thr Gly Ala Val Tyr Tyr Gly Tyr Arg Ala Trp Gly Pro Asn Trp
            100                 105                 110
```

```
Pro Tyr Ala Ser Asn Trp Gly Lys Gly Ser Gln Ala Gly Phe Val Ser
        115                 120                 125

Asp Val Asp Ala Asn Gly Asp Arg Phe Asn Pro Asn Lys Leu Leu Leu
130                 135                 140

Asp Pro Tyr Ala Gln Glu Val Ser Gln Asp Pro Leu Asn Pro Ser Asn
145                 150                 155                 160

Gln Asn Gly Asn Val Phe Ala Ser Gly Ala Ser Tyr Arg Thr Thr Asp
                165                 170                 175

Ser Gly Ile Tyr Ala Pro Lys Gly Val Val Leu Val Pro Ser Thr Gln
            180                 185                 190

Ser Thr Gly Thr Lys Pro Thr Arg Ala Gln Lys Asp Asp Val Ile Tyr
        195                 200                 205

Glu Val His Val Arg Gly Phe Thr Glu Gln Asp Thr Ser Ile Pro Ala
    210                 215                 220

Gln Tyr Arg Gly Thr Tyr Tyr Gly Ala Gly Leu Lys Ala Ser Tyr Leu
225                 230                 235                 240

Ala Ser Leu Gly Val Thr Ala Val Glu Phe Leu Pro Val Gln Glu Thr
                245                 250                 255

Gln Asn Asp Ala Asn Asp Val Val Pro Asn Ser Asp Ala Asn Gln Asn
            260                 265                 270

Tyr Trp Gly Tyr Met Thr Glu Asn Tyr Phe Ser Pro Asp Arg Arg Tyr
        275                 280                 285

Ala Tyr Asn Lys Ala Ala Gly Gly Pro Thr Ala Glu Phe Gln Ala Met
    290                 295                 300

Val Gln Ala Phe His Asn Ala Gly Ile Lys Val Tyr Met Asp Val Val
305                 310                 315                 320

Tyr Asn His Thr Ala Glu Gly Gly Thr Trp Thr Ser Ser Asp Pro Thr
                325                 330                 335

Thr Ala Thr Ile Tyr Ser Trp Arg Gly Leu Asp Asn Ala Thr Tyr Tyr
            340                 345                 350

Glu Leu Thr Ser Gly Asn Gln Tyr Phe Tyr Asp Asn Thr Gly Ile Gly
        355                 360                 365

Ala Asn Phe Asn Thr Tyr Asn Thr Val Ala Gln Asn Leu Ile Val Asp
    370                 375                 380

Ser Leu Ala Tyr Trp Ala Asn Thr Met Gly Val Asp Gly Phe Arg Phe
385                 390                 395                 400

Asp Leu Ala Ser Val Leu Gly Asn Ser Cys Leu Asn Gly Ala Tyr Thr
                405                 410                 415

Ala Ser Ala Pro Asn Cys Pro Asn Gly Gly Tyr Asn Phe Asp Ala Ala
            420                 425                 430

Asp Ser Asn Val Ala Ile Asn Arg Ile Leu Arg Glu Phe Thr Val Arg
        435                 440                 445

Pro Ala Ala Gly Gly Ser Gly Leu Asp Leu Phe Ala Glu Pro Trp Ala
    450                 455                 460

Ile Gly Gly Asn Ser Tyr Gln Leu Gly Gly Phe Pro Gln Gly Trp Ser
465                 470                 475                 480

Glu Trp Asn Gly Leu Phe Arg Asp Ser Leu Arg Gln Ala Gln Asn Glu
                485                 490                 495

Leu Gly Ser Met Thr Ile Tyr Val Ile Gln Asp Ala Asn Asp Phe Ser
            500                 505                 510

Gly Ser Ser Asn Leu Phe Gln Ser Ser Gly Arg Ser Pro Trp Asn Ser
        515                 520                 525

Ile Asn Phe Ile Asp Val His Asp Gly Met Thr Leu Lys Asp Val Tyr
```

-continued

```
               530                 535                 540
Ser Cys Asn Gly Ala Asn Asn Ser Gln Ala Trp Pro Tyr Gly Pro Ser
545                 550                 555                 560

Asp Gly Gly Thr Ser Thr Asn Tyr Ser Trp Asp Gln Gly Met Ser Ala
                565                 570                 575

Gly Thr Gly Ala Ala Val Asp Gln Arg Arg Ala Ala Arg Thr Gly Met
            580                 585                 590

Ala Phe Glu Met Leu Ser Ala Gly Thr Pro Leu Met Gln Gly Gly Asp
        595                 600                 605

Glu Tyr Leu Arg Thr Leu Gln Cys Asn Asn Ala Tyr Asn Leu Asp
    610                 615                 620

Ser Ser Ala Asn Trp Leu Thr Tyr Ser Trp Thr Thr Asp Gln Ser Asn
625                 630                 635                 640

Phe Tyr Thr Phe Ala Gln Arg Leu Ile Ala Phe Arg Lys Ala His Pro
                645                 650                 655

Ala Leu Arg Pro Ser Ser Trp Tyr Ser Gly Ser Gln Leu Thr Trp Tyr
            660                 665                 670

Gln Pro Ser Gly Ala Val Ala Asp Ser Asn Tyr Trp Asn Asn Thr Ser
        675                 680                 685

Asn Tyr Ala Ile Ala Tyr Ala Ile Asn Gly Pro Ser Leu Gly Asp Ser
    690                 695                 700

Asn Ser Ile Tyr Val Ala Tyr Asn Gly Trp Ser Ser Val Thr Phe
705                 710                 715                 720

Thr Leu Pro Ala Pro Ser Gly Thr Gln Trp Tyr Arg Val Thr Asp
                725                 730                 735

Thr Cys Asp Trp Asn Asp Gly Ala Ser Thr Phe Val Ala Pro Gly Ser
            740                 745                 750

Glu Thr Leu Ile Gly Gly Ala Gly Thr Thr Tyr Gly Gln Cys Gly Gln
        755                 760                 765

Ser Leu Leu Leu Leu Ile Ser Lys
    770                 775
```

```
<210> SEQ ID NO 5
<211> LENGTH: 1090
<212> TYPE: PRT
<213> ORGANISM: Klebsiella pneumoniae
<220> FEATURE:
<221> NAME/KEY: PEPTIDE
<222> LOCATION: (1)..(1090)
<223> OTHER INFORMATION: pullulanase

<400> SEQUENCE: 5
```

```
Met Leu Arg Tyr Thr Arg Asn Ala Leu Val Leu Gly Ser Leu Val Leu
1               5                   10                  15

Leu Ser Gly Cys Asp Asn Gly Ser Ser Ser Ser Ser Gly Asn Pro
                20                  25                  30

Asp Thr Pro Asp Asn Gln Asp Val Val Arg Leu Pro Asp Val Ala
            35                  40                  45

Val Pro Gly Glu Ala Val Thr Ala Val Glu Asn Gln Ala Val Ile His
        50                  55                  60

Leu Val Asp Ile Ala Gly Ile Thr Ser Ser Ala Ala Asp Tyr Ser
65              70                  75                  80

Ser Lys Asn Leu Tyr Leu Trp Asn Asn Glu Thr Cys Asp Ala Leu Ser
                85                  90                  95

Ala Pro Val Ala Asp Trp Asn Asp Val Ser Thr Thr Pro Ser Gly Ser
            100                 105                 110
```

-continued

```
Asp Lys Tyr Gly Pro Tyr Trp Val Ile Pro Leu Asn Lys Glu Ser Gly
        115                 120                 125

Cys Ile Asn Val Ile Val Arg Asp Gly Thr Asp Lys Leu Ile Asp Ser
        130                 135             140

Asp Leu Arg Val Ala Phe Gly Asp Phe Thr Asp Arg Thr Val Ser Val
145                 150                 155                 160

Ile Ala Gly Asn Ser Ala Val Tyr Asp Ser Arg Ala Asp Ala Phe Arg
                165                 170                 175

Ala Ala Phe Gly Val Ala Leu Ala Glu Ala His Trp Val Asp Lys Asn
                180                 185                 190

Thr Leu Leu Trp Pro Gly Gly Gln Asp Lys Pro Ile Val Arg Leu Tyr
            195                 200                 205

Tyr Ser His Ser Ser Lys Val Ala Ala Asp Gly Glu Gly Lys Phe Thr
        210                 215                 220

Asp Arg Tyr Leu Lys Leu Thr Pro Thr Thr Val Ser Gln Gln Val Ser
225                 230                 235                 240

Met Arg Phe Pro His Leu Ser Ser Tyr Ala Ala Phe Lys Leu Pro Asp
                245                 250                 255

Asn Ala Asn Val Asp Glu Leu Leu Gln Gly Glu Thr Val Ala Ile Ala
                260                 265                 270

Ala Ala Glu Asp Gly Ile Leu Ile Ser Ala Thr Gln Val Gln Thr Ala
            275                 280                 285

Gly Val Leu Asp Asp Ala Tyr Ala Glu Ala Ala Glu Ala Leu Ser Tyr
        290                 295                 300

Gly Ala Gln Leu Ala Asp Gly Gly Val Thr Phe Arg Val Trp Ala Pro
305                 310                 315                 320

Thr Ala Gln Gln Val Asp Val Val Tyr Ser Ala Asp Lys Lys Val
                325                 330                 335

Ile Gly Ser His Pro Met Thr Arg Asp Ser Ala Ser Gly Ala Trp Ser
                340                 345                 350

Trp Gln Gly Gly Ser Asp Leu Lys Gly Ala Phe Tyr Arg Tyr Ala Met
            355                 360                 365

Thr Val Tyr His Pro Gln Ser Arg Lys Val Glu Gln Tyr Glu Val Thr
        370                 375                 380

Asp Pro Tyr Ala His Ser Leu Ser Thr Asn Ser Glu Tyr Ser Gln Val
385                 390                 395                 400

Val Asp Leu Asn Asp Ser Ala Leu Lys Pro Asp Gly Trp Asp Asn Leu
                405                 410                 415

Thr Met Pro His Ala Gln Lys Thr Lys Ala Asp Leu Ala Lys Met Thr
            420                 425                 430

Ile His Glu Ser His Ile Arg Asp Leu Ser Ala Trp Asp Gln Thr Val
        435                 440                 445

Pro Ala Glu Leu Arg Gly Lys Tyr Leu Ala Leu Thr Ala Gly Asp Ser
        450                 455                 460

Asn Met Val Gln His Leu Lys Thr Leu Ser Ala Ser Gly Val Thr His
465                 470                 475                 480

Val Glu Leu Leu Pro Val Phe Asp Leu Ala Thr Val Asn Glu Phe Ser
                485                 490                 495

Asp Lys Val Ala Asp Ile Gln Gln Pro Phe Ser Arg Leu Cys Glu Val
                500                 505                 510

Asn Ser Ala Val Lys Ser Ser Glu Phe Ala Gly Tyr Cys Asp Ser Gly
            515                 520                 525
```

```
Ser Thr Val Glu Glu Val Leu Asn Gln Leu Lys Gln Ser Asp Ser Gln
    530                 535                 540

Asp Asn Pro Gln Val Gln Ala Leu Asn Thr Leu Val Ala Gln Thr Asp
545                 550                 555                 560

Ser Tyr Asn Trp Gly Tyr Asp Pro Phe His Tyr Thr Val Pro Glu Gly
                565                 570                 575

Ser Tyr Ala Thr Asp Pro Glu Gly Thr Thr Arg Ile Lys Glu Phe Arg
                580                 585                 590

Thr Met Ile Gln Ala Ile Lys Gln Asp Leu Gly Met Asn Val Ile Met
            595                 600                 605

Asp Val Val Tyr Asn His Thr Asn Ala Ala Gly Pro Thr Asp Arg Thr
    610                 615                 620

Ser Val Leu Asp Lys Ile Val Pro Trp Tyr Tyr Gln Arg Leu Asn Glu
625                 630                 635                 640

Thr Thr Gly Ser Val Glu Ser Ala Thr Cys Cys Ser Asp Ser Ala Pro
                645                 650                 655

Glu His Arg Met Phe Ala Lys Leu Ile Ala Asp Ser Leu Ala Val Trp
                660                 665                 670

Thr Thr Asp Tyr Lys Ile Asp Gly Phe Arg Phe Asp Leu Met Gly Tyr
            675                 680                 685

His Pro Lys Ala Gln Ile Leu Ser Ala Trp Glu Arg Ile Lys Ala Leu
    690                 695                 700

Asn Pro Asp Ile Tyr Phe Phe Gly Glu Gly Trp Asp Ser Asn Gln Ser
705                 710                 715                 720

Asp Arg Phe Glu Ile Ala Ser Gln Ile Asn Leu Lys Gly Thr Gly Ile
                725                 730                 735

Gly Thr Phe Ser Asp Arg Leu Arg Asp Ser Val Arg Gly Gly Gly Pro
            740                 745                 750

Phe Asp Ser Gly Asp Ala Leu Arg Gln Asn Gln Gly Ile Gly Ser Gly
    755                 760                 765

Ala Gly Val Leu Pro Asn Glu Leu Ala Ser Leu Ser Asp Asp Gln Val
    770                 775                 780

Arg His Leu Ala Asp Leu Thr Arg Leu Gly Met Ala Gly Asn Leu Ala
785                 790                 795                 800

Asp Phe Val Met Ile Asp Lys Asp Gly Ala Ala Lys Lys Gly Ser Glu
                805                 810                 815

Ile Asp Tyr Asn Gly Ala Pro Gly Gly Tyr Ala Ala Asp Pro Thr Glu
                820                 825                 830

Val Val Asn Tyr Val Ser Lys His Asp Asn Gln Thr Leu Trp Asp Met
            835                 840                 845

Ile Ser Tyr Lys Ala Ser Gln Glu Ala Asp Leu Ala Thr Arg Val Arg
    850                 855                 860

Met Gln Ala Val Ser Leu Ala Thr Val Met Leu Gly Gln Gly Ile Ala
865                 870                 875                 880

Phe Asp Gln Gln Gly Ser Glu Leu Leu Arg Ser Lys Ser Phe Thr Arg
                885                 890                 895

Asp Ser Tyr Asp Ser Gly Asp Trp Phe Asn Arg Val Asp Tyr Ser Leu
                900                 905                 910

Gln Asp Asn Asn Tyr Asn Val Gly Met Pro Arg Ile Ser Asp Asp Gly
            915                 920                 925

Ser Asn Tyr Glu Val Ile Thr Arg Val Lys Glu Met Val Ala Thr Pro
    930                 935                 940

Gly Glu Ala Glu Leu Lys Gln Met Thr Ala Phe Tyr Gln Glu Leu Thr
```

```
                945                 950                 955                 960
Glu Leu Arg Lys Ser Ser Pro Leu Phe Thr Leu Gly Asp Gly Ser Ala
            965                 970                 975

Val Met Lys Arg Val Asp Phe Arg Asn Thr Gly Ser Asp Gln Gln Ala
            980                 985                 990

Gly Leu Leu Val Met Thr Val Asp Asp Gly Met Lys Ala Gly Ala Ser
            995                1000                1005

Leu Asp Ser Arg Leu Asp Gly Leu Val Val Ala Ile Asn Ala Ala Pro
   1010                1015                1020

Glu Ser Arg Thr Leu Asn Glu Phe Ala Gly Glu Thr Leu Gln Leu Ser
1025                1030                1035                1040

Ala Ile Gln Gln Thr Ala Gly Glu Asn Ser Leu Ala Asn Gly Val Gln
            1045                1050                1055

Ile Ala Ala Asp Gly Thr Val Thr Leu Pro Ala Trp Ser Val Ala Val
            1060                1065                1070

Leu Glu Leu Pro Gln Gly Glu Ala Gln Gly Ala Gly Leu Pro Val Ser
        1075                1080                1085

Ser Lys
   1090

<210> SEQ ID NO 6
<211> LENGTH: 1096
<212> TYPE: PRT
<213> ORGANISM: Klebsiella aerogenes
<220> FEATURE:
<221> NAME/KEY: PEPTIDE
<222> LOCATION: (1)..(1096)
<223> OTHER INFORMATION: Pullulanase

<400> SEQUENCE: 6

Met Leu Arg Tyr Thr Cys His Ala Leu Phe Leu Gly Ser Leu Val Leu
  1               5                  10                  15

Leu Ser Gly Cys Asp Asn Ser Ser Ser Ser Thr Ser Gly Ser Pro
                 20                  25                  30

Gly Ser Pro Gly Asn Pro Gly Asn Pro Gly Thr Pro Gly Thr Pro Asp
             35                  40                  45

Pro Gln Asp Val Val Arg Leu Pro Asp Val Ala Val Pro Gly Glu
         50                  55                  60

Ala Val Gln Ala Ser Ala Arg Gln Ala Val Ile His Leu Val Asp Ile
 65                  70                  75                  80

Ala Gly Ile Thr Ser Ser Pro Ala Asp Tyr Ala Thr Lys Asn Leu
                 85                  90                  95

Tyr Leu Trp Asn Asn Glu Thr Cys Asp Ala Leu Ser Ala Pro Val Ala
                100                 105                 110

Asp Trp Asn Asp Val Ser Thr Thr Pro Thr Gly Ser Asp Lys Tyr Gly
            115                 120                 125

Pro Tyr Trp Val Ile Pro Leu Thr Lys Glu Ser Gly Ser Ile Asn Val
        130                 135                 140

Ile Val Arg Asp Gly Thr Asn Lys Leu Ile Asp Ser Gly Arg Val Ser
145                 150                 155                 160

Phe Ser Asp Phe Thr Asp Arg Thr Val Ser Val Ile Ala Gly Asn Ser
                165                 170                 175

Ala Val Tyr Asp Ser Arg Ala Asp Ala Phe Arg Ala Ala Phe Gly Val
            180                 185                 190

Ala Leu Ala Asp Ala His Trp Val Asp Lys Thr Thr Leu Leu Trp Pro
        195                 200                 205
```

-continued

Gly Gly Glu Asn Lys Pro Ile Val Arg Leu Tyr Tyr Ser His Ser Ser
        210             215                 220

Lys Val Ala Ala Asp Ser Asn Gly Glu Phe Ser Asp Lys Tyr Val Lys
225             230                 235                 240

Leu Thr Pro Thr Thr Val Asn Gln Gln Val Ser Met Arg Phe Pro His
            245                 250                 255

Leu Ala Ser Tyr Pro Ala Phe Lys Leu Pro Asp Asp Val Asn Val Asp
        260                 265                 270

Glu Leu Leu Gln Gly Asp Asp Gly Ile Ala Glu Ser Asp Gly Ile
        275                 280                 285

Leu Ser Leu Ser His Pro Gly Ala Asp Arg Arg Ala Gly Arg Tyr
        290                 295                 300

Leu Cys Arg Arg Ala Glu Ala Leu Ser Tyr Gly Ala Gln Leu Thr Asp
305             310                 315                 320

Ser Gly Val Thr Phe Arg Val Trp Ala Pro Thr Ala Gln Gln Val Glu
            325                 330                 335

Leu Val Ile Tyr Ser Ala Asp Lys Lys Val Ile Ala Ser His Pro Met
            340                 345                 350

Thr Arg Asp Ser Ala Ser Gly Ala Trp Ser Trp Gln Gly Gly Ser Asp
        355                 360                 365

Leu Lys Gly Ala Phe Tyr Arg Tyr Ala Met Thr Val Tyr His Pro Gln
        370                 375                 380

Ser Arg Lys Val Glu Gln Tyr Glu Val Thr Asp Pro Tyr Ala His Ser
385             390                 395                 400

Leu Ser Thr Asn Ser Glu Tyr Ser Gln Val Val Asp Leu Asn Asp Ser
            405                 410                 415

Ala Leu Lys Pro Glu Gly Trp Asp Gly Leu Thr Met Pro His Ala Gln
        420                 425                 430

Lys Thr Lys Ala Asp Leu Ala Lys Met Thr Ile His Glu Ser His Ile
        435                 440                 445

Arg Asp Leu Ser Ala Trp Asp Gln Thr Val Pro Ala Glu Leu Arg Gly
450             455                 460

Lys Tyr Leu Ala Leu Thr Ala Gln Glu Ser Asn Met Val Gln His Leu
465             470                 475                 480

Lys Gln Leu Ser Ala Ser Gly Val Thr His Ile Glu Leu Leu Pro Val
            485                 490                 495

Phe Asp Leu Ala Thr Val Asn Glu Phe Ser Asp Lys Val Ala Asp Ile
            500                 505                 510

Gln Gln Pro Phe Ser Arg Leu Cys Glu Val Asn Ser Ala Val Lys Ser
        515                 520                 525

Ser Glu Phe Ala Gly Tyr Cys Asp Ser Gly Ser Thr Val Glu Glu Val
        530                 535                 540

Leu Thr Gln Leu Lys Gln Asn Asp Ser Lys Asp Asn Pro Gln Val Gln
545             550                 555                 560

Ala Leu Asn Thr Leu Val Ala Gln Thr Asp Ser Tyr Asn Trp Gly Tyr
            565                 570                 575

Asp Pro Phe His Tyr Thr Val Pro Glu Gly Ser Tyr Ala Thr Asp Pro
            580                 585                 590

Glu Gly Thr Ala Arg Ile Lys Glu Phe Arg Thr Met Ile Gln Ala Ile
        595                 600                 605

Lys Gln Asp Leu Gly Met Asn Val Ile Met Asp Val Val Tyr Asn His
        610                 615                 620

```
Thr Asn Ala Ala Gly Pro Thr Asp Arg Thr Ser Val Leu Asp Lys Ile
625                 630                 635                 640

Val Pro Trp Tyr Tyr Gln Arg Leu Asn Glu Thr Thr Gly Ser Val Glu
                645                 650                 655

Ser Ala Thr Cys Cys Ser Asp Ser Ala Pro Glu His Arg Met Phe Ala
            660                 665                 670

Lys Leu Ile Ala Asp Ser Leu Ala Val Trp Thr Thr Asp Tyr Lys Ile
        675                 680                 685

Asp Gly Phe Arg Phe Asp Leu Met Gly Tyr His Pro Lys Ala Gln Ile
    690                 695                 700

Leu Ser Ala Trp Glu Arg Ile Lys Ala Leu Asn Pro Asp Ile Tyr Phe
705                 710                 715                 720

Phe Gly Glu Gly Trp Asp Ser Asn Gln Ser Asp Arg Phe Glu Ile Ala
                725                 730                 735

Ser Gln Ile Asn Leu Lys Gly Thr Gly Ile Gly Thr Phe Ser Asp Arg
            740                 745                 750

Leu Arg Asp Ala Val Arg Gly Gly Pro Phe Asp Ser Gly Asp Ala
        755                 760                 765

Leu Arg Gln Asn Gln Gly Val Gly Ser Gly Ala Gly Val Leu Pro Asn
    770                 775                 780

Glu Leu Thr Thr Leu Ser Asp Asp Gln Ala Arg His Leu Ala Asp Leu
785                 790                 795                 800

Thr Arg Leu Gly Met Ala Gly Asn Leu Ala Asp Phe Val Leu Ile Asp
                805                 810                 815

Lys Asp Gly Ala Val Lys Arg Gly Ser Glu Ile Asp Tyr Asn Gly Ala
            820                 825                 830

Pro Gly Gly Tyr Ala Ala Asp Pro Thr Glu Val Val Asn Tyr Val Ser
        835                 840                 845

Lys His Asp Asn Gln Thr Leu Trp Asp Met Ile Ser Tyr Lys Ala Ala
    850                 855                 860

Gln Glu Ala Asp Leu Asp Thr Arg Val Arg Met Gln Ala Val Ser Leu
865                 870                 875                 880

Ala Thr Val Met Leu Gly Gln Gly Ile Ala Phe Asp Gln Gln Gly Ser
                885                 890                 895

Glu Leu Leu Arg Ser Lys Ser Phe Thr Arg Asp Ser Tyr Asp Ser Gly
            900                 905                 910

Asp Trp Phe Asn Arg Val Asp Tyr Ser Leu Gln Asp Asn Asn Tyr Asn
        915                 920                 925

Val Gly Met Pro Arg Ser Ser Asp Gly Ser Asn Tyr Asp Ile Ile
    930                 935                 940

Ala Arg Val Lys Asp Ala Val Ala Thr Pro Gly Glu Thr Glu Leu Lys
945                 950                 955                 960

Gln Met Thr Ala Phe Tyr Gln Glu Leu Thr Ala Leu Arg Lys Ser Ser
                965                 970                 975

Pro Leu Phe Thr Leu Gly Asp Gly Ala Thr Val Met Lys Arg Val Asp
            980                 985                 990

Phe Arg Asn Thr Gly Ala Asp Gln Gln Thr Gly Leu Leu Val Met Thr
        995                 1000                1005

Ile Asp Asp Gly Met Gln Ala Gly Arg Gln Ser Gly Gln Pro Cys Arg
    1010                1015                1020

Arg His Arg Gly Gly Asp Gln Arg Ala Gly Lys Pro Asp Ala Ala
1025                1030                1035                1040

Gly Leu Arg Arg His Ile Ala Pro Ala Glu Arg Tyr Ser Ala Gly Gly
```

-continued

```
                  1045                1050                1055
Gly Arg Pro Val Ala Gly Glu Arg Val Gln Val Ala Ala Asp Gly Ser
            1060                1065                1070
Val Thr Leu Pro Ala Trp Ser Val Ala Val Leu Glu Leu Pro Gln Ala
        1075                1080                1085
Ser Arg Arg Ala Leu Ala Cys Arg
    1090                1095

<210> SEQ ID NO 7
<211> LENGTH: 776
<212> TYPE: PRT
<213> ORGANISM: Pseudomonas species SMP1
<220> FEATURE:
<221> NAME/KEY: PEPTIDE
<222> LOCATION: (1)..(776)
<223> OTHER INFORMATION: Isoamylase

<400> SEQUENCE: 7

Met Lys Cys Pro Lys Ile Leu Ala Ala Leu Leu Gly Cys Ala Val Leu
 1               5                  10                  15

Ala Gly Val Pro Ala Met Pro Ala His Ala Ala Ile Asn Ser Met Ser
            20                  25                  30

Leu Gly Ala Ser Tyr Asp Ala Gln Gln Ala Asn Ile Thr Phe Arg Val
        35                  40                  45

Tyr Ser Ser Gln Ala Thr Arg Ile Val Leu Tyr Leu Tyr Ser Ala Gly
    50                  55                  60

Tyr Gly Val Gln Glu Ser Ala Thr Tyr Thr Leu Ser Pro Ala Gly Ser
65                  70                  75                  80

Gly Val Trp Ala Val Thr Val Pro Val Ser Ser Ile Lys Ala Ala Gly
                85                  90                  95

Ile Thr Gly Ala Val Tyr Tyr Gly Tyr Arg Ala Trp Gly Pro Asn Trp
            100                 105                 110

Pro Tyr Ala Ser Asn Trp Gly Lys Gly Ser Gln Ala Gly Phe Val Ser
        115                 120                 125

Asp Val Asp Ala Asn Gly Asp Arg Phe Asn Pro Asn Lys Leu Leu Leu
    130                 135                 140

Asp Pro Tyr Ala Gln Glu Val Ser Gln Asp Pro Leu Asn Pro Ser Asn
145                 150                 155                 160

Gln Asn Gly Asn Val Phe Ala Ser Gly Ala Ser Tyr Arg Thr Thr Asp
                165                 170                 175

Ser Gly Ile Tyr Ala Pro Lys Gly Val Val Leu Val Pro Ser Thr Gln
            180                 185                 190

Ser Thr Gly Thr Lys Pro Thr Arg Ala Gln Lys Asp Asp Val Ile Tyr
        195                 200                 205

Glu Val His Val Arg Gly Phe Thr Glu Gln Asp Thr Ser Ile Pro Ala
    210                 215                 220

Gln Tyr Arg Gly Thr Tyr Tyr Gly Ala Gly Leu Lys Ala Ser Tyr Leu
225                 230                 235                 240

Ala Ser Leu Gly Val Thr Ala Val Glu Phe Leu Pro Val Gln Glu Thr
                245                 250                 255

Gln Asn Asp Ala Asn Asp Val Val Pro Asn Ser Asp Ala Asn Gln Asn
            260                 265                 270

Tyr Trp Gly Tyr Met Thr Glu Asn Tyr Phe Ser Pro Asp Arg Arg Tyr
        275                 280                 285

Ala Tyr Asn Lys Ala Ala Gly Gly Pro Thr Ala Glu Phe Gln Ala Met
    290                 295                 300
```

-continued

```
Val Gln Ala Phe His Asn Ala Gly Ile Lys Val Tyr Met Asp Val Val
305                 310                 315                 320

Tyr Asn His Thr Ala Glu Gly Gly Thr Trp Thr Ser Ser Asp Pro Thr
                325                 330                 335

Thr Ala Thr Ile Tyr Ser Trp Arg Gly Leu Asp Asn Thr Thr Tyr Tyr
            340                 345                 350

Glu Leu Thr Ser Gly Asn Gln Tyr Phe Tyr Asp Asn Thr Gly Ile Gly
        355                 360                 365

Ala Asn Phe Asn Thr Tyr Asn Thr Val Ala Gln Asn Leu Ile Val Asp
    370                 375                 380

Ser Leu Ala Tyr Trp Ala Asn Thr Met Gly Val Asp Gly Phe Arg Phe
385                 390                 395                 400

Asp Leu Ala Ser Val Leu Gly Asn Ser Cys Leu Asn Gly Ala Tyr Thr
                405                 410                 415

Ala Ser Ala Pro Asn Cys Pro Asn Gly Gly Tyr Asn Phe Asp Ala Ala
                420                 425                 430

Asp Ser Asn Val Ala Ile Asn Arg Ile Leu Arg Glu Phe Thr Val Arg
            435                 440                 445

Pro Ala Ala Gly Gly Ser Gly Leu Asp Leu Phe Ala Glu Pro Trp Ala
    450                 455                 460

Ile Gly Gly Asn Ser Tyr Gln Leu Gly Gly Phe Pro Gln Gly Trp Ser
465                 470                 475                 480

Glu Trp Asn Gly Leu Phe Arg Asp Ser Leu Arg Gln Ala Gln Asn Glu
                485                 490                 495

Leu Gly Ser Met Thr Ile Tyr Val Thr Gln Asp Ala Asn Asp Phe Ser
                500                 505                 510

Gly Ser Ser Asn Leu Phe Gln Ser Ser Gly Arg Ser Pro Trp Asn Ser
            515                 520                 525

Ile Asn Phe Ile Asp Val His Asp Gly Met Thr Leu Lys Asp Val Tyr
            530                 535                 540

Ser Cys Asn Gly Ala Asn Asn Ser Gln Ala Trp Pro Tyr Gly Pro Ser
545                 550                 555                 560

Asp Gly Gly Thr Ser Thr Asn Tyr Ser Trp Asp Gln Gly Met Ser Ala
                565                 570                 575

Gly Thr Gly Ala Ala Val Asp Gln Arg Arg Ala Ala Arg Thr Gly Met
                580                 585                 590

Ala Phe Glu Met Leu Ser Ala Gly Thr Pro Leu Met Gln Gly Gly Asp
        595                 600                 605

Glu Tyr Leu Arg Thr Leu Gln Cys Asn Asn Asn Ala Tyr Asn Leu Asp
    610                 615                 620

Ser Ser Ala Asn Trp Leu Thr Tyr Ser Trp Thr Thr Asp Gln Ser Asn
625                 630                 635                 640

Phe Tyr Thr Phe Ala Gln Arg Leu Ile Ala Phe Arg Lys Ala His Pro
                645                 650                 655

Ala Leu Arg Pro Ser Ser Trp Tyr Ser Gly Ser Gln Leu Thr Trp Tyr
            660                 665                 670

Gln Pro Ser Gly Ala Val Ala Asp Ser Asn Tyr Trp Asn Asn Thr Ser
        675                 680                 685

Asn Tyr Ala Ile Ala Tyr Ala Ile Asn Gly Pro Ser Leu Gly Asp Ser
    690                 695                 700

Asn Ser Ile Tyr Val Ala Tyr Asn Gly Trp Ser Ser Ser Val Thr Phe
705                 710                 715                 720
```

```
Thr Leu Pro Ala Pro Pro Ser Gly Thr Gln Trp Tyr Arg Val Thr Asp
            725                 730                 735

Thr Cys Asp Trp Asn Asp Gly Ala Ser Thr Phe Val Ala Pro Gly Ser
            740                 745                 750

Glu Thr Leu Ile Gly Gly Ala Gly Thr Thr Tyr Gly Gln Cys Gly Gln
            755                 760                 765

Ser Leu Leu Leu Leu Ile Ser Lys
    770                 775

<210> SEQ ID NO 8
<211> LENGTH: 774
<212> TYPE: PRT
<213> ORGANISM: Favobacterium odoratum
<220> FEATURE:
<221> NAME/KEY: PEPTIDE
<222> LOCATION: (1)..(774)
<223> OTHER INFORMATION: Isoamylase

<400> SEQUENCE: 8

Met Phe Asn Lys Tyr Lys Gln Ile Ser Glu Thr Asp Met Gln Arg Thr
  1               5                  10                  15

Ile Leu Ala Ala Leu Leu Thr Gly Ala Leu Leu Gly Ala Pro Ala Trp
             20                  25                  30

Ala Ala Ile Asn Pro Asn Lys Leu Gly Ala Ala Tyr Asp Ala Thr Lys
         35                  40                  45

Ala Asn Val Thr Phe Lys Val Tyr Ser Ser Lys Ala Thr Arg Ile Glu
     50                  55                  60

Leu Tyr Leu Tyr Ser Thr Ala Thr Gly Ser Ala Glu Lys Ala Lys Tyr
 65                  70                  75                  80

Val Met Thr Asn Ser Gly Gly Ile Trp Ser Val Thr Ile Pro Thr Ser
                 85                  90                  95

Thr Leu Ser Gly Gln Gly Leu Gly Gly Thr Leu Tyr Tyr Gly Tyr Arg
            100                 105                 110

Ala Trp Gly Pro Asn Trp Pro Tyr Asn Ala Ser Trp Thr Lys Gly Ser
        115                 120                 125

Ser Leu Gly Phe Ile Ser Asp Val Asp Ala Ala Gly Asn Arg Phe Asn
    130                 135                 140

Pro Asn Lys Leu Leu Ser Asp Pro Tyr Ala Leu Glu Leu Ser His Asp
145                 150                 155                 160

Pro Thr Thr Ala Thr Met Thr Asn Gly Ser Ile Tyr Ala Ser Gly Ala
                165                 170                 175

Thr Tyr Arg Asn Ile Asp Ser Gly Ser Ser Ala Pro Lys Gly Ile Val
            180                 185                 190

Leu Ala Gly Asp Thr Gln Ala Thr Gly Thr Lys Pro Thr Arg Ala Leu
        195                 200                 205

Lys Asp Asp Val Val Tyr Glu Ala His Val Arg Gly Leu Thr Met Asn
    210                 215                 220

Asp Thr Ser Ile Thr Ala Ala Tyr Arg Gly Thr Tyr Lys Gly Ala Gly
225                 230                 235                 240

Leu Lys Ala Ala Ala Leu Ala Ala Leu Gly Val Thr Ala Ile Glu Phe
                245                 250                 255

Leu Pro Val Gln Glu Thr Gln Asn Asp Thr Asn Asp Asn Asp Pro Ser
            260                 265                 270

Ser Thr Ser Gly Asp Asn Tyr Trp Gly Tyr Met Thr Leu Asn Tyr Phe
        275                 280                 285

Ala Pro Asp Arg Arg Tyr Ala Tyr Asp Lys Thr Pro Gly Gly Pro Thr
```

```
            290                 295                 300
Arg Glu Phe Lys Glu Met Val Lys Ala Phe His Asp Asn Gly Ile Lys
305                 310                 315                 320

Val Leu Val Asp Val Val Tyr Asn His Thr Gly Glu Gly Gly Ala Trp
                325                 330                 335

Ser Pro Thr Asp Lys Thr Thr Tyr Asn Ile Thr Ser Phe Arg Gly Leu
                340                 345                 350

Asp Asn Pro Thr Tyr Tyr Ser Leu Thr Ala Asp Phe Gln Asn Ser Trp
            355                 360                 365

Asp Asn Thr Gly Val Gly Gly Asn Tyr Asn Thr Arg Asn Thr Ile Ala
370                 375                 380

Gln Asn Leu Ile Val Asp Ser Leu Ala Tyr Trp Arg Asp Lys Leu Gly
385                 390                 395                 400

Val Asp Gly Tyr Arg Phe Asp Leu Ala Ser Val Leu Gly Asn Ser Cys
                405                 410                 415

Gln His Gly Cys Phe Asn Phe Asp Lys Met Asp Ala Gly Asn Ala Leu
                420                 425                 430

Asn Arg Ile Val Ala Glu Leu Pro Pro Arg Pro Ala Thr Gly Gly Ser
            435                 440                 445

Gly Val Asp Leu Ile Ala Glu Pro Trp Ala Ile Gly Gly Asn Ser Tyr
450                 455                 460

Gln Val Gly Gly Phe Pro Ser Gly Trp Ala Glu Trp Asn Gly Ala Tyr
465                 470                 475                 480

Arg Asp Val Val Arg Gln Ala Gln Asn Lys Leu Gly Ser Val Ala Ile
                485                 490                 495

Thr Thr Gly Gln Met Ala Thr Arg Phe Ala Gly Ser Ser Asp Leu Tyr
                500                 505                 510

Gly Asp Asp Gly Arg Lys Pro Trp His Ser Val Asn Phe Ile Thr Ala
            515                 520                 525

His Asp Gly Phe Thr Leu Lys Asp Leu Tyr Ser Cys Asn Ser Lys Asn
530                 535                 540

Asn Asn Gln Val Trp Pro Tyr Gly Pro Ser Asp Gly Gly Glu Asp Asn
545                 550                 555                 560

Asn Asn Ser Trp Asp Gln Gly Gly Ile Ala Ala Asp Gln Arg Lys Ala
                565                 570                 575

Ala Arg Asn Gly Met Ala Leu Met Met Leu Ser Ala Gly Val Pro Met
                580                 585                 590

Ile Val Gly Gly Asp Glu Ala Leu Arg Ser Met Asn Cys Asn Asn Asn
            595                 600                 605

Pro Tyr Asn Leu Asp Ser Ser Ala Asn Trp Leu Asn Trp Ser Arg Thr
610                 615                 620

Thr Asp Gln Asn Asn Phe Gln Ser Phe Ser Lys Ala Met Ile Ala Phe
625                 630                 635                 640

Arg Lys Ala His Pro Ala Leu Arg Pro Ala Asn Phe Tyr Ser Ser Val
                645                 650                 655

Asp Asn Asn Gly Asn Val Met Glu Gln Leu Arg Trp Phe Lys Pro Asp
            660                 665                 670

Gly Gly Val Ala Asp Ala Thr Tyr Phe Asn Asp Ala Asn Asn His Ala
            675                 680                 685

Ile Ala Trp Arg Ile Asp Gly Ser Glu Phe Gly Asp Thr Ala Ser Ala
            690                 695                 700

Ile Tyr Val Ala His Asn Ala Trp Ser Ala Gln Val Asn Phe Thr Leu
705                 710                 715                 720
```

Pro Trp Pro Gly Ala Gly Lys Ser Trp Tyr Arg Val Thr Asp Thr Cys
                725                 730                 735

Gly Trp Ala Glu Gly Ala Ser Gln Val Gln Ala Pro Gly Ser Glu Ala
            740                 745                 750

Leu Val Gly Gly Glu Asn Thr Ala Tyr Gly Leu Cys Gly Arg Gly Thr
        755                 760                 765

Leu Leu Leu Ile Ala Lys
    770

<210> SEQ ID NO 9
<211> LENGTH: 713
<212> TYPE: PRT
<213> ORGANISM: Sulfolobus acidocaldarius
<220> FEATURE:
<221> NAME/KEY: PEPTIDE
<222> LOCATION: (1)..(713)
<223> OTHER INFORMATION: Isoamylase

<400> SEQUENCE: 9

Met Lys Asp Arg Pro Leu Lys Pro Gly Glu Pro Tyr Pro Leu Gly Ala
  1               5                  10                  15

Thr Trp Ile Glu Glu Asp Gly Val Asn Phe Val Leu Phe Ser Glu
                 20                  25                  30

Asn Ala Thr Lys Val Glu Leu Leu Thr Tyr Ser Gln Thr Arg Gln Asp
             35                  40                  45

Glu Pro Lys Glu Ile Ile Glu Leu Arg Gln Arg Thr Gly Asp Leu Trp
         50                  55                  60

His Val Phe Val Pro Gly Leu Arg Pro Gly Gln Leu Tyr Gly Tyr Arg
 65                  70                  75                  80

Val Tyr Gly Pro Tyr Lys Pro Glu Glu Gly Leu Arg Phe Asn Pro Asn
                 85                  90                  95

Lys Val Leu Ile Asp Pro Tyr Ala Lys Ala Ile Asn Gly Leu Leu Leu
            100                 105                 110

Trp Asp Asp Ser Val Phe Gly Tyr Lys Ile Gly Asp Gln Asn Gln Asp
        115                 120                 125

Leu Ser Phe Asp Glu Arg Lys Asp Lys Phe Ile Pro Lys Gly Val
    130                 135                 140

Ile Ile Asn Pro Tyr Phe Asp Trp Glu Asp His Phe Phe Arg
145                 150                 155                 160

Arg Lys Ile Pro Phe Lys Asp Ser Ile Ile Tyr Glu Thr His Ile Lys
                165                 170                 175

Gly Ile Thr Lys Leu Arg Gln Asp Leu Pro Glu Asn Val Arg Gly Thr
            180                 185                 190

Phe Leu Gly Leu Ala Ser Asp Thr Met Ile Asp Tyr Leu Lys Asp Leu
        195                 200                 205

Gly Ile Thr Thr Val Glu Ile Met Pro Ile Gln Gln Phe Val Asp Glu
    210                 215                 220

Arg Phe Ile Val Asp Lys Gly Leu Lys Asn Tyr Trp Gly Tyr Asn Pro
225                 230                 235                 240

Ile Asn Tyr Phe Ser Pro Glu Cys Arg Tyr Ser Ser Gly Cys Leu
                245                 250                 255

Gly Asn Gln Val Ile Glu Phe Lys Lys Leu Val Asn Ser Leu His Asn
            260                 265                 270

Ala Gly Leu Glu Val Ile Ile Asp Val Val Tyr Asn His Thr Ala Glu
        275                 280                 285

```
Gly Asn His Leu Gly Pro Thr Leu Ser Phe Lys Gly Ile Asp Asn Ser
290                 295                 300

Ser Tyr Tyr Met Leu Asp Pro Lys Asn Lys Arg Tyr Tyr Ile Asp Phe
305                 310                 315                 320

Thr Gly Thr Gly Asn Thr Leu Asn Leu Ser His Pro Arg Val Leu Gln
            325                 330                 335

Leu Val Leu Asp Ser Leu Arg Tyr Trp Val Leu Glu Met His Val Asp
            340                 345                 350

Gly Phe Arg Phe Asp Leu Ala Ser Ala Leu Ala Arg Gln Leu Tyr Ser
            355                 360                 365

Val Asn Met Leu Ser Thr Phe Phe Val Ala Ile Gln Gln Asp Pro Ile
            370                 375                 380

Leu Ser Gln Val Lys Leu Ile Ala Glu Pro Trp Asp Val Gly Pro Gly
385                 390                 395                 400

Gly Tyr Gln Val Gly Asn Phe Pro Tyr Leu Trp Ala Glu Trp Asn Gly
            405                 410                 415

Lys Tyr Arg Asp Thr Ile Arg Arg Phe Trp Arg Gly Asp Pro Val Pro
            420                 425                 430

Tyr Glu Glu Leu Ala Asn Arg Leu Leu Gly Ser Pro Asp Leu Tyr Ala
            435                 440                 445

Gly Ser Asn Lys Thr Pro Phe Ala Ser Ile Asn Tyr Ile Thr Ser His
450                 455                 460

Asp Gly Phe Thr Leu Gln Asp Leu Val Ser Tyr Asn Gln Lys His Asn
465                 470                 475                 480

Glu Ala Asn Lys Leu Asn Asn Glu Asp Gly Met Asn Glu Asn Tyr Ser
            485                 490                 495

Trp Asn Cys Gly Val Glu Gly Leu Thr Asn Asp Ser Asn Ile Leu Tyr
            500                 505                 510

Cys Arg Glu Lys Gln Arg Asn Phe Val Ile Thr Leu Phe Val Ser
            515                 520                 525

Gln Gly Ile Pro Met Ile Leu Gly Gly Asp Glu Ile Gly Arg Thr Gln
530                 535                 540

Lys Gly Asn Asn Asn Ala Phe Cys Gln Asp Asn Glu Thr Ser Trp Tyr
545                 550                 555                 560

Asp Trp Asn Leu Asp Glu Asn Arg Val Arg Phe His Asp Phe Val Arg
            565                 570                 575

Arg Leu Thr Asn Phe Tyr Lys Ala His Pro Ile Phe Arg Arg Ala Arg
            580                 585                 590

Tyr Phe Gln Gly Lys Lys Leu His Gly Ser Pro Leu Lys Asp Val Thr
            595                 600                 605

Trp Leu Lys Pro Asp Gly Asn Glu Val Asp Ser Val Trp Lys Ser
610                 615                 620

Pro Thr Asn His Ile Ile Tyr Ile Leu Glu Gly Ser Ala Ile Asp Glu
625                 630                 635                 640

Ile Asn Tyr Asn Gly Glu Arg Ile Ala Asp Asp Thr Phe Leu Ile Ile
            645                 650                 655

Leu Asn Gly Ala Ser Thr Asn Leu Lys Ile Lys Val Pro His Gly Lys
            660                 665                 670

Trp Glu Leu Val Leu His Pro Tyr Pro His Glu Pro Ser Asn Asp Lys
            675                 680                 685

Lys Ile Ile Glu Asn Asn Lys Glu Val Glu Ile Asp Gly Lys Thr Ala
            690                 695                 700

Leu Ile Tyr Arg Arg Ile Glu Phe Gln
```

-continued

```
705              710
```

<210> SEQ ID NO 10
<211> LENGTH: 718
<212> TYPE: PRT
<213> ORGANISM: Sulfolobus sulfataricus
<220> FEATURE:
<221> NAME/KEY: PEPTIDE
<222> LOCATION: (1)..(718)
<223> OTHER INFORMATION: Isoamylase

<400> SEQUENCE: 10

```
Met Ala Leu Phe Phe Arg Thr Arg Asp Arg Pro Leu Arg Pro Gly Asp
  1               5                  10                  15

Pro Tyr Pro Leu Gly Ser Asn Trp Ile Glu Asp Asp Gly Val Asn
             20                  25                  30

Phe Ser Leu Phe Ser Glu Asn Ala Glu Lys Val Glu Leu Leu Leu Tyr
         35                  40                  45

Ser Leu Thr Asn Gln Lys Tyr Pro Lys Glu Ile Ile Glu Val Lys Asn
     50                  55                  60

Lys Thr Gly Asp Ile Trp His Val Phe Val Pro Gly Leu Arg Pro Gly
 65                  70                  75                  80

Gln Leu Tyr Ala Tyr Arg Val Tyr Gly Pro Tyr Lys Pro Glu Leu Gly
                 85                  90                  95

Leu Arg Phe Asn Pro Asn Lys Val Leu Ile Asp Pro Tyr Ala Lys Ala
            100                 105                 110

Ile Asn Gly Ser Val Ile Trp Asn Asp Ala Val Phe Gly Tyr Lys Ile
        115                 120                 125

Gly Asp Gln Asn Gln Asp Leu Thr Tyr Asp Glu Arg Asp Ser Gly Glu
    130                 135                 140

Tyr Val Pro Lys Ser Val Val Ile Asn Pro Tyr Phe Glu Trp Asp Asp
145                 150                 155                 160

Glu Asp Phe Ile Lys Gly Lys Lys Val Pro Leu Lys Asp Thr Val Ile
                165                 170                 175

Tyr Glu Val His Val Lys Gly Phe Thr Lys Leu Arg Leu Asp Leu Pro
            180                 185                 190

Glu Asn Ile Arg Gly Thr Tyr Glu Gly Leu Ala Ser Glu Gln Met Ile
        195                 200                 205

Ser Tyr Leu Lys Asp Leu Gly Ile Thr Thr Val Glu Leu Met Pro Val
    210                 215                 220

Phe His Phe Ile Asp Gln Arg Phe Leu Thr Asp Lys Gly Leu Thr Asn
225                 230                 235                 240

Tyr Trp Gly Tyr Asp Pro Ile Asn Phe Phe Ser Pro Glu Cys Arg Tyr
                245                 250                 255

Ser Ser Thr Gly Cys Leu Gly Gly Gln Val Leu Ser Phe Lys Lys Met
            260                 265                 270

Val Asn Glu Leu His Asn Ala Gly Ile Glu Val Ile Ile Asp Val Val
        275                 280                 285

Tyr Asn His Thr Ala Glu Gly Asn His Leu Gly Pro Thr Leu Ser Phe
    290                 295                 300

Arg Gly Ile Asp Asn Thr Ala Tyr Tyr Met Leu Gln Pro Asp Asn Lys
305                 310                 315                 320

Arg Tyr Tyr Leu Asp Phe Thr Gly Thr Gly Asn Thr Leu Asn Leu Ser
                325                 330                 335

His Pro Arg Val Ile Gln Met Val Leu Asp Ser Leu Arg Tyr Trp Val
            340                 345                 350
```

```
Thr Glu Met His Val Asp Gly Phe Arg Phe Asp Leu Ala Ala Ala Leu
        355                 360                 365

Ala Arg Glu Leu Tyr Ser Val Asn Met Leu Asn Thr Phe Phe Ile Ala
        370                 375                 380

Leu Gln Gln Asp Pro Ile Leu Ser Gln Val Lys Leu Ile Ala Glu Pro
385                 390                 395                 400

Trp Asp Val Gly Gln Gly Gly Tyr Gln Val Gly Asn Phe Pro Tyr Gln
                405                 410                 415

Trp Ala Glu Trp Asn Gly Lys Tyr Arg Asp Ser Ile Arg Arg Phe Trp
                420                 425                 430

Arg Gly Glu Ala Leu Pro Tyr Ser Glu Ile Ala Asn Arg Leu Leu Gly
        435                 440                 445

Ser Pro Asp Ile Tyr Leu Gly Asn Asn Lys Thr Pro Phe Ala Ser Ile
        450                 455                 460

Asn Tyr Val Thr Ser His Asp Gly Phe Thr Leu Glu Asp Leu Val Ser
465                 470                 475                 480

Tyr Asn Gln Lys His Asn Glu Ala Asn Gly Phe Asn Asn Gln Asp Gly
                485                 490                 495

Met Asn Glu Asn Tyr Ser Trp Asn Cys Gly Ala Glu Gly Pro Thr Asn
                500                 505                 510

Asp Gln Asn Val Val Ile Cys Arg Glu Lys Gln Lys Arg Asn Phe Met
        515                 520                 525

Ile Thr Leu Leu Val Ser Gln Gly Thr Pro Met Ile Leu Gly Gly Asp
        530                 535                 540

Glu Leu Ser Arg Thr Gln Arg Gly Asn Asn Asn Ala Phe Cys Gln Asp
545                 550                 555                 560

Asn Glu Ile Thr Trp Phe Asp Trp Asn Leu Asp Glu Arg Lys Ser Lys
                565                 570                 575

Phe Leu Glu Phe Val Lys Lys Met Ile Gln Phe Tyr Arg Ala His Pro
                580                 585                 590

Ala Phe Arg Arg Glu Arg Tyr Phe Gln Gly Lys Lys Leu Phe Gly Met
        595                 600                 605

Pro Leu Lys Asp Val Thr Phe Tyr Thr Leu Glu Gly Arg Glu Val Asp
610                 615                 620

Glu Lys Thr Trp Ser Ser Pro Thr Gln Leu Val Ile Phe Val Leu Glu
625                 630                 635                 640

Gly Ser Val Met Asp Glu Ile Asn Met Tyr Gly Glu Arg Ile Ala Asp
                645                 650                 655

Asp Ser Phe Leu Ile Ile Leu Asn Ala Asn Pro Asn Asn Val Lys Val
                660                 665                 670

Lys Phe Pro Lys Gly Lys Trp Glu Leu Val Ile Ser Ser Tyr Leu Arg
        675                 680                 685

Glu Ile Lys Pro Glu Glu Arg Ile Ile Glu Gly Glu Lys Glu Leu Glu
        690                 695                 700

Ile Glu Gly Arg Thr Ala Leu Val Tyr Arg Arg Ile Glu Leu
705                 710                 715

<210> SEQ ID NO 11
<211> LENGTH: 818
<212> TYPE: PRT
<213> ORGANISM: Zea mays
<220> FEATURE:
<221> NAME/KEY: PEPTIDE
<222> LOCATION: (1)..(818)
<223> OTHER INFORMATION: Isoamylase
```

<400> SEQUENCE: 11

```
Arg Leu Val Thr His Ser Thr Arg Thr His Tyr Leu Ile Gly Gln Ser
 1               5                   10                  15
Gln Thr Asn Trp Ala Pro Ser Pro Pro Leu Pro Leu Pro Met Ala Gln
            20                  25                  30
Lys Leu Pro Cys Val Ser Ser Pro Arg Pro Leu Leu Ala Val Pro Ala
        35                  40                  45
Gly Arg Trp Arg Ala Gly Val Arg Gly Arg Pro Asn Val Ala Gly Leu
    50                  55                  60
Gly Arg Gly Arg Leu Ser Leu His Ala Ala Ala Arg Pro Val Ala
 65                 70                  75                  80
Glu Ala Val Gln Ala Glu Glu Asp Asp Asp Asp Asp Glu Val
                85                  90                  95
Ala Glu Glu Arg Phe Ala Leu Gly Gly Ala Cys Arg Val Leu Ala Gly
            100                 105                 110
Met Pro Ala Pro Leu Gly Ala Thr Ala Leu Arg Gly Gly Val Asn Phe
        115                 120                 125
Ala Val Tyr Ser Ser Gly Ala Ser Ala Ser Leu Ser Leu Phe Ala
    130                 135                 140
Pro Gly Asp Leu Lys Ala Asp Arg Val Thr Glu Val Pro Leu Asp
145                 150                 155                 160
Pro Leu Leu Asn Arg Thr Gly Asn Val Trp His Val Phe Ile His Gly
                165                 170                 175
Asp Glu Leu His Gly Met Leu Cys Gly Tyr Arg Phe Asp Gly Val Phe
            180                 185                 190
Ala Pro Glu Arg Gly Gln Tyr Tyr Asp Val Ser Asn Val Val Val Asp
        195                 200                 205
Pro Tyr Ala Lys Ala Val Val Ser Arg Gly Glu Tyr Gly Val Pro Ala
    210                 215                 220
Pro Gly Gly Ser Cys Trp Pro Gln Met Ala Gly Met Ile Pro Leu Pro
225                 230                 235                 240
Tyr Asn Lys Phe Asp Trp Gln Gly Asp Leu Pro Leu Gly Tyr His Gln
                245                 250                 255
Lys Asp Leu Val Ile Tyr Glu Met His Leu Arg Gly Phe Thr Lys His
            260                 265                 270
Asn Ser Ser Lys Thr Lys His Pro Gly Thr Tyr Ile Gly Ala Val Ser
        275                 280                 285
Lys Leu Asp His Leu Lys Glu Leu Gly Val Asn Cys Ile Glu Leu Met
    290                 295                 300
Pro Cys His Glu Phe Asn Glu Leu Glu Tyr Phe Ser Ser Ser Lys
305                 310                 315                 320
Met Asn Phe Trp Gly Tyr Ser Thr Ile Asn Phe Phe Ser Pro Met Ala
                325                 330                 335
Arg Tyr Ser Ser Ser Gly Ile Arg Asp Ser Gly Cys Gly Ala Ile Asn
            340                 345                 350
Glu Phe Lys Ala Phe Val Arg Glu Ala His Lys Arg Gly Ile Glu Val
        355                 360                 365
Ile Met Asp Val Val Phe Asn His Thr Ala Glu Gly Asn Glu Lys Gly
    370                 375                 380
Pro Ile Leu Ser Phe Arg Gly Ile Asp Asn Ser Thr Tyr Tyr Met Leu
385                 390                 395                 400
Ala Pro Lys Gly Glu Phe Tyr Asn Tyr Ser Gly Cys Gly Asn Thr Phe
```

```
                405                 410                 415
Asn Cys Asn His Pro Val Val Arg Glu Phe Ile Val Asp Cys Leu Arg
            420                 425                 430

Tyr Trp Val Thr Glu Met His Val Asp Gly Phe Arg Phe Asp Leu Ala
            435                 440                 445

Ser Ile Leu Thr Arg Gly Cys Ser Leu Trp Asp Pro Val Asn Val Tyr
450                 455                 460

Gly Ser Pro Met Glu Gly Asp Met Ile Thr Thr Gly Thr Pro Leu Val
465                 470                 475                 480

Ala Pro Pro Leu Ile Asp Met Ile Ser Asn Asp Pro Ile Leu Gly Asn
            485                 490                 495

Val Lys Leu Ile Ala Glu Ala Trp Asp Ala Gly Gly Leu Tyr Gln Glu
            500                 505                 510

Gly Gln Phe Pro His Trp Asn Val Trp Ser Glu Trp Asn Gly Lys Tyr
            515                 520                 525

Arg Asp Thr Val Arg Gln Phe Ile Lys Gly Thr Asp Gly Phe Ala Gly
            530                 535                 540

Ala Phe Ala Glu Cys Leu Cys Gly Ser Pro Gln Leu Tyr Gln Ala Gly
545                 550                 555                 560

Gly Arg Lys Pro Trp His Ser Ile Gly Phe Val Cys Ala His Asp Gly
            565                 570                 575

Phe Thr Leu Ala Asp Leu Val Thr Tyr Asn Ser Lys Tyr Asn Leu Ser
            580                 585                 590

Asn Gly Glu Asp Phe Arg Asp Gly Glu Asn His Asn Leu Ser Trp Asn
            595                 600                 605

Cys Gly Glu Glu Gly Glu Phe Ala Ser Leu Ser Val Arg Arg Leu Arg
            610                 615                 620

Lys Arg Gln Met Arg Asn Phe Phe Val Cys Leu Met Val Ser Gln Gly
625                 630                 635                 640

Val Pro Met Phe Tyr Met Gly Asp Glu Tyr Gly His Thr Lys Gly Gly
            645                 650                 655

Asn Asn Asn Thr Tyr Cys His Asp His Tyr Val Asn Tyr Phe Arg Trp
            660                 665                 670

Asp Lys Lys Glu Glu Gln Ser Ser Asp Leu Tyr Arg Phe Cys Arg Leu
            675                 680                 685

Met Thr Glu Phe Arg Lys Glu Cys Glu Ser Leu Gly Leu Glu Asp Phe
            690                 695                 700

Pro Thr Ser Glu Arg Leu Lys Trp His Gly His Gln Pro Gly Lys Pro
705                 710                 715                 720

Asp Trp Ser Glu Ala Ser Arg Phe Val Ala Phe Thr Met Lys Asp Glu
            725                 730                 735

Thr Lys Gly Glu Ile Tyr Val Ala Phe Asn Thr Ser His Leu Pro Val
            740                 745                 750

Val Val Gly Leu Pro Glu Arg Ser Gly Phe Arg Trp Glu Pro Val Val
            755                 760                 765

Asp Thr Gly Lys Glu Ala Pro Tyr Asp Phe Leu Thr Asp Gly Leu Pro
770                 775                 780

Asp Arg Ala Val Thr Val Tyr Gln Phe Ser His Phe Leu Asn Ser Asn
785                 790                 795                 800

Leu Tyr Pro Met Leu Ser Tyr Ser Ser Ile Ile Leu Val Leu Arg Pro
            805                 810                 815
Asp Val
```

<210> SEQ ID NO 12
<211> LENGTH: 2181
<212> TYPE: DNA
<213> ORGANISM: Rhodotermus marinus DSM 4252
<220> FEATURE:
<221> NAME/KEY: CDS
<222> LOCATION: (1)..(2181)
<223> OTHER INFORMATION: Isoamylase

<400> SEQUENCE: 12

```
atg tca cat agc gcg caa ccg gtt acg tcg gta cag gcc gtc tgg ccc      48
Met Ser His Ser Ala Gln Pro Val Thr Ser Val Gln Ala Val Trp Pro
 1               5                  10                  15 ggc cgg cct tat ccg ctg ggt gcc acc tgg gac ggg ctg ggc gtc aac      96
Gly Arg Pro Tyr Pro Leu Gly Ala Thr Trp Asp Gly Leu Gly Val Asn
            20                  25                  30 ttt gcc ctc tac agc cag cac gcc gag gcg gtc gaa ctg gtg ctg ttc     144
Phe Ala Leu Tyr Ser Gln His Ala Glu Ala Val Glu Leu Val Leu Phe
        35                  40                  45 gac cac ccg gac gat ccc gcg cct tcg cgc acg atc gaa gtg acc gaa     192
Asp His Pro Asp Asp Pro Ala Pro Ser Arg Thr Ile Glu Val Thr Glu
    50                  55                  60 cgg aca ggc ccg atc tgg cat gtg tac ctg ccc ggc ctg cgt ccc ggc     240
Arg Thr Gly Pro Ile Trp His Val Tyr Leu Pro Gly Leu Arg Pro Gly
65                  70                  75                  80 cag ctc tac ggc tat cgc gtc tac gga ccc tac cgg ccg gag gaa ggc     288
Gln Leu Tyr Gly Tyr Arg Val Tyr Gly Pro Tyr Arg Pro Glu Glu Gly
                85                  90                  95 cac cgc ttc aat ccg aac aag gtg ctg ctc gac ccc tac gcg aag gcc     336
His Arg Phe Asn Pro Asn Lys Val Leu Leu Asp Pro Tyr Ala Lys Ala
            100                 105                 110 atc ggc cgg ccc ctt cgc tgg cac gac agc ctc ttc ggt tac aaa atc     384
Ile Gly Arg Pro Leu Arg Trp His Asp Ser Leu Phe Gly Tyr Lys Ile
        115                 120                 125 ggc gat ccg gcc ggg gat ctg tcg ttc tcc gaa gaa gac agc gct ccg     432
Gly Asp Pro Ala Gly Asp Leu Ser Phe Ser Glu Glu Asp Ser Ala Pro
    130                 135                 140 tac gcg ccg ctg gga gcc gtc gtg gag ggc tgt ttc gag tgg ggc gac     480
Tyr Ala Pro Leu Gly Ala Val Val Glu Gly Cys Phe Glu Trp Gly Asp
145                 150                 155                 160 gac cgc ccg ccg cgc att ccc tgg gaa gac acg atc atc tac gaa acg     528
Asp Arg Pro Pro Arg Ile Pro Trp Glu Asp Thr Ile Ile Tyr Glu Thr
                165                 170                 175 cac gtc aag ggc atc acg aag ctg cat ccg gaa gtg ccg gag ccg ctg     576
His Val Lys Gly Ile Thr Lys Leu His Pro Glu Val Pro Glu Pro Leu
            180                 185                 190 cgg ggg acg tat ctg ggg ctg acc tgc gag ccg gtg ctg gag cac ctg     624
Arg Gly Thr Tyr Leu Gly Leu Thr Cys Glu Pro Val Leu Glu His Leu
        195                 200                 205 aag cag ctg ggc gtc acc acg atc cag ctc ctt ccg gtg cac gca aaa     672
Lys Gln Leu Gly Val Thr Thr Ile Gln Leu Leu Pro Val His Ala Lys
    210                 215                 220 gtg cac gat cgg cac ctg gtc gag cgc ggc ctg cgc aac tac tgg ggc     720
Val His Asp Arg His Leu Val Glu Arg Gly Leu Arg Asn Tyr Trp Gly
225                 230                 235                 240 tac aat ccg ctc tgc tac ttt gcg ccg gag ccc gag tac gcc acg aac     768
Tyr Asn Pro Leu Cys Tyr Phe Ala Pro Glu Pro Glu Tyr Ala Thr Asn
                245                 250                 255 ggg ccg atc tcg gcc gtg cgc gag ttc aag atg atg gtg cgg gcg ctg     816
Gly Pro Ile Ser Ala Val Arg Glu Phe Lys Met Met Val Arg Ala Leu
            260                 265                 270
```

```
cat gct gcc ggc ttc gag gtg atc gtc gac gtg gtc tac aac cac acg        864
His Ala Ala Gly Phe Glu Val Ile Val Asp Val Val Tyr Asn His Thr
        275                 280                 285 ggc gaa ggc ggc gtg ctg ggc ccc acg ctg tcg ttc cgg ggc atc gac        912
Gly Glu Gly Gly Val Leu Gly Pro Thr Leu Ser Phe Arg Gly Ile Asp
290                 295                 300 aac cgc gcc tac tac aag gcc gat ccg aac aac ccg cgc ttt ctg gtc        960
Asn Arg Ala Tyr Tyr Lys Ala Asp Pro Asn Asn Pro Arg Phe Leu Val
305                 310                 315                 320 gat tac acg ggc acc ggc aac acg ctg gac gtg ggc aac ccc tac gtc       1008
Asp Tyr Thr Gly Thr Gly Asn Thr Leu Asp Val Gly Asn Pro Tyr Val
                325                 330                 335 atc cag ctc atc atg gac agc ctg cgc tac tgg gtc act gaa atg cac       1056
Ile Gln Leu Ile Met Asp Ser Leu Arg Tyr Trp Val Thr Glu Met His
            340                 345                 350 gtc gac ggc ttt cgg ttc gac ctg gcc gcg ctg gcc cgc gag ctg           1104
Val Asp Gly Phe Arg Phe Asp Leu Ala Ala Ala Leu Ala Arg Glu Leu
                355                 360                 365 tac gac gtg gac atg ctc tcg acc ttt ttt cag gtc att cag cag gac       1152
Tyr Asp Val Asp Met Leu Ser Thr Phe Phe Gln Val Ile Gln Gln Asp
370                 375                 380 ccg gtg ctc agc cag gtc aag ctc atc gcc gaa ccc tgg gac gtc ggg       1200
Pro Val Leu Ser Gln Val Lys Leu Ile Ala Glu Pro Trp Asp Val Gly
385                 390                 395                 400 ccg ggg ggg tat cag gtg gga cat ttt ccc tgg cag tgg acc gag tgg       1248
Pro Gly Gly Tyr Gln Val Gly His Phe Pro Trp Gln Trp Thr Glu Trp
                405                 410                 415 aac ggc cgc tat cgt gac gcc gtg cgc cgc ttc tgg cgg ggc gat cgg       1296
Asn Gly Arg Tyr Arg Asp Ala Val Arg Arg Phe Trp Arg Gly Asp Arg
            420                 425                 430 ggc ctc aac ggt gag ttt gcc acg cgc ttt gcc ggc tcc agc gat ctg       1344
Gly Leu Asn Gly Glu Phe Ala Thr Arg Phe Ala Gly Ser Ser Asp Leu
                435                 440                 445 tac gaa cgt agc ggt cgt cgt ccg ttc gct tcg atc aac ttc gtc acg       1392
Tyr Glu Arg Ser Gly Arg Arg Pro Phe Ala Ser Ile Asn Phe Val Thr
450                 455                 460 gcg cac gac ggc ttc acg ctg gaa gac ctg gtc agc tac acg aaa aag       1440
Ala His Asp Gly Phe Thr Leu Glu Asp Leu Val Ser Tyr Thr Lys Lys
465                 470                 475                 480 cac aac gaa gcg aat ctg gaa ggc aac cgg gac ggc atg gac gaa aac       1488
His Asn Glu Ala Asn Leu Glu Gly Asn Arg Asp Gly Met Asp Glu Asn
                485                 490                 495 tac agc acg aac tgc ggg gtg gag gga ccc acg cag gat ccg tcc gtg       1536
Tyr Ser Thr Asn Cys Gly Val Glu Gly Pro Thr Gln Asp Pro Ser Val
            500                 505                 510 ctg gcc tgc cgg gaa gcg ctc aag cgc agc ctg atc agc acg ctc ttt       1584
Leu Ala Cys Arg Glu Ala Leu Lys Arg Ser Leu Ile Ser Thr Leu Phe
                515                 520                 525 ctc tcg cag ggc gtg ccc atg ctg ctg ggc ggc gac gag ctg tcg cgc       1632
Leu Ser Gln Gly Val Pro Met Leu Leu Gly Gly Asp Glu Leu Ser Arg
530                 535                 540 acg cag cac ggc aac aac aac gcc tat tgc cag gac aac gag atc agc       1680
Thr Gln His Gly Asn Asn Asn Ala Tyr Cys Gln Asp Asn Glu Ile Ser
545                 550                 555                 560 tgg tac aac tgg cag ctc gac acg cgc aag cag cag ttt ctg gag ttc       1728
Trp Tyr Asn Trp Gln Leu Asp Thr Arg Lys Gln Gln Phe Leu Glu Phe
                565                 570                 575 gtg cgc cag acg atc tgg ttt cgc aag cag cat cgg agc ttc cgg cgc       1776
Val Arg Gln Thr Ile Trp Phe Arg Lys Gln His Arg Ser Phe Arg Arg
            580                 585                 590
```

-continued

```
cgc cat ttt ctg acc gga ttg ccc aac ggc gga agg ccc cga cgc agt    1824
Arg His Phe Leu Thr Gly Leu Pro Asn Gly Gly Arg Pro Arg Arg Ser
    595                 600                 605 ctg gtg gca cct gag ggt cgg ccc atg cgc cac gag gac tgg acc aac    1872
Leu Val Ala Pro Glu Gly Arg Pro Met Arg His Glu Asp Trp Thr Asn
610                 615                 620 ccg gag ctg acg gcc ttc gga ctg ctg ctg cac ggc gac gcc att cag    1920
Pro Glu Leu Thr Ala Phe Gly Leu Leu Leu His Gly Asp Ala Ile Gln
625                 630                 635                 640 ggg acc gac gag cac gga cga ccg ttt cgc gac gac acg ttt ctg att    1968
Gly Thr Asp Glu His Gly Arg Pro Phe Arg Asp Asp Thr Phe Leu Ile
            645                 650                 655 ctg ttc aac aac ggc agc gaa gcc gtg ccg gtc gtg gtg ccg gag gta    2016
Leu Phe Asn Asn Gly Ser Glu Ala Val Pro Val Val Val Pro Glu Val
        660                 665                 670 tgc tcc tgt ggc aag ccg cac cac tgg gag gtg gtc ccg gtg ttt caa    2064
Cys Ser Cys Gly Lys Pro His His Trp Glu Val Val Pro Val Phe Gln
    675                 680                 685 cgc aat gtg gag ccc ccc acg tgc gcg ccc ggc gag acg ctg tcg ctc    2112
Arg Asn Val Glu Pro Pro Thr Cys Ala Pro Gly Glu Thr Leu Ser Leu
690                 695                 700 ccg ccc ggc gtg ctg acg gtg ctg gtg gcc gta ccg ccg ttc tcg gat    2160
Pro Pro Gly Val Leu Thr Val Leu Val Ala Val Pro Pro Phe Ser Asp
705                 710                 715                 720 gga aac acg gag ccg gcc tga                                        2181
Gly Asn Thr Glu Pro Ala
            725

<210> SEQ ID NO 13
<211> LENGTH: 726
<212> TYPE: PRT
<213> ORGANISM: Rhodotermus marinus DSM 4252

<400> SEQUENCE: 13

Met Ser His Ser Ala Gln Pro Val Thr Ser Val Gln Ala Val Trp Pro
 1               5                  10                  15

Gly Arg Pro Tyr Pro Leu Gly Ala Thr Trp Asp Gly Leu Gly Val Asn
                20                  25                  30

Phe Ala Leu Tyr Ser Gln His Ala Glu Ala Val Glu Leu Val Leu Phe
            35                  40                  45

Asp His Pro Asp Asp Pro Ala Pro Ser Arg Thr Ile Glu Val Thr Glu
        50                  55                  60

Arg Thr Gly Pro Ile Trp His Val Tyr Leu Pro Gly Leu Arg Pro Gly
 65                 70                  75                  80

Gln Leu Tyr Gly Tyr Arg Val Tyr Gly Pro Tyr Arg Pro Glu Glu Gly
                85                  90                  95

His Arg Phe Asn Pro Asn Lys Val Leu Leu Asp Pro Tyr Ala Lys Ala
            100                 105                 110

Ile Gly Arg Pro Leu Arg Trp His Asp Ser Leu Phe Gly Tyr Lys Ile
        115                 120                 125

Gly Asp Pro Ala Gly Asp Leu Ser Phe Ser Glu Asp Ser Ala Pro
    130                 135                 140

Tyr Ala Pro Leu Gly Ala Val Val Glu Gly Cys Phe Glu Trp Gly Asp
145                 150                 155                 160

Asp Arg Pro Pro Arg Ile Pro Trp Glu Asp Thr Ile Ile Tyr Glu Thr
                165                 170                 175

His Val Lys Gly Ile Thr Lys Leu His Pro Glu Val Pro Glu Pro Leu
```

-continued

```
                180                 185                 190
Arg Gly Thr Tyr Leu Gly Leu Thr Cys Glu Pro Val Leu Glu His Leu
                195                 200                 205
Lys Gln Leu Gly Val Thr Thr Ile Gln Leu Leu Pro Val His Ala Lys
                210                 215                 220
Val His Asp Arg His Leu Val Glu Arg Gly Leu Arg Asn Tyr Trp Gly
225                 230                 235                 240
Tyr Asn Pro Leu Cys Tyr Phe Ala Pro Glu Pro Glu Tyr Ala Thr Asn
                245                 250                 255
Gly Pro Ile Ser Ala Val Arg Glu Phe Lys Met Met Val Arg Ala Leu
                260                 265                 270
His Ala Ala Gly Phe Glu Val Ile Val Asp Val Val Tyr Asn His Thr
                275                 280                 285
Gly Glu Gly Gly Val Leu Gly Pro Thr Leu Ser Phe Arg Gly Ile Asp
                290                 295                 300
Asn Arg Ala Tyr Tyr Lys Ala Asp Pro Asn Asn Pro Arg Phe Leu Val
305                 310                 315                 320
Asp Tyr Thr Gly Thr Gly Asn Thr Leu Asp Val Gly Asn Pro Tyr Val
                325                 330                 335
Ile Gln Leu Ile Met Asp Ser Leu Arg Tyr Trp Val Thr Glu Met His
                340                 345                 350
Val Asp Gly Phe Arg Phe Asp Leu Ala Ala Ala Leu Ala Arg Glu Leu
                355                 360                 365
Tyr Asp Val Asp Met Leu Ser Thr Phe Gln Val Ile Gln Gln Asp
                370                 375                 380
Pro Val Leu Ser Gln Val Lys Leu Ile Ala Glu Pro Trp Asp Val Gly
385                 390                 395                 400
Pro Gly Gly Tyr Gln Val Gly His Phe Pro Trp Gln Trp Thr Glu Trp
                405                 410                 415
Asn Gly Arg Tyr Arg Asp Ala Val Arg Arg Phe Trp Arg Gly Asp Arg
                420                 425                 430
Gly Leu Asn Gly Glu Phe Ala Thr Arg Phe Ala Gly Ser Ser Asp Leu
                435                 440                 445
Tyr Glu Arg Ser Gly Arg Arg Pro Phe Ala Ser Ile Asn Phe Val Thr
                450                 455                 460
Ala His Asp Gly Phe Thr Leu Glu Asp Leu Val Ser Tyr Thr Lys Lys
465                 470                 475                 480
His Asn Glu Ala Asn Leu Glu Gly Asn Arg Asp Gly Met Asp Glu Asn
                485                 490                 495
Tyr Ser Thr Asn Cys Gly Val Glu Gly Pro Thr Gln Asp Pro Ser Val
                500                 505                 510
Leu Ala Cys Arg Glu Ala Leu Lys Arg Ser Leu Ile Ser Thr Leu Phe
                515                 520                 525
Leu Ser Gln Gly Val Pro Met Leu Leu Gly Gly Asp Glu Leu Ser Arg
                530                 535                 540
Thr Gln His Gly Asn Asn Asn Ala Tyr Cys Gln Asp Asn Glu Ile Ser
545                 550                 555                 560
Trp Tyr Asn Trp Gln Leu Asp Thr Arg Lys Gln Gln Phe Leu Glu Phe
                565                 570                 575
Val Arg Gln Thr Ile Trp Phe Arg Lys Gln His Arg Ser Phe Arg Arg
                580                 585                 590
Arg His Phe Leu Thr Gly Leu Pro Asn Gly Gly Arg Pro Arg Arg Ser
                595                 600                 605
```

```
Leu Val Ala Pro Glu Gly Arg Pro Met Arg His Glu Asp Trp Thr Asn
    610                 615                 620

Pro Glu Leu Thr Ala Phe Gly Leu Leu Leu His Gly Asp Ala Ile Gln
625                 630                 635                 640

Gly Thr Asp Glu His Gly Arg Pro Phe Arg Asp Thr Phe Leu Ile
                645                 650                 655

Leu Phe Asn Asn Gly Ser Glu Ala Val Pro Val Val Pro Glu Val
                660                 665                 670

Cys Ser Cys Gly Lys Pro His His Trp Glu Val Val Pro Val Phe Gln
            675                 680                 685

Arg Asn Val Glu Pro Pro Thr Cys Ala Pro Gly Glu Thr Leu Ser Leu
    690                 695                 700

Pro Pro Gly Val Leu Thr Val Leu Val Ala Val Pro Pro Phe Ser Asp
705                 710                 715                 720

Gly Asn Thr Glu Pro Ala
                725

<210> SEQ ID NO 14
<211> LENGTH: 2736
<212> TYPE: DNA
<213> ORGANISM: Bacillus acidopullulyticus
<220> FEATURE:
<221> NAME/KEY: gene
<222> LOCATION: (1)..(2736)
<223> OTHER INFORMATION: pulB, pullulanase

<400> SEQUENCE: 14
aaaaaatgct taatagaagg agtgtaatct gtgtccctaa tacgttctag gtataatcat      60
tttgtcattc tttttactgt cgccataatg tttctaacag tttgtttccc cgcttataaa     120
gctttagcag attctacctc gacagaagtc attgtgcatt atcatcgttt tgattctaac     180
tatgcaaatt gggatctatg gatgtggcca tatcaaccag ttaatggtaa tggagcagca     240
tacgagtttt ctggaaagga tgattttggc gttaaagcag atgttcaagt gcctggggat     300
gatacacagg taggtctgat tgtccgtaca aatgattgga gccaaaaaaa tacatcagac     360
gatctccata ttgatctgac aaaggggcat gaaatatgga ttgttcaggg ggatcccaat     420
atttattaca atctgagtga tgcgcaggct gcagcgactc caaaggtttc gaatgcgtat     480
ttggataatg aaaaaacagt attggcaaag ctaactaatc caatgacatt atcagatgga     540
tcaagcggct ttacggttac agataaaaca acagggaac aaattccagt taccgctgca     600
acaaatgcga actcagcctc ctcgtctgag cagacagact tggttcaatt gacgttagcc     660
agtgcaccgg atgttttccca tacaataca gtaggagcag ccggttatga agcagtcaat     720
ctcataccac gaaatgtatt aaatttgcct cgttattatt acagcggaaa tgatttaggt     780
aacgtttatt caaataaggc aacggccttc cgtgtatggg ctccaactgc ttcggatgtc     840
caattacttt tatacaatag tgaaacagga cctgtaacca aacagcttga aatgcaaaag     900
agtgataacg gtacatggaa actgaaggtc cctggtaatc tgaaaaattg gtattatctc     960
tatcaggtaa cggtgaatgg gaagacacaa acagccgttg accccttatgt gcgtgctatt    1020
tcagtcaatg caacacgtgg tatgatagtc gatttagaag atacgaatcc tcctggatgg    1080
aaagaagatc atcaacagac acctgcgaac ccagtggatg aagtaatcta cgaagtgcat    1140
gtgcgtgatt tttcgattga tgctaattca ggcatgaaaa ataaagggaa atatcttgcc    1200
tttacagaac atggcacaaa aggccctgat aacgtgaaaa cgggtattga tagtttgaag    1260
```

-continued

```
gaattaggaa tcaatgctgt tcaattacag ccgattgaag aatttaacag cattgatgaa    1320
acccaaccaa atatgtataa ctggggctat gacccaagaa actacaacgt ccctgaagga    1380
gcgtatgcaa ctacaccaga aggaacggct cgcattaccc agttaaagca actgattcaa    1440
agcattcata aagatcggat tgctatcaat atggatgtgg tctataacca tacctttaac    1500
gtaggagtgt ctgattttga taagattgtt ccgcaatact attatcggac agacagcgca    1560
ggtaattata cgaacggctc aggtgtaggt aatgaaattg cgaccgagcg tccgatggtc    1620
caaaagttcg ttctggattc tgttaaatat tgggtaaagg aataccatat cgacggcttc    1680
cgtttcgatc ttatggctct tttaggaaaa gacaccatgg ccaaaatatc aaaagagctt    1740
catgctatta atcctggcat tgtcctgtat ggagaaccat ggactggcgg tacctctgga    1800
ttatcaagcg accaactcgt tacgaaaggt cagcaaaagg gcttgggaat tggcgtattc    1860
aacgataata ttcggaacgg actcgatggt aacgttttg ataaatcggc acaaggattt     1920
gcaacaggag atccaaacca agttaatgtc attaaaaata gagttatggg aagtatttca    1980
gatttcactt cggcacctag cgaaaccatt aactatgtaa caagccatga taatatgaca    2040
ttgtgggata aaattagcgc aagtaatccg aacgatacac aagcagatcg aattaagatg    2100
gatgaattgg ctcaagctgt ggtatttact tcacaagggg taccatttat gcaaggtgga    2160
gaagaaatgc tgcggacaaa aggcggtaat gataatagtt acaatgccgg ggatagcgtg    2220
aatcagttcg attggtcaag aaaagcacaa tttgaaaatg tattcgacta ctattcttgg    2280
ttgattcatc tacgtgataa tcacccagca ttccgtatga cgacagcgga tcaaatcaaa    2340
caaaatctca ctttcttgga tagcccaacg aacactgtag catttgaatt aaaaaatcat    2400
gccaatcatg ataaatggaa aaacattata gttatgtata atccaaataa aactgcacaa    2460
actctcactc taccaagtgg aaattggaca attgtaggat taggcaatca agtaggtgag    2520
aaatcactag gccatgtaaa tggcacggtt gaggtgccag ctcttagtac gatcattctt    2580
catcagggta catctgaaga tgtcattgat caaaattaat attgattaag aaatgatttg    2640
taaaacattt aagtccattt acacgggata ctgtgtaaat ggattttagt tttatccgta    2700
gcatgtgtta aagaagtaaa tagtaaatgg caattt                              2736
```

The invention claimed is:

1. An isolated variant pullulanase, said variant having an amino acid sequence which has a degree of identity to SEQ ID NO:1 or SEQ ID NO:2 of at least 90% when identity is determined using GAP (version 8), using a gap creation penalty of 3.0 and a gap extension penalty of 0.1, wherein the variant comprises at least one amino acid substitution in a position corresponding to N475 and N480 in SEQ ID NO:2, and wherein the variant has pullulanase activity.

2. The variant pullulanase of claim 1, wherein said variant comprises an at least one amino acid substitution in a position corresponding to N475 in SEQ ID NO:2.

3. The variant pullulanase of claim 1, wherein said variant comprises an at least one amino acid substitution in a position corresponding to N480 in SEQ ID NO:2.

4. The variant pullulanase of claim 1, wherein said variant has an amino acid sequence which has a degree of identity to SEQ ID NO:1 of at least 90% when identity is determined using GAP (version 8), using a gap creation penalty of 3.0 and a gap extension penalty of 0.1.

5. The variant pullulanase of claim 1, wherein said variant has an amino acid sequence which has a degree of identity to SEQ ID NO:1 of at least 95% when identity is determined using GAP (version 8), using a gap creation penalty of 3.0 and a gap extension penalty of 0.1.

6. The variant pullulanase of claim 1, wherein said variant has an amino acid sequence which has a degree of identity to SEQ ID NO:1 of at least 97% when identity is determined using GAP (version 8), using a gap creation penalty of 3.0 and a gap extension penalty of 0.1.

7. The variant pullulanase of claim 1, wherein said variant has an amino acid sequence which has a degree of identity to SEQ ID NQ:1 of at least 99% when identity is determined using GAP (version 8), using a gap creation penalty of 3.0 and a gap extension penalty of 0.1.

8. The variant pullulanase of claim 1, wherein said variant has an amino acid sequence which has a degree of identity to SEQ ID NO:2 of at least 90% when identity is determined using GAP (version 8), using a gap creation penalty of 3.0 and a gap extension penalty of 0.1.

9. The variant pullulanase of claim 1, wherein said variant has an amino acid sequence which has a degree of identity to SEQ ID NO:2 of at least 95% when identity is determined using GAP (version 8), using a gap creation penalty of 3.0 and a gap extension penalty of 0.1.

10. The variant pullulanase of claim 1, wherein said variant has an amino acid sequence which has a degree of identity to SEQ ID NO:2 of at least 97% when identity is determined using GAP (version 8), using a gap creation penalty of 3.0 and a gap extension penalty of 0.1.

11. The variant pullulanase of claim 1, wherein said variant has an amino acid sequence which has a degree of identity to SEQ ID NO:2 of at least 99% when identity is determined using GAP (version 8), using a gap creation penalty of 3.0 and a gap extension penalty of 0.1.

* * * * *